United States Patent
Spurbeck

(10) Patent No.: US 11,441,176 B2
(45) Date of Patent: Sep. 13, 2022

(54) METHODS AND CONTROL COMPOSITIONS FOR A QUANTITATIVE POLYMERASE CHAIN REACTION

(71) Applicant: BATTELLE MEMORIAL INSTITUTE, Columbus, OH (US)

(72) Inventor: Rachel R. Spurbeck, Columbus, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 0 days.

(21) Appl. No.: 16/714,125

(22) Filed: Dec. 13, 2019

(65) Prior Publication Data

US 2020/0216886 A1    Jul. 9, 2020

Related U.S. Application Data

(60) Provisional application No. 62/779,200, filed on Dec. 13, 2018.

(51) Int. Cl.
| | |
|---|---|
| *C12Q 1/6851* | (2018.01) |
| *C12Q 1/6818* | (2018.01) |
| *C12Q 1/6823* | (2018.01) |
| *C12Q 1/686*  | (2018.01) |

(52) U.S. Cl.
CPC ........... *C12Q 1/6851* (2013.01); *C12Q 1/686* (2013.01); *C12Q 1/6818* (2013.01); *C12Q 1/6823* (2013.01)

(58) Field of Classification Search
CPC .. C12Q 1/6851; C12Q 1/6818; C12Q 1/6823; C12Q 1/686; C12Q 2545/101; C12Q 2563/179; C12Q 2563/185; C12N 15/10
See application file for complete search history.

(56) References Cited

U.S. PATENT DOCUMENTS

| | | |
|---|---|---|
| 8,785,130 B2 | 7/2014 | Vinayagamoorthy et al. |
| 2006/0058249 A1 | 3/2006 | Tong et al. |
| 2006/0073506 A1 | 4/2006 | Frederick et al. |
| 2015/0322508 A1 | 11/2015 | Mitne Neto et al. |
| 2016/0257984 A1 | 9/2016 | Hardenbol et al. |
| 2016/0257993 A1 | 9/2016 | Fu et al. |
| 2016/0281182 A1 | 9/2016 | Monpoeho et al. |
| 2017/0275691 A1 | 9/2017 | Christians et al. |
| 2017/0292149 A1* | 10/2017 | Sherwood ............ C12Q 1/6846 |
| 2019/0300948 A1* | 10/2019 | Cuppens ........... C12Q 2563/179 |

FOREIGN PATENT DOCUMENTS

| | | |
|---|---|---|
| EP | 3246412 | 11/2017 |
| WO | 2004/083819 | 9/2004 |
| WO | 2009/036525 | 3/2009 |
| WO | 2011/156795 | 12/2011 |
| WO | 2016179530 | 11/2016 |
| WO | 2017/058936 | 4/2017 |
| WO | 2017/165864 | 9/2017 |
| WO | 2017192974 | 11/2017 |
| WO | 2019/226648 | 11/2019 |

OTHER PUBLICATIONS

International Search Report for PCT/US19/66326 dated Apr. 6, 2020.
PCT Search Report and Written Opinion prepared for PCT/US2019/033311, dated Oct. 23, 2019.
Kaifu Chen et al. The Overlooked Fact: Fundamental Need for Spike-In Control for Virtually All Genome-Wide Analysis Molecular and Cellular Biology March 206 vol. 36 No. 5, 2016.
Qu et al. Development of ERCC RNA Spike-In Control Mixes J. Biomol. Tech. Oct. 2011; 22(Suppl): S46.
Wong et al. ANAQUIN: a software toolkit for the analysis of spike-in controls for next generation sequencing Bioinformatics, 33(11), 2017, 1723-1724. doi: 10.1093/bioinformatics/btx038 Advance Access Publication Date: Jan. 27, 2017.
Quail et al. SASI-Seq: sample assurance Spike-Ins, and highly differentiating 384 barcoding for Illumina sequencing BMC Genomics vol. 15, Article No. 110 (2014) Published: Feb. 7, 2014.
Chen et al. Effects of GC Bias in Next-Generation-Sequencing data on De Novo Genome Assembly PLoS One 8(4):e62856. doi: 10.137/journal.pone.0062856, 2013.
Kozarewa et al. Nature Methods 2009; 6:291-295.
Kojima et al. Nucleic Acids Research, 2005, 33(17) e 150.
Dauphin et al. Journal of Applied Microbiology, 2010, 108, 163-72.
Hammer et al. FEBS Letters, 2012, 586, 1882-90.
Zelikin et al. ACSNANO, 2007, 1(1) 63-9.
Jiang, L. et al., "Synthetic spike-in standards for RNA-seq experiments," Genome Research, 2011, 21(9) 1543-51.

* cited by examiner

*Primary Examiner* — David C Thomas

(74) *Attorney, Agent, or Firm* — Barnes & Thornburg LLP

(57) ABSTRACT

The invention relates to control compositions for a quantitative polymerase chain reaction. More particularly, the invention relates to control compositions for a quantitative polymerase chain reaction having at least one barcode sequence fragment and at least a first and a second primer binding site fragment, and to methods of their use.

19 Claims, 9 Drawing Sheets

Specification includes a Sequence Listing.

Native sequence (left panel middle bar) is replaced with barcode (right panel middle bar)

Probe with fluorophore

Encapsulated cross-contamination control

Probe with fluorophore

Encapsulated cross-contamination control plasmid

Result in quantification of different GC contents

Unbiased

Biased against low GC

Control for Differential
Lysis

METHODS AND CONTROL COMPOSITIONS FOR A QUANTITATIVE POLYMERASE CHAIN REACTION

CROSS-REFERENCE TO RELATED APPLICATIONS

This application claims priority under 35 U.S.C. § 119(e) to U.S. Provisional Application Ser. No. 62/779,200 filed on Dec. 13, 2018, the entire disclosure of which is incorporated herein by reference.

SEQUENCE LISTING

The instant application contains a Sequence Listing which has been submitted electronically in ASCII format and is hereby incorporated by reference in its entirety. Said ASCII copy, created on Feb. 7, 2020, is named 920006-304269_SL.txt and is 758,774 bytes in size.

FIELD OF THE DISCLOSURE

The invention relates to control compositions for a quantitative polymerase chain reaction. More particularly, the invention relates to control compositions for a quantitative polymerase chain reaction having at least one barcode sequence fragment and at least a first and a second primer binding site fragment, and to methods of their use.

BACKGROUND AND SUMMARY OF THE INVENTION

The quantitative polymerase chain reaction (qPCR), which is also referred to as q-RT-PCR (i.e., quantitative real-time polymerase chain reaction), suffers from a lack of spike-in controls that can be used in every step of analysis from DNA extraction to DNA amplification. Sample swapping or sample-to-sample contamination can occur during any of these steps, but without a priori knowledge of what is in the sample, it may not be known if the samples were contaminated or swapped or contained similar genetic profiles. qPCR is used for clinical diagnosis of infectious diseases, cancer, and other genetic disorders. If a sample contaminates a neighboring sample, or sample swapping occurs, during sample processing or qPCR a healthy person could be diagnosed as having an infection or another disorder. Thus, methods and compositions to ensure that sample swapping or sample-to-sample contamination has not occurred during sample processing or qPCR are important.

Applicant has invented barcoded DNA molecules that are optionally encapsulated in a simulated cell membrane for use in qPCR. The barcoded molecule is flanked, directly or indirectly, with specific primer binding site fragments so that the barcode is amplified during a qPCR protocol. In one embodiment, a unique Taqman™ probe can be designed to correspond with each barcode to enable detection and differentiation of barcodes during qPCR. The probe can bind to the barcode to detect the barcode, presenting a unique signal to the qPCR device that can be differentiated from the signal produced by the qPCR target of the assay. In one aspect, the cross-contamination controls can be spiked into a sample at sample collection thereby controlling the whole qPCR sample processing workflow.

The present invention provides qPCR controls that can be used starting after the extraction step (e.g., by spiking the extract with the control constructs) or in every step of the qPCR analysis of an unknown test sample (e.g., from nucleic acid extraction to nucleic acid purification to the qPCR itself). In one embodiment, nucleic acid constructs comprising a barcode sequence fragment are provided that can be encapsulated in a simulated cell membrane (e.g., a simulated bacterial cell membrane or eukaryotic cell membrane), or embedded directly in the genome of an organism for use as qPCR spike-in controls. In one aspect, the barcode sequence fragment comprises a unique sequence not present in any known genome. In one embodiment, the qPCR reaction controls can be spiked into the unknown test sample prior to or after nucleic acid extraction and then can be detected in the final samples during qPCR amplification. In another embodiment, different nucleic acid constructs (i.e., with different barcode sequence fragments) can be spiked into different qPCR samples so that cross-contamination of samples or sample swapping can be detected.

In one embodiment, the barcode sequence fragment for use in qPCR can be flanked by universal sequence fragments. The universal sequence fragments can add length to the nucleic acid construct. The barcode sequence fragment is flanked by primer binding site fragments (i.e., directly or indirectly linked to the barcode sequence fragment) so that the nucleic acid construct comprising the barcode sequence fragment can be amplified during qPCR.

In various embodiments, samples with microorganisms containing nucleic acids (e.g., DNA), or samples with other sources of nucleic acids, may be analyzed by qPCR using the control compositions described herein. The samples can be, for example, selected from the group consisting of urine, nasal secretions, nasal washes, inner ear fluids, bronchial lavages, bronchial washes, alveolar lavages, spinal fluid, bone marrow aspirates, sputum, pleural fluids, synovial fluids, pericardial fluids, peritoneal fluids, saliva, tears, gastric secretions, a stool sample, reproductive tract secretions, lymph fluid, whole blood, serum, plasma, a tissue sample, a soil sample, a water sample, a food sample, an air sample, a plant sample, an industrial waste sample, a surface wipe sample, a dust sample, a hair sample, and an animal sample.

In another embodiment, a method is provided for the use of qPCR spike-in controls that simultaneously 1) control for cross-contamination and/or sample swapping and 2) control for different GC content samples (e.g., low, balanced, and high GC content) and/or for different lysis efficiencies. The barcoded DNA molecules are flanked, directly or indirectly, by primer binding site fragments. In one aspect, barcoded DNA molecules are produced with different GC contents, using GC content fragments. In another embodiment, the barcode sequence fragments and the GC content fragments are flanked by universal sequence fragments and the universal sequence fragments are flanked by primer binding site fragments. In another embodiment, the nucleic acid construct is encapsulated in a simulated cell membrane. In this embodiment, the barcode sequence fragments can be used to verify that no cross-contamination or sample swapping occurred during sample preparation or processing. Also in this embodiment, the different GC content fragments (e.g., low, balanced, and high GC content) have the same barcode sequence fragment at each GC percentage (e.g., low, balanced, and high GC content), but in different samples, the barcode sequence fragments are unique. In this embodiment, the GC content fragments can be used to control for GC content bias for example for the polymerase used in qPCR. In this embodiment, the encapsulation method can also be varied to control for different resistances to lysis to mimic, for example, Gram positive, Gram negative, and fungal cell walls. In this encapsulation embodiment, the type of encapsulation method can be correlated to a unique barcode sequence fragment in the nucleic acid construct to enable differentiation during qPCR.

The following clauses, and combinations thereof, provide various additional illustrative aspects of the invention described herein. The various embodiments described in any other section of this patent application, including the section titled "DETAILED DESCRIPTION OF ILLUSTRATIVE EMBODIMENTS" and the "EXAMPLES" are applicable to any of the following embodiments of the invention described in the numbered clauses below.

1. A qPCR control composition, said control composition comprising a nucleic acid construct comprising at least one barcode sequence fragment wherein the nucleic acid construct further comprises at least a first and a second primer binding site fragment.
2. The control composition of clause 1 wherein the control composition is used to determine if cross-contamination between qPCR samples has occurred.
3. The control composition of clause 1 wherein the control composition is used to determine if sample swapping has occurred during analysis by qPCR.
4. The control composition of any one of clauses 1 to 3 wherein the nucleic acid construct is a deoxyribonucleic acid construct.
5. The control composition of any one of clauses 1 to 4 wherein the nucleic acid construct comprises at least one universal sequence fragment to add length to the nucleic acid construct.
6. The control composition of clause 5 wherein the nucleic acid construct comprises a first universal sequence fragment linked to the 5' end of the barcode sequence fragment and a second universal sequence fragment linked to the 3' end of the barcode sequence fragment.
7. The control composition of any one of clauses 1 to 6 in combination with a probe.
8. The control composition of clause 6 wherein the first primer binding site fragment is linked at its 3'end to the 5' end of the first universal sequence fragment and the second primer binding site fragment is linked at its 5' end to the 3' end of the second universal sequence fragment.
9. The control composition of any one of clauses 1 to 8 wherein the primer binding site fragments range in length from about 15 base pairs to about 30 base pairs.
10. The control composition of any one of clauses 1 to 9 wherein the nucleic acid construct ranges in length from about 80 base pairs to about 300 base pairs.
11. The control composition of any one of clauses 1 to 9 wherein the nucleic acid construct ranges in length from about 80 base pairs to about 250 base pairs.
12. The control composition of any one of clauses 1 to 9 wherein the nucleic acid construct ranges in length from about 80 base pairs to about 200 base pairs.
13. The control composition of any one of clauses 1 to 9 wherein the nucleic acid construct ranges in length from about 80 base pairs to about 160 base pairs.
14. The control composition of any one of clauses 1 to 13 wherein the nucleic acid construct is encapsulated.
15. The control composition of clause 14 wherein the nucleic acid construct is encapsulated in a liposome.
16. The control composition of clause 15 wherein the liposome comprises a lipid selected from the group consisting of cholesterol, a lipopolysaccharide, a peptidoglycan, a PEG, a teichoic acid, a phospholipid, and combinations thereof.
17. The control composition of any one of clauses 1 to 13 wherein the nucleic acid construct is incorporated into the genome of a microorganism.
18. The control composition of any one of clauses 1 to 17 wherein the barcode sequence fragment comprises a unique sequence not present in any known genome.
19. The control composition of any one of clauses 1 to 16 wherein the nucleic acid construct is incorporated into a plasmid.
20. A kit comprising the qPCR control composition of any one of clauses 1 to 19.
21. The kit of clause 20 further comprising a reagent for nucleic acid extraction.
22. The kit of clause 20 or 21 further comprising a reagent for nucleic acid purification.
23. The kit of any one of clauses 20 to 22 further comprising a polymerase.
24. The kit of any one of clauses 20 to 23 further comprising a probe.
25. The kit of clause 24 wherein the probe is a TaqMan probe.
26. The kit of any one of clauses 20 to 25 wherein the kit comprises more than one control composition of any one of clauses 1 to 19 wherein each control composition comprises a different nucleic acid construct wherein the different nucleic acid constructs comprise different barcode sequence fragments.
27. A method for monitoring cross-contamination or sample swapping over one or more steps of a qPCR protocol including collection of a sample comprising DNA, DNA extraction from the sample, purification of the extracted DNA, and qPCR, the method comprising,
   a) spiking the sample with a control composition comprising a nucleic acid construct wherein the nucleic acid construct comprises at least one barcode sequence fragment, wherein the nucleic acid construct is a deoxyribonucleic acid construct, and wherein the nucleic acid construct further comprises at least a first and a second primer binding site fragment;
   b) extracting total DNA wherein total DNA comprises the DNA from the sample and DNA from the nucleic acid construct;
   c) purifying total DNA;
   d) performing qPCR on the extracted, purified total DNA; and
   e) detecting the nucleic acid construct in total DNA using a probe.
28. The method of clause 27 wherein the sample is selected from the group consisting of urine, nasal secretions, nasal washes, inner ear fluids, bronchial lavages, bronchial washes, alveolar lavages, spinal fluid, bone marrow aspirates, sputum, pleural fluids, synovial fluids, pericardial fluids, peritoneal fluids, saliva, tears, gastric secretions, a stool sample, reproductive tract secretions, lymph fluid, whole blood, serum, plasma, a tissue sample, a soil sample, a water sample, a food sample, an air sample, a plant sample, an industrial waste sample, a surface wipe sample, a dust sample, a hair sample, an agricultural sample, and an animal sample.
29. The method of clause 27 or 28 wherein the method is used to determine if cross-contamination between samples has occurred.
30. The method of clause 27 or 28 wherein the method is used to determine if sample swapping has occurred.
31. The method of any one of clauses 27 to 30 wherein the nucleic acid construct is amplified.

32. The method of any one of clauses 27 to 31 wherein the nucleic acid construct further comprises at least a first and a second universal sequence fragment.

33. The method of clause 32 wherein the first universal sequence fragment is linked to the 5' end of the barcode sequence fragment and the second universal sequence fragment is linked to the 3' end of the barcode sequence fragment.

34. The method of any one of clauses 27 to 33 wherein the probe is a TaqMan probe.

35. The method of any one of clauses 33 to 34 wherein the first primer binding site fragment is linked at its 3'end to the 5' end of the first universal sequence fragment and the second primer binding site fragment is linked at its 5' end to the 3' end of the second universal sequence fragment.

36. The method of any one of clauses 27 to 35 wherein the primer binding site fragments range in length from about 15 base pairs to about 30 base pairs.

37. The method of any one of clauses 27 to 36 wherein the nucleic acid construct ranges in length from about 80 base pairs to about 300 base pairs.

38. The method of any one of clauses 27 to 36 wherein the nucleic acid construct ranges in length from about 80 base pairs to about 250 base pairs.

39. The method of any one of clauses 27 to 36 wherein the nucleic acid construct ranges in length from about 80 base pairs to about 200 base pairs.

40. The method of any one of clauses 27 to 36 wherein the nucleic acid construct ranges in length from about 80 base pairs to about 160 base pairs.

41. The method of any one of clauses 27 to 40 wherein the nucleic acid construct is encapsulated.

42. The method of clause 41 wherein the nucleic acid construct is encapsulated in a liposome.

43. The method of clause 42 wherein the liposome comprises a lipid selected from the group consisting of cholesterol, a lipopolysaccharide, a peptidoglycan, a PEG, a teichoic acid, a phospholipid, and combinations thereof.

44. The method of any one of clauses 27 to 40 wherein the nucleic acid construct is incorporated into the genome of a microorganism.

45. The method of any one of clauses 27 to 44 wherein the barcode sequence fragment comprises a unique sequence not present in any known genome.

46. The method of any one of clauses 27 to 43 wherein the nucleic acid construct is incorporated into a plasmid.

47. The method of clause 43 wherein the liposome comprises a peptidoglycan.

48. The method of clause 43 wherein the liposome comprises a lipopolysaccharide.

49. A qPCR control composition, said control composition comprising a nucleic acid construct comprising at least one barcode sequence fragment and at least one GC content fragment, wherein the nucleic acid construct further comprises at least a first and a second primer binding site fragment.

50. The control composition of clause 49 wherein one or more of the GC content fragments has a GC content of about 1 to about 40 percent.

51. The control composition of clause 49 wherein one or more of the GC content fragments has a GC content of about 40 to about 60 percent.

52. The control composition of clause 49 wherein one or more of the GC content fragments has a GC content of about 60 to about 100 percent.

53. The control composition of any one of clauses 49 to 52 comprising nucleic acid constructs with GC content fragments with at least two different percent GC contents.

54. The control composition of any one of clauses 49 to 52 comprising nucleic acid constructs with GC content fragments with at least three different percent GC contents.

55. The control composition of any one of clauses 49 to 52 comprising nucleic acid constructs with GC content fragments with at least four different percent GC contents.

56. The control composition of clause 54 wherein the percent GC contents are about 1 to about 40 percent, about 40 percent to about 60 percent, and about 60 percent to about 100 percent.

57. The control composition of any one of clauses 49 to 56 wherein the control composition is used to determine if cross-contamination between samples for qPCR has occurred.

58. The control composition of any one of clauses 49 to 56 wherein the control composition is used to determine if sample swapping has occurred for qPCR samples.

59. The control composition of any one of clauses 49 to 58 wherein the GC content fragment is used to control for polymerase GC content bias.

60. The control composition of any one of clauses 49 to 59 in combination with a probe.

61. The control composition of any one of clauses 49 to 60 wherein the nucleic acid construct is a deoxyribonucleic acid construct.

62. The control composition of any one of clauses 49 to 61 wherein the nucleic acid construct further comprises at least a first and a second universal sequence fragment.

63. The control composition of clause 62 wherein the first universal sequence fragment is linked to the 5' end of the barcode sequence fragment, the barcode sequence fragment is between the first universal sequence fragment and the GC content fragment, and the second universal sequence fragment is linked to the 3' end of the GC content fragment.

64. The control composition of clause 60 wherein the probe is a TaqMan probe.

65. The control composition of any one of clauses 62 to 64 wherein the first primer binding site fragment is linked at its 3'end to the 5' end of the first universal sequence fragment and the second primer binding site fragment is linked at its 5' end to the 3' end of the second universal sequence fragment.

66. The control composition of any one of clauses 49 to 65 wherein the primer binding site fragments range in length from about 15 base pairs to about 30 base pairs.

67. The control composition of any one of clauses 49 to 66 wherein the nucleic acid construct ranges in length from about 80 base pairs to about 300 base pairs.

68. The control composition of any one of clauses 49 to 66 wherein the nucleic acid construct ranges in length from about 80 base pairs to about 250 base pairs.

69. The control composition of any one of clauses 49 to 66 wherein the nucleic acid construct ranges in length from about 80 base pairs to about 200 base pairs.

70. The control composition of any one of clauses 49 to 66 wherein the nucleic acid construct ranges in length from about 80 base pairs to about 160 base pairs.

71. The control composition of any one of clauses 49 to 70 wherein the nucleic acid construct is encapsulated.

72. The control composition of clause 71 wherein the nucleic acid construct is encapsulated in a liposome.

73. The control composition of clause 72 wherein the liposome comprises a lipid selected from the group consisting of cholesterol, a lipopolysaccharide, a peptidoglycan, a PEG, a teichoic acid, a phospholipid, and combinations thereof.

74. The control composition of any one of clauses 49 to 73 wherein the barcode sequence fragment comprises a unique sequence not present in any known genome. 75. The control composition of any one of clauses 49 to 70 wherein the nucleic acid construct is incorporated into the genome of a microorganism.

76. The control composition of any one of clauses 49 to 74 wherein the nucleic acid construct is incorporated into a plasmid.

77. A kit comprising the qPCR control composition of any one of clauses 49 to 76.

78. The kit of clause 77 further comprising a reagent for nucleic acid extraction. 79. The kit of clause 77 or 78 further comprising a reagent for nucleic acid purification.

80. The kit of any one of clauses 77 to 79 further comprising a probe.

81. The kit of clause 80 wherein the probe is a TaqMan probe.

82. The kit of any one of clauses 77 to 81 further comprising a polymerase.

83. The kit of any one of clauses 77 to 82 wherein the kit comprises more than one control composition of any one of clauses 49 to 76 wherein each control composition comprises a different nucleic acid construct wherein the different nucleic acid constructs comprise different barcode sequence fragments.

84. The kit of any one of clauses 77 to 83 wherein the kit comprises more than one control composition of any one of clauses 49 to 76 and wherein the nucleic acid construct in each control composition is encapsulated in a different type of liposome.

85. A method for monitoring sample cross-contamination and/or sample swapping of nucleic acids during qPCR, the method comprising,
 a) extracting DNA from a sample;
 b) purifying the DNA;
 c) spiking the sample, after DNA extraction and purification and before qPCR, with a control composition comprising a nucleic acid construct wherein the nucleic acid construct comprises at least one barcode sequence fragment and at least a first and a second primer binding site fragment, and at least one GC content fragment, and wherein the nucleic acid construct is a deoxyribonucleic acid construct, wherein total DNA is obtained after spiking the sample, and wherein total DNA comprises the DNA from the sample and the DNA from the nucleic acid construct;
 d) performing qPCR on the extracted, purified total DNA; and
 e) detecting the nucleic acid construct in total DNA using a probe.

86. A method for monitoring sample cross-contamination and/or sample swapping of nucleic acids during qPCR, the method comprising,
 a) spiking a sample with a control composition comprising a nucleic acid construct wherein the nucleic acid construct comprises at least one barcode sequence fragment and at least a first and a second primer binding site fragment, and at least one GC content fragment and wherein the nucleic acid construct is a deoxyribonucleic acid construct;
 b) extracting total DNA from the sample wherein total DNA comprises the DNA from the sample and the DNA from the nucleic acid construct;
 c) purifying total DNA;
 d) performing qPCR on the extracted, purified total DNA; and
 e) detecting the nucleic acid construct in total DNA using a probe.

87. The method of clause 86 wherein sample cross-contamination and/or sample swapping can be monitored over all steps of a qPCR protocol including collection of the sample, extraction of total DNA, purification of the extracted total DNA, and qPCR.

88. The method of any one of clauses 85 to 87 wherein the sample is selected from the group consisting of urine, nasal secretions, nasal washes, inner ear fluids, bronchial lavages, bronchial washes, alveolar lavages, spinal fluid, bone marrow aspirates, sputum, pleural fluids, synovial fluids, pericardial fluids, peritoneal fluids, saliva, tears, gastric secretions, a stool sample, reproductive tract secretions, lymph fluid, whole blood, serum, plasma, a tissue sample, a soil sample, a water sample, a food sample, an air sample, a plant sample, an industrial waste sample, a surface wipe sample, a dust sample, a hair sample, an agricultural sample, and an animal sample.

89. The method of any one of clauses 85 to 88 wherein the probe is a TaqMan probe.

90. The method of any one of clauses 85 to 89 wherein one of the GC content fragments has a GC content of about 1 to about 40 percent.

91. The method of any one of clauses 85 to 89 wherein one of the GC content fragments has a GC content of about 40 to about 60 percent.

92. The method of any one of clauses 85 to 89 wherein one of the GC content fragments has a GC content of about 60 to about 100 percent.

93. The method of any one of clauses 85 to 92 wherein the control composition comprises nucleic acid constructs with GC content fragments with at least two different percent GC contents.

94. The method of any one of clauses 85 to 92 wherein the control composition comprises nucleic acid constructs with GC content fragments with at least three different percent GC contents.

95. The method of any one of clauses 85 to 92 wherein the control composition comprises nucleic acid constructs with GC content fragments with at least four different percent GC contents.

96. The method of clause 94 wherein the GC contents are about 1 to about 40 percent, about 40 percent to about 60 percent, and about 60 percent to about 100 percent.

97. The method of any one of clauses 85 to 96 wherein the GC content fragment is used to control for polymerase GC content bias.

98. The method of any one of clauses 93 to 96 wherein at each of the different percent GC contents the nucleic acid constructs comprise the same barcode sequence fragments.

99. The method of any one of clauses 85 to 98 wherein the barcode sequence fragment comprises a unique sequence not present in any known genome.

100. The method of any one of clauses 85 to 99 wherein the nucleic acid construct further comprises at least a first and a second universal sequence fragment.

101. The method of clause 100 wherein the first universal sequence fragment is linked to the 5' end of the barcode sequence fragment, the barcode sequence fragment is between the first universal sequence fragment and the GC content fragment, and the second universal sequence fragment is linked to the 3' end of the GC content fragment.

102. The method of any one of clauses 85 to 101 wherein the nucleic acid construct is amplified.

103. The method of clause 100 or 101 wherein the first primer binding site fragment is linked at its 3' end to the 5' end of the first universal sequence fragment and the second primer binding site fragment is linked at its 5' end to the 3' end of the second universal sequence fragment.

104. The method of any one of clauses 85 to 103 wherein the primer binding site fragments range in length from about 15 base pairs to about 30 base pairs.

105. The method of any one of clauses 85 to 104 wherein the nucleic acid construct ranges in length from about 80 base pairs to about 300 base pairs.

106. The method of any one of clauses 85 to 104 wherein the nucleic acid construct ranges in length from about 80 base pairs to about 250 base pairs.

107. The method of any one of clauses 85 to 104 wherein the nucleic acid construct ranges in length from about 80 base pairs to about 200 base pairs.

108. The method of any one of clauses 85 to 104 wherein the nucleic acid construct ranges in length from about 80 base pairs to about 160 base pairs.

109. The method of any one of clauses 85 to 108 wherein the nucleic acid construct is encapsulated.

110. The method of clause 109 wherein the nucleic acid construct is encapsulated in a liposome.

111. The method of clause 110 wherein the liposome comprises a lipid selected from the group consisting of cholesterol, a lipopolysaccharide, a peptidoglycan, a PEG, a teichoic acid, a phospholipid, and combinations thereof.

112. The method of any one of clauses 85 to 111 wherein more than one type of control composition is used in the method.

113. The method of any one of clauses 85 to 111 wherein more than one type of control composition is used in the method wherein the nucleic acid construct in each type of control composition is encapsulated in a different type of liposome.

114. The method of clause 113 wherein each type of control composition with the nucleic acid construct encapsulated in a different type of liposome comprises a different barcode sequence fragment.

115. The method of any one of clauses 85 to 108 wherein the nucleic acid construct is incorporated into the genome of a microorganism.

116. The method of any one of clauses 85 to 113 wherein the nucleic acid construct is incorporated into a plasmid.

DETAILED DESCRIPTION OF ILLUSTRATIVE EMBODIMENTS

Figure 1:
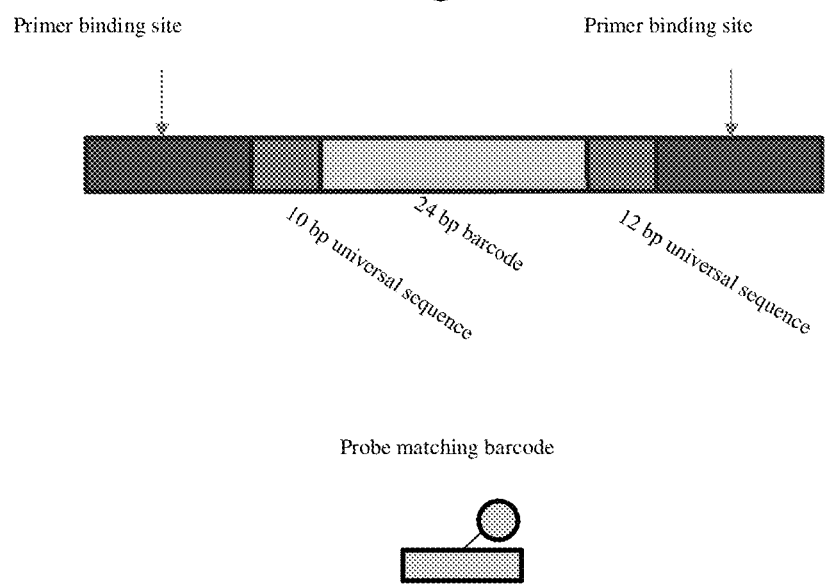
FIG. 1 shows schematically an exemplary nucleic acid construct as described herein comprising the unique barcode sequence fragment (e.g., 24 bases) that is not present in any known genome. The exemplary nucleic acid construct also comprises 10 bp and 12 bp universal sequence fragments and primer binding site fragments at the 5' and 3' ends of the nucleic acid construct. A probe with an attached fluorophore for qPCR is also shown. The probe is for hybridization to the barcode sequence fragment.

The present invention provides qPCR controls that can be used starting after the sample extraction step (e.g., by spiking the extract with the control constructs) or in every step of analysis of an unknown test sample (e.g., from nucleic acid extraction to nucleic acid purification to qPCR). In one embodiment, nucleic acid constructs comprising a barcode sequence fragment are provided that can be encapsulated in a simulated cell membrane (e.g., a simulated bacterial cell membrane or eukaryotic cell membrane), or embedded directly in the genome of an organism for use as spike-in qPCR controls. In one aspect, the barcode sequence fragment comprises a unique sequence not present in any known genome. In one embodiment, the qPCR controls can be spiked in the unknown test sample prior to or after nucleic acid extraction and then can be detected in the qPCR samples during amplification. In another embodiment, different nucleic acid constructs (i.e., with different barcode sequence fragments) can be spiked in different samples so that cross-contamination of samples or sample swapping can be detected.

In one embodiment, the barcode sequence fragment can be flanked at its 5' or 3' end, or both, by universal sequence fragments. The universal sequence fragments can add length to the nucleic acid construct. The barcode sequence fragment is flanked by primer binding site fragments (i.e., directly linked to the barcode sequence fragment, or indirectly linked to the barcode sequence fragment through the use of universal sequence fragments) so that the nucleic acid construct comprising the barcode sequence fragment can be amplified during qPCR. In another embodiment, a set of different nucleic acid construct spike-ins with different barcode sequence fragments, and different probes directed to the barcode sequence fragments, and in some embodiments directed to additional sequences such as GC content fragment sequences (see FIG. 4), can be used to allow for multiplexing of nucleic acid constructs with different barcode sequence fragments in a qPCR assay.

In various embodiments, samples with microorganisms containing nucleic acids (e.g., DNA), or samples with other sources of nucleic acids, may be analyzed by qPCR using the control compositions for qPCR described herein. The samples can be, for example, selected from the group consisting of urine, nasal secretions, nasal washes, inner ear fluids, bronchial lavages, bronchial washes, alveolar lavages, spinal fluid, bone marrow aspirates, sputum, pleural fluids, synovial fluids, pericardial fluids, peritoneal fluids, saliva, tears, gastric secretions, a stool sample, reproductive tract secretions, lymph fluid, whole blood, serum, plasma, hair, a tissue sample, a soil sample, a water sample, a food sample, an air sample, a plant sample, an industrial waste sample, a surface wipe sample, and an animal sample.

In another embodiment, compositions and methods are provided for the use of spike-in controls that simultaneously 1) control for cross-contamination and/or sample swapping and 2) control for different GC content samples (e.g., low, balanced, and high GC content) and/or for different lysis efficiencies. In one aspect, barcoded DNA molecules are produced with different GC contents, using GC content fragments, wherein barcode sequence fragments and GC content fragments are flanked by primer binding site fragments. In another embodiment, universal sequence fragments are included. In yet another embodiment, the nucleic acid construct can be encapsulated in a simulated cell membrane. In this embodiment, the barcode sequence fragments can be used to verify that no cross-contamination or sample swapping occurred during sample preparation or processing. In this quantitation embodiment, the different GC content fragments (e.g., low, balanced, and high GC content) have the same barcode sequence fragment at each GC percentage (e.g., low, balanced, and high GC content), but for each different sample, the barcode sequence fragments are unique. In this embodiment, the encapsulation method can also be varied to control for different resistances to lysis to mimic, for example, Gram-positive bacterial cell walls, Gram-negative bacterial cell walls, and fungal cell walls. In this encapsulation embodiment, the type of encapsulation method can be correlated to a unique barcode sequence fragment in the nucleic acid construct to enable differentiation in qPCR.

In one embodiment, the nucleic acid construct can be constructed with a first universal sequence fragment linked at the 5' end of a unique barcode sequence fragment, a GC content fragment (e.g., with high, balanced, or low GC content) linked to the 3' end of the barcode sequence fragment, a second universal sequence fragment linked at the 3' end of the GC content fragment, and 5' and 3' primer binding site fragments flanking the universal sequence fragments. In this embodiment, the universal sequence fragments can add length to the nucleic acid construct. In another embodiment, the universal sequence fragments are lacking. In yet another embodiment, the GC content fragment is lacking. In still another embodiment, both the universal sequence fragments and the GC content fragment are lacking. In these embodiments, the unique barcode sequence fragment is a sequence that is not present in any known genome.

An exemplary GC content fragment can contain about 60 to about 100 percent GC content for high GC content, about 40 to about 60 percent GC content for balanced GC content, and about 1 to about 40 percent GC content for low GC content. In various embodiments, the nucleic acid constructs can either be encapsulated to spike into samples at sample collection and control for full sample preparation and processing or can be unencapsulated and can be spiked in after extraction to control for subsequent steps in qPCR. In one aspect, two or more mixtures of three different GC content fragment constructs can be used (e.g., for different samples with each having a unique barcode sequence fragment).

The following clauses, and combinations thereof, provide various additional illustrative aspects of the invention described herein. The various embodiments described in any other section of this patent application, including the summary portion of the section titled "BACKGROUND AND SUMMARY", the "EXAMPLES", and this "DETAILED DESCRIPTION OF ILLUSTRATIVE EMBODIMENTS" section of the application are applicable to any of the following embodiments of the invention described in the numbered clauses below.

1. A qPCR control composition, said control composition comprising a nucleic acid construct comprising at least one barcode sequence fragment wherein the nucleic acid construct further comprises at least a first and a second primer binding site fragment.
2. The control composition of clause 1 wherein the control composition is used to determine if cross-contamination between qPCR samples has occurred.
3. The control composition of clause 1 wherein the control composition is used to determine if sample swapping has occurred during analysis by qPCR.
4. The control composition of any one of clauses 1 to 3 wherein the nucleic acid construct is a deoxyribonucleic acid construct.
5. The control composition of any one of clauses 1 to 4 wherein the nucleic acid construct comprises at least one universal sequence fragment to add length to the nucleic acid construct.
6. The control composition of clause 5 wherein the nucleic acid construct comprises a first universal sequence fragment linked to the 5' end of the barcode sequence fragment and a second universal sequence fragment linked to the 3' end of the barcode sequence fragment.
7. The control composition of any one of clauses 1 to 6 in combination with a probe.
8. The control composition of clause 6 wherein the first primer binding site fragment is linked at its 3'end to the 5' end of the first universal sequence fragment and the second primer binding site fragment is linked at its 5' end to the 3' end of the second universal sequence fragment.
9. The control composition of any one of clauses 1 to 8 wherein the primer binding site fragments range in length from about 15 base pairs to about 30 base pairs.
10. The control composition of any one of clauses 1 to 9 wherein the nucleic acid construct ranges in length from about 80 base pairs to about 300 base pairs.
11. The control composition of any one of clauses 1 to 9 wherein the nucleic acid construct ranges in length from about 80 base pairs to about 250 base pairs.
12. The control composition of any one of clauses 1 to 9 wherein the nucleic acid construct ranges in length from about 80 base pairs to about 200 base pairs.
13. The control composition of any one of clauses 1 to 9 wherein the nucleic acid construct ranges in length from about 80 base pairs to about 160 base pairs.
14. The control composition of any one of clauses 1 to 13 wherein the nucleic acid construct is encapsulated.
15. The control composition of clause 14 wherein the nucleic acid construct is encapsulated in a liposome.
16. The control composition of clause 15 wherein the liposome comprises a lipid selected from the group consisting of cholesterol, a lipopolysaccharide, a peptidoglycan, a PEG, a teichoic acid, a phospholipid, and combinations thereof.
17. The control composition of any one of clauses 1 to 13 wherein the nucleic acid construct is incorporated into the genome of a microorganism.
18. The control composition of any one of clauses 1 to 17 wherein the barcode sequence fragment comprises a unique sequence not present in any known genome.
19. The control composition of any one of clauses 1 to 16 wherein the nucleic acid construct is incorporated into a plasmid.
20. A kit comprising the qPCR control composition of any one of clauses 1 to 19.
21. The kit of clause 20 further comprising a reagent for nucleic acid extraction.
22. The kit of clause 20 or 21 further comprising a reagent for nucleic acid purification.
23. The kit of any one of clauses 20 to 22 further comprising a polymerase.
24. The kit of any one of clauses 20 to 23 further comprising a probe.
25. The kit of clause 24 wherein the probe is a TaqMan probe.
26. The kit of any one of clauses 20 to 25 wherein the kit comprises more than one control composition of any one of clauses 1 to 19 wherein each control composition comprises a different nucleic acid construct wherein the different nucleic acid constructs comprise different barcode sequence fragments.
27. A method for monitoring cross-contamination or sample swapping over one or more steps of a qPCR protocol including collection of a sample comprising DNA, DNA extraction from the sample, purification of the extracted DNA, and qPCR, the method comprising,
   a) spiking the sample with a control composition comprising a nucleic acid construct wherein the nucleic acid construct comprises at least one barcode sequence fragment, wherein the nucleic acid construct is a deoxyribonucleic acid construct, and wherein the nucleic acid construct further comprises at least a first and a second primer binding site fragment;
   b) extracting total DNA wherein total DNA comprises the DNA from the sample and DNA from the nucleic acid construct;
   c) purifying total DNA;
   d) performing qPCR on the extracted, purified total DNA; and
   e) detecting the nucleic acid construct in total DNA using a probe.
28. The method of clause 27 wherein the sample is selected from the group consisting of urine, nasal secretions, nasal washes, inner ear fluids, bronchial lavages, bronchial washes, alveolar lavages, spinal fluid, bone marrow aspirates, sputum, pleural fluids, synovial fluids, pericardial fluids, peritoneal fluids, saliva, tears, gastric secretions, a stool sample, reproductive tract secretions, lymph fluid, whole blood, serum, plasma, a tissue sample, a soil sample, a water sample, a food sample, an air sample, a plant sample, an industrial waste sample, a surface wipe sample, a dust sample, a hair sample, an agricultural sample, and an animal sample.
29. The method of clause 27 or 28 wherein the method is used to determine if cross-contamination between samples has occurred.
30. The method of clause 27 or 28 wherein the method is used to determine if sample swapping has occurred.
31. The method of any one of clauses 27 to 30 wherein the nucleic acid construct is amplified.

32. The method of any one of clauses 27 to 31 wherein the nucleic acid construct further comprises at least a first and a second universal sequence fragment.

33. The method of clause 32 wherein the first universal sequence fragment is linked to the 5' end of the barcode sequence fragment and the second universal sequence fragment is linked to the 3' end of the barcode sequence fragment.

34. The method of any one of clauses 27 to 33 wherein the probe is a TaqMan probe.

35. The method of any one of clauses 33 to 34 wherein the first primer binding site fragment is linked at its 3'end to the 5' end of the first universal sequence fragment and the second primer binding site fragment is linked at its 5' end to the 3' end of the second universal sequence fragment.

36. The method of any one of clauses 27 to 35 wherein the primer binding site fragments range in length from about 15 base pairs to about 30 base pairs.

37. The method of any one of clauses 27 to 36 wherein the nucleic acid construct ranges in length from about 80 base pairs to about 300 base pairs.

38. The method of any one of clauses 27 to 36 wherein the nucleic acid construct ranges in length from about 80 base pairs to about 250 base pairs.

39. The method of any one of clauses 27 to 36 wherein the nucleic acid construct ranges in length from about 80 base pairs to about 200 base pairs.

40. The method of any one of clauses 27 to 36 wherein the nucleic acid construct ranges in length from about 80 base pairs to about 160 base pairs.

41. The method of any one of clauses 27 to 40 wherein the nucleic acid construct is encapsulated.

42. The method of clause 41 wherein the nucleic acid construct is encapsulated in a liposome.

43. The method of clause 42 wherein the liposome comprises a lipid selected from the group consisting of cholesterol, a lipopolysaccharide, a peptidoglycan, a PEG, a teichoic acid, a phospholipid, and combinations thereof.

44. The method of any one of clauses 27 to 40 wherein the nucleic acid construct is incorporated into the genome of a microorganism.

45. The method of any one of clauses 27 to 44 wherein the barcode sequence fragment comprises a unique sequence not present in any known genome.

46. The method of any one of clauses 27 to 43 wherein the nucleic acid construct is incorporated into a plasmid.

47. The method of clause 43 wherein the liposome comprises a peptidoglycan.

48. The method of clause 43 wherein the liposome comprises a lipopolysaccharide.

49. A qPCR control composition, said control composition comprising a nucleic acid construct comprising at least one barcode sequence fragment and at least one GC content fragment, wherein the nucleic acid construct further comprises at least a first and a second primer binding site fragment.

50. The control composition of clause 49 wherein one or more of the GC content fragments has a GC content of about 1 to about 40 percent.

51. The control composition of clause 49 wherein one or more of the GC content fragments has a GC content of about 40 to about 60 percent.

52. The control composition of clause 49 wherein one or more of the GC content fragments has a GC content of about 60 to about 100 percent.

53. The control composition of any one of clauses 49 to 52 comprising nucleic acid constructs with GC content fragments with at least two different percent GC contents.

54. The control composition of any one of clauses 49 to 52 comprising nucleic acid constructs with GC content fragments with at least three different percent GC contents.

55. The control composition of any one of clauses 49 to 52 comprising nucleic acid constructs with GC content fragments with at least four different percent GC contents.

56. The control composition of clause 54 wherein the percent GC contents are about 1 to about 40 percent, about 40 percent to about 60 percent, and about 60 percent to about 100 percent.

57. The control composition of any one of clauses 49 to 56 wherein the control composition is used to determine if cross-contamination between samples for qPCR has occurred.

58. The control composition of any one of clauses 49 to 56 wherein the control composition is used to determine if sample swapping has occurred for qPCR samples.

59. The control composition of any one of clauses 49 to 58 wherein the GC content fragment is used to control for polymerase GC content bias.

60. The control composition of any one of clauses 49 to 59 in combination with a probe.

61. The control composition of any one of clauses 49 to 60 wherein the nucleic acid construct is a deoxyribonucleic acid construct.

62. The control composition of any one of clauses 49 to 61 wherein the nucleic acid construct further comprises at least a first and a second universal sequence fragment.

63. The control composition of clause 62 wherein the first universal sequence fragment is linked to the 5' end of the barcode sequence fragment, the barcode sequence fragment is between the first universal sequence fragment and the GC content fragment, and the second universal sequence fragment is linked to the 3' end of the GC content fragment.

64. The control composition of clause 60 wherein the probe is a TaqMan probe.

65. The control composition of any one of clauses 62 to 64 wherein the first primer binding site fragment is linked at its 3'end to the 5' end of the first universal sequence fragment and the second primer binding site fragment is linked at its 5' end to the 3' end of the second universal sequence fragment.

66. The control composition of any one of clauses 49 to 65 wherein the primer binding site fragments range in length from about 15 base pairs to about 30 base pairs.

67. The control composition of any one of clauses 49 to 66 wherein the nucleic acid construct ranges in length from about 80 base pairs to about 300 base pairs.

68. The control composition of any one of clauses 49 to 66 wherein the nucleic acid construct ranges in length from about 80 base pairs to about 250 base pairs.

69. The control composition of any one of clauses 49 to 66 wherein the nucleic acid construct ranges in length from about 80 base pairs to about 200 base pairs.

70. The control composition of any one of clauses 49 to 66 wherein the nucleic acid construct ranges in length from about 80 base pairs to about 160 base pairs.

71. The control composition of any one of clauses 49 to 70 wherein the nucleic acid construct is encapsulated.

72. The control composition of clause 71 wherein the nucleic acid construct is encapsulated in a liposome.

73. The control composition of clause 72 wherein the liposome comprises a lipid selected from the group consisting of cholesterol, a lipopolysaccharide, a peptidoglycan, a PEG, a teichoic acid, a phospholipid, and combinations thereof.

74. The control composition of any one of clauses 49 to 73 wherein the barcode sequence fragment comprises a unique sequence not present in any known genome. 75. The control composition of any one of clauses 49 to 70 wherein the nucleic acid construct is incorporated into the genome of a microorganism.

76. The control composition of any one of clauses 49 to 74 wherein the nucleic acid construct is incorporated into a plasmid.

77. A kit comprising the qPCR control composition of any one of clauses 49 to 76.

78. The kit of clause 77 further comprising a reagent for nucleic acid extraction.

79. The kit of clause 77 or 78 further comprising a reagent for nucleic acid purification.

80. The kit of any one of clauses 77 to 79 further comprising a probe.

81. The kit of clause 80 wherein the probe is a TaqMan probe.

82. The kit of any one of clauses 77 to 81 further comprising a polymerase.

83. The kit of any one of clauses 77 to 82 wherein the kit comprises more than one control composition of any one of clauses 49 to 76 wherein each control composition comprises a different nucleic acid construct wherein the different nucleic acid constructs comprise different barcode sequence fragments.

84. The kit of any one of clauses 77 to 83 wherein the kit comprises more than one control composition of any one of clauses 49 to 76 and wherein the nucleic acid construct in each control composition is encapsulated in a different type of liposome.

85. A method for monitoring sample cross-contamination and/or sample swapping of nucleic acids during qPCR, the method comprising,
  a) extracting DNA from a sample;
  b) purifying the DNA;
  c) spiking the sample, after DNA extraction and purification and before qPCR, with a control composition comprising a nucleic acid construct wherein the nucleic acid construct comprises at least one barcode sequence fragment and at least a first and a second primer binding site fragment, and at least one GC content fragment, and wherein the nucleic acid construct is a deoxyribonucleic acid construct, wherein total DNA is obtained after spiking the sample, and wherein total DNA comprises the DNA from the sample and the DNA from the nucleic acid construct;
  d) performing qPCR on the extracted, purified total DNA; and
  e) detecting the nucleic acid construct in total DNA using a probe.

86. A method for monitoring sample cross-contamination and/or sample swapping of nucleic acids during qPCR, the method comprising,
  a) spiking a sample with a control composition comprising a nucleic acid construct wherein the nucleic acid construct comprises at least one barcode sequence fragment and at least a first and a second primer binding site fragment, and at least one GC content fragment and wherein the nucleic acid construct is a deoxyribonucleic acid construct;
  b) extracting total DNA from the sample wherein total DNA comprises the DNA from the sample and the DNA from the nucleic acid construct;
  c) purifying total DNA;
  d) performing qPCR on the extracted, purified total DNA; and
  e) detecting the nucleic acid construct in total DNA using a probe.

87. The method of clause 86 wherein sample cross-contamination and/or sample swapping can be monitored over all steps of a qPCR protocol including collection of the sample, extraction of total DNA, purification of the extracted total DNA, and qPCR.

88. The method of any one of clauses 85 to 87 wherein the sample is selected from the group consisting of urine, nasal secretions, nasal washes, inner ear fluids, bronchial lavages, bronchial washes, alveolar lavages, spinal fluid, bone marrow aspirates, sputum, pleural fluids, synovial fluids, pericardial fluids, peritoneal fluids, saliva, tears, gastric secretions, a stool sample, reproductive tract secretions, lymph fluid, whole blood, serum, plasma, a tissue sample, a soil sample, a water sample, a food sample, an air sample, a plant sample, an industrial waste sample, a surface wipe sample, a dust sample, a hair sample, an agricultural sample, and an animal sample.

89. The method of any one of clauses 85 to 88 wherein the probe is a TaqMan probe.

90. The method of any one of clauses 85 to 89 wherein one of the GC content fragments has a GC content of about 1 to about 40 percent.

91. The method of any one of clauses 85 to 89 wherein one of the GC content fragments has a GC content of about 40 to about 60 percent.

92. The method of any one of clauses 85 to 89 wherein one of the GC content fragments has a GC content of about 60 to about 100 percent.

93. The method of any one of clauses 85 to 92 wherein the control composition comprises nucleic acid constructs with GC content fragments with at least two different percent GC contents.

94. The method of any one of clauses 85 to 92 wherein the control composition comprises nucleic acid constructs with GC content fragments with at least three different percent GC contents.

95. The method of any one of clauses 85 to 92 wherein the control composition comprises nucleic acid constructs with GC content fragments with at least four different percent GC contents.

96. The method of clause 94 wherein the GC contents are about 1 to about 40 percent, about 40 percent to about 60 percent, and about 60 percent to about 100 percent.

97. The method of any one of clauses 85 to 96 wherein the GC content fragment is used to control for polymerase GC content bias.

98. The method of any one of clauses 93 to 96 wherein at each of the different percent GC contents the nucleic acid constructs comprise the same barcode sequence fragments.

99. The method of any one of clauses 85 to 98 wherein the barcode sequence fragment comprises a unique sequence not present in any known genome.

100. The method of any one of clauses 85 to 99 wherein the nucleic acid construct further comprises at least a first and a second universal sequence fragment.

101. The method of clause 100 wherein the first universal sequence fragment is linked to the 5' end of the barcode sequence fragment, the barcode sequence fragment is between the first universal sequence fragment and the GC content fragment, and the second universal sequence fragment is linked to the 3' end of the GC content fragment.

102. The method of any one of clauses 85 to 101 wherein the nucleic acid construct is amplified.

103. The method of clause 100 or 101 wherein the first primer binding site fragment is linked at its 3' end to the 5' end of the first universal sequence fragment and the second primer binding site fragment is linked at its 5' end to the 3' end of the second universal sequence fragment.
104. The method of any one of clauses 85 to 103 wherein the primer binding site fragments range in length from about 15 base pairs to about 30 base pairs.
105. The method of any one of clauses 85 to 104 wherein the nucleic acid construct ranges in length from about 80 base pairs to about 300 base pairs.
106. The method of any one of clauses 85 to 104 wherein the nucleic acid construct ranges in length from about 80 base pairs to about 250 base pairs.
107. The method of any one of clauses 85 to 104 wherein the nucleic acid construct ranges in length from about 80 base pairs to about 200 base pairs. 108. The method of any one of clauses 85 to 104 wherein the nucleic acid construct ranges in length from about 80 base pairs to about 160 base pairs.
109. The method of any one of clauses 85 to 108 wherein the nucleic acid construct is encapsulated.
110. The method of clause 109 wherein the nucleic acid construct is encapsulated in a liposome.
111. The method of clause 110 wherein the liposome comprises a lipid selected from the group consisting of cholesterol, a lipopolysaccharide, a peptidoglycan, a PEG, a teichoic acid, a phospholipid, and combinations thereof.
112. The method of any one of clauses 85 to 111 wherein more than one type of control composition is used in the method.
113. The method of any one of clauses 85 to 111 wherein more than one type of control composition is used in the method wherein the nucleic acid construct in each type of control composition is encapsulated in a different type of liposome.
114. The method of clause 113 wherein each type of control composition with the nucleic acid construct encapsulated in a different type of liposome comprises a different barcode sequence fragment.
115. The method of any one of clauses 85 to 108 wherein the nucleic acid construct is incorporated into the genome of a microorganism.
116. The method of any one of clauses 85 to 113 wherein the nucleic acid construct is incorporated into a plasmid.

Control compositions for qPCR and methods of their use are provided herein. The quantitative polymerase chain reaction (qPCR) has been developed to analyze nucleic acids in a laboratory. qPCR for quantitation of nucleic acids is a powerful technique, for example, for pathogen detection and quantitation, including for biosurveillance and disease diagnosis. However, the field suffers from a lack of standards for use in qPCR methods and devices that can be used to monitor cross-contamination and sample-swapping. Currently, researchers are able to detect and identify nucleic acids from, for example, pathogens using qPCR, but are unable to monitor sample cross-contamination and sample swapping throughout the qPCR protocol. More effective standards are also needed for monitoring sample cross-contamination and sample swapping in a qPCR protocol after the extraction process.

In one embodiment, control compositions for qPCR are provided. The control compositions comprise a nucleic acid construct comprising at least one barcode sequence fragment and at least a first and a second primer binding site fragment. The barcode sequence fragment comprises a unique sequence not found in any known genome. In one embodiment, the control composition is used to determine if cross-contamination between samples for qPCR has occurred. In another embodiment, the control composition is used to determine if sample swapping during qPCR has occurred. In one aspect, the nucleic acid construct is a deoxyribonucleic acid construct. In another aspect, the nucleic acid construct is a ribonucleic acid. In another embodiment, the nucleic acid construct is incorporated into a plasmid. In yet another aspect, the nucleic acid construct is incorporated into the genome of an organism.

In various embodiments, the barcode sequence fragment can be from about 10 to about 35 base pairs in length, about 10 to about 34 base pairs in length, about 10 to about 33 base pairs in length, about 10 to about 32 base pairs in length, about 10 to about 31 base pairs in length, about 10 to about 30 base pairs in length, about 10 to about 29 base pairs in length, about 10 to about 28 base pairs in length, about 10 to about 27 base pairs in length, about 10 to about 26 base pairs in length, about 10 to about 25 base pairs in length, about 10 to about 24 base pairs in length, about 10 to about 15 base pairs in length, about 21 to about 28 base pairs in length, about 21 to about 27 base pairs in length, about 21 to about 26 base pairs in length, about 21 to about 25 base pairs in length, about 22 to about 28 base pairs in length, about 22 to about 27 base pairs in length, about 22 to about 26 base pairs in length, about 22 to about 25 base pairs in length, about 23 to 25 base pairs in length, or about 24 base pairs in length.

Various embodiments of barcode sequence fragments are shown below in Table 1 (labeled barcode sequence fragments). These barcode sequence fragments can be used alone or in combinations of, for example, two or more barcode sequence fragments. Additional barcode sequence fragments are shown in Table 2 between the bolded fragments and within the exemplary nucleic acid constructs having SEQ ID NOS:1 to 384.

TABLE 1

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| TGGTCAACGATA | CATCGCGTTGAC | ACGTAACCACGT | CTTCTTCGCCCT | GACGGCTATGTT | GTCATTGGGCTA |
| ATCGCACAGTAA | GCACATAGTCGT | GTCGGAAATTGT | CAGGCATAACAT | TCTCTTTCGACA | AGAGACGCGTAG |
| GTCGTGTAGCCT | GGCAAATACACT | TCTAACGAGTGC | ATGTGGCGTGTT | GATTAGGTTCCG | TTAATGGATCGG |
| AGCGGAGGTTAG | GTCATGCTCCAG | CATCTGGGCAAT | GTGCGGTTCACT | CTACTCCACGAG | ATATTGGCAGCC |
| ATCCTTTGGTTC | CCTAGTAAGCTG | TGTCCGTGGATC | CCTCACTAGCGA | GGTGCAGACAGA | TCGCATGGATAC |
| TACAGCGCATAC | TTACCGACGAGT | ACTCGGCCAACT | AGCTGATAGTTG | CCGTACCGTATG | CAACAATGCCAA |

TABLE 1-continued

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| ACCGGTATGTAC | GCTTAGATGTAG | GTTGGTTGGCAT | GCTCTAGTAACG | ATGTCCGACCAA | GCCCGACATATA |
| AATTGTGTCGGA | AAGACGTAGCGG | TTCCACACGTGG | TGGTCCTACAAG | AGATGGGACTGG | GATTGAACGCTA |
| TGCATACACTGG | TTACCTTACACC | AACCCAGATGAT | CGCTATCCAGAC | GTGCCCACTTGA | AGTATTCGCGCA |
| AGTCGAACGAGG | TGACTAATGGCC | GTAGTGTCAACA | GCTTACGTAGGT | ACCGAACAATCC | TGCCAACAACAA |
| ACCAGTGACTCA | CTCTCTCACTTG | TGGAGAGGAGAT | AGTTGGTTACGA | GTCTACCACGCA | CTAAAGTAGCAC |
| GAATACCAAGTC | ATTGCAAGCAAC | CGTATAAATGCG | CTCTACGAACAG | TCGCGTCCAGTA | AGTGCTAGGTTA |
| GTAGATCGTGTA | CACGTGACATGT | AATACAGACCTG | CCTGTGTTGGTG | GCCTGATTAAGC | CGGAAACTCCAT |
| TAACGTGTGTGC | CACAGTTGAAGT | GACTCAACCAGT | GATGGGAGGACT | ACGTATTCGAAG | AGGAAAGCCAGA |
| CATTATGGCGTG | CTAGGATCACTG | GGAAGAAGTAGC | CAGAATCGCTCA | CGGCTACTATGC | GTCTGACGGTCT |
| CCAATACGCCTG | GATGACCCAAAT | ATCGATCCACAG | TGGCACTGGTTA | AGTTCGGCATTG | GAAACCAAGCTT |
| GATCTGCGATCC | ACCGGAGTAGGA | ACACCGCACAAT | GGCAGTGTTAAT | TTGGGAGCGAAG | TCATCACGGGCT |
| CAGCTCATCAGC | TGAGGACTACCT | GTCTCCTCCCTT | AACCCGTCGTCA | TGTTCGCCCAGA | TGTTCTGAGACG |
| CAAACAACAGCT | CAATCGGCTTGC | GTAGCACTCATG | AGAGGAGTCGAC | CGCGTATCTCAG | ATAGCACCAGAT |
| GCAACACCATCC | AACACTCGATCG | CACCTGTAGTAG | TAAGTCGGCCTA | CGAAAGCATTCC | ATCTCGCTGGGT |
| GCGATATATCGC | TGACCGGCTGTT | CACGAGCTACTC | CAGGGTAGGGTA | CCGGACAAGAAG | GCGCGTGTATCT |
| CGAGCAATCCTA | GGAGGAGCAATA | TCTCGATAAGCG | CATGGGTGTTAC | CGATCCGATCTG | AACGCGAAATTC |
| AGTCGTGCACAT | AGCGACGAAGAC | TAGACACCGTGT | GATGCCTAATGA | TGCATCGCGTCA | ATCTGGACGATC |
| GTATCTGCGCGT | CTTCCCTAACTC | AGACAAGCTTCC | TTATCGGGCATG | ATGGACCTAGCT | CCAGCTGGACTT |
| CGAGGGAAAGTC | TGGAAGAACGGC | TCCGCAACCTGA | TGGACATAAACC | AGGAATACTCAC | CTCTAACCTCTA |
| CAAATTCGGAT | GCTAGACACTAC | TCACTTGGTGCG | TGACCTCAAGAC | CTACCTTGAGGA | CAACCGAGATTA |
| AGATTGACCAAC | TTGGATTGAACG | TTATGTACGGCG | GCCAAATCGCTC | CGTGTTATGTGG | GATTCGAGTGTC |
| AGTTACGAGCTA | GATATACCAGTG | TTGGACGTCCAC | TCAAAGCTCAAG | GTACGCACAGTT | GGTAACCTCTGA |
| GCATATGCACTG | AACAAACTGCCA | TCCAGGGCTATA | TACCAATCGGTG | TGGACTCAGCTA | AGCGAACCTGTT |
| CAACTCCCGTGA | GTAGACATGTGT | GCGTAGAGAGAC | GTACTCGAACCA | ACGCGCTAAATC | ACATGCACATGC |
| TTGCGTTAGCAG | TACAGTTACGCG | GAAACTCCTAGA | TTCCGGCGATTG | GACCTGAATACA | CCTTACCTCCTC |
| TACGAGCCCTAA | CAAGCCCTAGTA | ATCGGGCTTAAC | GACATGCGGAGA | ACGTTTGTGGCA | ACACTGGTCCTG |
| CACTACGCTAGA | TAGTGTCGGATC | TACGCCCATCAG | CGCACCCATACA | GCTTAACGTGCC | AGCTTGAATCAG |
| TGCAGTCCTCGA | CTGAGCTCTGCA | AAGATCGTACTG | ACATTGAAGCGT | GAATGGATGGGC | TAAAGCGAGGAG |
| ACCATAGCTCCG | CTTCGACTTTCC | ACTCATCTTCCA | GACGACATTTAG | CATGAACAGTGT | CGACAACTTGTG |
| TCGACATCTCTT | GTCATAAGAACC | GAGATACAGTTC | CCAACTACTCGG | GACTAGTCAGCT | CGCTGGCTTTAG |
| GAACACTTTGGA | GTCCGCAAGTTA | GCATGCATCCCA | CCGTTATCAGCG | CAAGAAATTCGC | GTGATACCCGCT |
| GAGCCATCTGTA | CGTAGAGCTCTC | GATCTAATCGAG | TATGGCCAAACC | AAGCTCTCCCAG | CCAGTTCCAAAG |
| TTGGGTACACGT | CCTCTGAGAGCT | AATCTTGCGCCG | TGCCTAAGATCG | TGGATCTGTCCG | GTCTGGATTGAA |
| AAGGCGCTCCTT | CCTCGATGCAGT | GGAAATCCCATC | TTAACTGGAAGC | CCTACTCGGTGA | GCGCAATAGTAT |
| TAATACGGATCG | GCGGACTATTCA | GACCGTCAATAC | ATTCGAGCTGTG | ATACCGTCTTTC | AGCGTTGTCCAA |
| TCGGAATTAGAC | CGTGCACAATTG | TTGGAACGGCTT | GGTCTGTTGAGT | AAGGACCGTTTC | CGCCTAAACCGT |
| TGTGAATTCGGA | CGGCCTAAGTTC | TCCTAGGTCCGA | CTCGTCGACTGA | AAGTAGGAAGGA | AACACCATCGAC |
| CATTCGTGGCGT | AGCGCTCACATC | TCCTCACTATCA | TCTTTCATACCG | CGTGCCGCTTAA | CTATAGACACGA |

TABLE 1-continued

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| TACTACGTGGCC | TGGTTATGGCAC | GCCTGCAGTACT | CATTCCCGAAAG | GCGTCATGCATC | CAAGAGCGGATG |
| GGCCAGTTCCTA | CGAGGTTCTGAT | GCCCAAGTTCAC | TTGTCAGCTGGA | CGTTGGACAAAT | CCTTTGGCTGAG |
| GATGTTCGCTAG | AACTCCTGTGGA | ATAAAGAGGAGG | ATCTGCGCACCA | TTGTTGATGGAG | CGACCCATACGT |
| CTATCTCCTGTC | TAATGGTCGTAG | GCGCCGAATCTT | CCACGTACGTAA | CTTACACTGCTT | CTGGATTACGGT |
| ACTCACAGGAAT | TTGCACCGTCGA | ATCCCAGCATGC | ACGATATGGTCA | AATGCGCGTATA | ACCACACGTAGT |
| ATGATGAGCCTC | TGCTACAGACGT | GCTTCCAGACAA | GAGACAGTGGAA | TGCCATTAGAGC | CTAGTGACCTAG |
| GTCGACAGAGGA | ATGGCCTGACTA | ACACAGTCCTGA | TCGTAGTAATGG | CGAAGGGTTGGA | GGATTCGTGTCC |
| TGTCGCAAATAG | ACGCACATACAA | ATTATACGGCGC | AGGCTGTACTCC | GAGCAACATCCT | GTGAGATACCTA |
| CATCCCTCTACT | TGAGTGGTCTGT | ATTCAGATGGCA | CGGAAGAGAACA | TCGTGTTGTGGC | CGCGGTTACTAA |
| TATACCGCTGCG | GATAGCACTCGT | TAAACGCGACTC | CTGCGGATATAC | ATTTCGACCCGG | AGGCCCGTTTAC |
| AGTTGAGGCATT | TAGCGCGAACTT | CCTCGGGTACTA | CTAGCGTGCGTT | TGGATTGTGAAC | TGTTGTTGGGAA |
| ACAATAGACACC | CATACACGCACC | TTCACCTGTATC | ACCATGTAGAAC | CCGTTGGACTAC | CTGAATCTGGTG |
| CGGTCAATTGAC | ACCTCAGTCAAG | CTCCAGGTCATG | TAGCTCACAGCA | TCTGGCTACGAC | GGCCTCACTGAT |
| GTGGAGTCTCAT | TCGACCAAACAC | CAGGATTCGTAC | GTCTTGGGTCGT | TCAGGCGTAAAT | GTGGTTCGATGT |
| GCTCGAAGATTC | CCACCCAGTAAC | CGCATACGACCT | CTGTATGGAGCT | TCACGGTGACAT | TCGAGAGTTTGC |
| AGGCTTACGTGT | ATATCGCGATGA | GCCTCGTACTGA | ATGCAACTCGAA | CAAGGTCACCTC | TACGACTCTGGC |
| TCTCTACCACTC | CGCCGGTAATCT | ACCAACAGATTG | CTAACTGACGCA | CTATACGCGAAC | GCGTAACTCTCG |
| ACTTCCAACTTC | CCGATGCCTTGA | GTGGCCTACTAC | AACGTCCTGTGC | GAGGAGTAAAGC | CTTTCCCTTCGA |
| CTCACCTAGGAA | AGCAGGCACGAA | TTCCCTTCTCCG | AGACGACGTGGA | GCAGCATGTTAA | AAGATTTGCAGC |
| GTGTTGTCGTGC | TACGCAGCACTA | CATTTGACGACG | AAGGTTCCGATA | GTTGGGATCCTC | AACGGCTGGAAG |
| CCACAGATCGAT | CGCTTAGTGCTG | AAGTGAAGCGAG | AGTTTCTGGTGG | TTCAGCGATGGT | ATCGTCCGCGAT |
| TATCGACACAAG | CAAAGTTTGCGA | TGCCGCCGTAAT | TTCCTCCTGCTA | ACAATCCCGAGT | TCACAGACAATG |
| GATTCCGGCTCA | TCGAGCCGATCT | AACCTCGGATAA | CATCTCAGTCGG | GTTCTTGGAGAC | GAGACTATATGC |
| CGTAATTGCCGC | CTCATCATGTTC | GTGCTTGTGTAG | ATATGCGAGACT | TAGCCCTGATGC | AGAGGGTGATCG |
| GGTGACTAGTTC | CCAGGGACTTCT | CAACTAGACTCG | GACCACTGCTGT | TTGTCCCAAGCG | TAGAGAATGCTC |
| ATGGGTTCCGTC | GCAATCCTTGCG | AGTGCCCTTGGT | ATAGACACTCCG | TTCGTACTTCGT | AGAGCATCCACT |
| TAGGCATGCTTG | CCTGCTTCCTTC | GGAACGACGTGA | GAATCGCCGATT | CTGCTCAGGCAT | ACAGTCTGCATG |
| AACTAGTTCAGG | CAAGGCACAAGG | TGTCAGCTGTCG | TAGAAGGCTCCT | GACATCTGCACC | AATCGGTCCGAT |
| ATTCTGCCGAAG | GGCCTATAAGTC | CTGGTGCTGAAT | CGACTAACTAGA | CACAACCACAAC | CCGTTCAATGGA |
| AGCATGTCCCGT | TCCATTTCATGC | GACAGAGGTGCA | TACAACCGAGTA | GCACCAATCTGC | CTCTCGGCGTAA |
| GTACGATATGAC | TCGGCGATCATC | TCAGACCAACTG | CTCATGGTAGCA | ATTAGCAGCGTA | TCCCTCTGAGAG |
| GTGGTGGTTTCC | GTTTCACGCGAA | AGTGATGTGACT | AACGACACGCTT | TCCGATAATCGG | AAGTTAGTCCGC |
| TAGTATGCGCAA | ACAAGAACCTTG | CTTAGCTACTCT | CCTGGCTGAATA | CTTTCAGGACCG | TCAGATACCAGC |
| TGCGCTGAATGT | TACTCTCTTAGC | TCGGTCCATAGC | TTCGGATGTGAA | CGTCCTACAGTG | TCGAAGACGTAT |
| ATGGCTGTCAGT | AACTGTTCGCGC | CACGTTTATTCC | CTAGGTCCGACT | GTAACTCAACAG | CACTTCTTTGTG |
| GTTCTCTTCTCG | CGAAGCATCTAC | GAAACGGAAACG | AGATCCCGTACC | CGTGGAAGACGA | CGTCGATTGCAC |
| CGTAAGATGCCT | GTTTGGCCACAC | GGTCGTGTCTTG | TCTGGTGCATCG | GAGAGGGATCAC | GTTGCCTCTGAG |
| GCGTTCTAGCTG | TCAGGTTGCCCA | CGTCGTCTAAGA | CAGCTGGTTCAA | TCGGCTTGGAAT | CACCTCCAAGGT |

TABLE 1-continued

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| GTTGTTCTGGGA | TCATTCCACTCA | CAAGCGTTGTCC | GCTGGATTGTCA | TGAACAGGTTCA | GTAAGCCTCGAT |
| GGACTTCCAGCT | GTCACATCACGA | GACTTATGCCCG | TCTTGTTTCTGG | GAGAGATCGACG | CTCCGCTATAGG |
| CTCACAACCGTG | CGACATTTCTCT | GTGACGTTAGTC | TTGAACAAGCCA | ATACAAACGCAC | ACTGCTATCGCG |
| CTGCTATTCCTC | GGACGTTAACTA | GAGTCTTGGTAA | CCAGGTTAATGC | GATTCACTGTGG | ACCACTTGCCAG |
| ATGTCACCGCTG | TAGCAGTTGCGT | TCGTCGCCAAAC | ATTCGTACCTCT | GCTTGCCAATCG | ACCAGAAATGTC |
| TGTAACGCCGAT | CACGCTATTGGA | AACATGCATGCC | TAGCGTTCCAGA | CTGACACGAATA | ATGCTTGCTCTT |
| AGCAGAACATCT | AACTTCACTTCC | GTCTGTTGAGTG | CCAGAAGTGTTC | GTTCTAAGGTGA | ACAGTTGTACGC |
| TGGAGTAGGTGG | CCAGTGGATATA | TGAGTTCGGTCC | ACGATCATCTGG | CGTGAATCAACC | AGCTACTGCGTC |
| TTGGCTCTATTC | TGTGTGTAACGC | TTACGTGGCGAT | ACTGTACATGAG | GAGCTAAGTTAC | ACTGCCCGATAC |
| GATCCCACGTAC | CCAATCGTGCAA | CAATGCCTCACG | TGCCCGGACTTA | AGCGATTCCTCG | CACAGCGTCCTA |
| TACCGCTTCTTC | AGGCTAGCAGAG | TGTACGGATAAC | ATCCCGTACGTG | CCAACCCAGATC | ACGTCCACTGTG |
| TGTGCGATAACA | GTCACTCCGAAC | AATCAACTAGGC | CTTGTTGTTCTG | GATTGCTACCAG | CGCTAATCGTGA |
| GATTATCGACGA | CACCGAAATCTG | GTGAGGGCAAGT | TGACAGAATCCA | GGCTCTAACGTA | GGCCGTTCGATT |
| GCCTAGCCCAAT | TGACGTAGAACT | CGTGGGCTCATT | CACTGTATGAAG | AATCTGCACCGA | GGAACTTACTCG |
| GATGTATGTGGT | CTATGCCGGCTA | CGTACCAGATCC | TGGATGCGCATT | CCAGCCTTCAGA | CAGTTACCCAAG |
| ACTCCTTGTGTT | GTGGTATGGGAG | ATGTTTAGACGG | GCCCATATCAGA | CCGTGTTAGACA | GAGGGACGCAAT |
| GTCACGGACATT | TGTACCAACCGA | ACATGTCACGTG | CGTGTGTGCTCA | ACCTCTATTCGT | TAGGCCATGTAA |
| GCGAGCGAAGTA | AGGGTACAGGGT | CTTTAGCGCTGG | ATCCATGAGCGT | GGCAAGGCACAA | AACCGTCGCCTA |
| ATCTACCGAAGC | AGAGTGCTAATC | CTGGTCTTACGG | TAGACTTCAGAG | GCCATTATAGAG | TTACGAAGTTGG |
| ACTTGGTGTAAG | TTGGCGGGTTAT | CAAGTCGAATAC | TGATTCCCGGTG | TAACCGAACCAC | AGATAGCTCGCT |
| TCTTGGAGGTCA | CACGATGGTCAT | GCAAGTGTGAGG | AGTTCCACGGCT | GGTGCGTCACTT | CTGGTTGGCATC |
| TCACCTCCTTGT | GTCACCAATCCG | CTCGGTCAACCA | GGAAGCTTAACT | TGTGCTTGTAGG | CTGCTTCTTACA |
| GCACACCTGATA | CACTAACAAACG | ACCCTATTGCGG | GGAGACGTTCTT | TGACTCTGCGGT | GTTCGAGTGAAT |
| GCGACAATTACA | TTCCAGGCAGAT | TCCGTTCGTTTA | ATTGCGCTACCG | GTACACTGATAG | TTCTTCTACCGC |
| TCATGCTCCATT | TATGGTACCCAG | ACCACCGTAACC | CCGACCAGCTTA | TTACATCCCTTG | TCTCTCGATCAT |
| AGCTGTCAAGCT | CACGACTTGACA | CATTTCGCACTT | CAATCCACCGAA | GGTGTGAGAAAG | AATCCATGACAG |
| GAGAGCAACAGA | CTTGGAGGCTTA | TTAAGCGCCTGA | TACGCGTACAGT | CTCTTTGTCGAT | GGTATTCAAAGC |
| TACTCGGGAACT | ACGTGGTTCCAC | TGCGGGATTCAT | CCGTCAAGATGT | GTGAACTGGATT | GGTCCACCTAAC |
| CGTGCTTAGGCT | GACGCTTTGCTG | CAAACTGCGTTG | TACACGCTGATG | CCTAACGGTCCA | TGATCACTCTTC |
| TACCGAAGGTAT | ACAGGGTTTGTA | TTAGACTCGGAA | CGTTTCAAGGAC | TGTAGCCGCTTG | GGCACGAAAGGT |
| CACTCATCATTC | GCCTATGAGATC | GACCGATAGGGA | GCAGAACTTAGT | TACCCGACTAAG | CATGAGACTGTA |
| GTATTTCGGACG | CAAACCTATGGC | GGCGAACTGAAG | ACCCGTTGATGA | CGTAGTACCACA | GGTCATCACGAT |
| TATCTATCCTGC | ATCGCTTAAGGC | CGGCACTATCAC | GACGTAGAACGG | CGGAGAGACATG | AGTCTAGAGTAC |
| TTGCCAAGAGTC | ACCATCCAACGA | AGGTGGTGGAGT | CGGTACCTACCA | CCAAAGCCAGTT | TGCGCAAAGGAG |
| AGTAGCGGAAGA | GCAATAGGAGGA | ATTCCCAGAACG | GCGTTTGCTAGC | TACGATGAGTTG | GGTTTGCACATG |
| GCAATTAGGTAC | CCGAACGTCACT | AGACGTTGCTAC | AGAAACAGCTCT | GCTTGGTAGGTT | TGGGTTAACACA |
| CATACCGTGAGT | ACACCAACACCA | AGAATAGCGCTT | CTCAGACTCAGA | CCGGAATCCATA | TAGGTTGCTTGG |
| ATGTGTGTAGAC | CCATCACATAGG | AAGCGTACATTG | CCGAGTACAATC | ATCGGCTTCCGA | CAGGAACCAGGA |

TABLE 1-continued

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| CCTGCGAAGTAT | CGACACGGAGAA | GTTATGACGGAT | GATATGAACTGC | CACTAGACCCAC | TGCTCGATGTGC |
| TTCTCTCGACAT | GAACCTATGACA | AGCCTCATGATG | GCAGTCTAAGAT | GGAAAGGAGAAT | AGGTTTGGCTTG |
| GCTCTCCGTAGA | ATGCCGGTAATA | GTGTATCGCCAC | CGGCGCATTATA | GAGTATCTGAGT | TACTCCAGGCTG |
| GTTAAGCTGACC | GAACAGCTCTAC | CCAAACTCGTCG | GGTGCTAATCAC | CTCGCTAGATAG | TTCGGCATAGTG |
| ATGCCATGCCGT | GTGAGTCATACC | ACGTGAGGAACG | CGTTTGGAATGA | CCAGGACAGGAA | GTGCCATAATCG |
| GACATTGTCACG | TGGCCGTTACTG | TGAATCGAAGCT | GGTTAGAGCGGA | AAGGGTTAGTCT | TGCAGATCCAAC |
| GCCAACAACCAT | TAGAGCTGCCAT | CTGCAGTAAGTA | GTAGTAGACCAT | GTGACTAGTGAT | TCACTCTTGTAC |
| ATCAGTACTAGG | ATCTAGTGGCAA | TATAGGCTCCGC | ATCAAGATACGC | GGCCTTCAGTCA | TGGTGGAGTTTC |
| TCCTCGAGCGAT | CCTTCAATGGGA | ATCGTGTGTTGG | TCTATCTGGCTT | ACACGTTTGGGT | AGAACACGGAAG |
| ACCCAAGCGTTA | TTGACGACATCG | CTTCCGCAGACA | GGAAACAAACGG | CGAACGTCTATG | TCGAAACATGCA |
| TGCAGCAAGATT | ACATACTGAGCA | GCACTATACGCA | GATTGGCATAGT | TCATGTGAACGA | AACTAAGGACTC |
| AGCAACATTGCA | GGCTAAACTATG | TCTGGGCATTGA | GAGTTGTACGAT | TCTCCGTTCCCT | AACTCAATAGCG |
| GATGTGGTGTTA | AAGAGCAGAGCC | CCAATGATAAGC | CTCGAAATGCAA | CTGATTACGAGA | CTTAGAACGTGC |
| CAGAAATGTGTC | GGAGAGATCACG | TTAAACCGCGCC | AGAAGAAAGGCA | TCTGAATGGTAG | CCGTATATGCGC |
| GTAGAGGTAGAG | TCAACCCGTGAA | CTTGCATACCGG | CCACTCTCTCTA | CATCGTTGGTCG | TATGACGTACGA |
| CGTGATCCGCTA | GTTTGAAACACG | GTGCACGATAAT | CCTCCTAATTCA | TAGATCCTCGGA | TCTCTGAACAGG |
| GGTTATTTGGCG | AGAGAGACAGGT | GGTCTAGGTCTA | TTCATGGCCAGC | TCGGACAGTGTT | CCTTTATAGTCC |
| GGATCGTAATAC | TCGCCAGTGCAT | TCAGGACGTATC | ATTGGACACGCT | TGATGTGCTAAG | TGTAGGTGTGCT |
| GCATAGCATCAA | GCTCAGGACTCT | GAAAGGTGAGAA | AATTCACCTCCT | CAGTAAATCGCA | TCCCACGAAACA |
| GTGTTAGATGTG | CACTTTGGGTGC | GAATATACCTGG | ATGAAGCACTGT | CAAGTTTCCGCG | TACGCTACGACC |
| TTAGAGCCATGC | TCTAGCCTGGCA | GTCGCTTGCACA | TTGATGTGAGGT | ACATCGTTGACG | GTCAGTATGGCT |
| TGAACCCTATGG | AATGCAATGCGT | TCTACCACGAAG | TCTTGCGGAGTC | ACGAAAGAGCAG | CCATATCCCGGA |
| AGAGTCTTGCCA | CGAATGAGTCAT | AATATCGGGATC | TTAGTCGTGACG | TGATGAACCCGT | TCGTACCAGGAT |
| ACAACACTCCGA | CAACGCTAGAAT | TAGTGCATTCGG | TGCCAGACCACT | GCTCTTATGCTT | AGTGACTGTCAA |
| CGATGCTGTTGA | ATCAGAGCCCAT | TCAATGACCGCA | AGGCTCCATGTA | CGACCTCGCATA | GGTGAGCAAGCA |
| ACGACTGCATAA | TCTGTAGAGCCA | CTATCGGAAGAT | ACTACTGAGGAT | CTAATTCTCTGC | AGTTCATACGGC |
| ACGCGAACTAAT | CCGACTCTAGGT | CGGATTGCTGTA | TATCTGGAAGTG | GGAAGTGGCCAA | TCGCTTTAACCT |
| AGCTATGTATGG | ATCCTACGAGCA | GGTACTGTACCA | CAGCTATGGACT | GATAATGTGCAC | GGCTTACTTGGA |
| ACGGGTCATCAT | GACAACGAATCT | ATCGAATCGAGT | TTGCTGGACGCT | CTCTGAGGTAAC | CCATCCGCAACA |
| GAAACATCCCAC | TGCGGTTGACTC | CTAGCAGTATGA | CTACTAGCGGTA | ATTTGCTTTGCC | CGCAATGAGGGA |
| CGTACTCTCGAG | TGAGAAGAAAGG | GTTAATGGCAGT | TACAGGACGGGA | TACTGGTAAGAC | GCTACAAGCCCT |
| TCAGTTCTCGTT | TCGGATCTGTGA | GTATGGAGCTAT | CTCAGGAGACTT | TTGAGAAGCACT | ATTGAAGTCTGG |
| TCGTGCGTGTTG | GCCGGTACTCTA | CCTTCTGTATAC | TCGTTGGGACTA | ATAACGGTGTAC | GGATTACGCTGT |
| GTTATCGCATGG | CACAGGATTACC | ACGCTGTCGGTT | GTCCATGGTTCG | TCCCGTAGCATG | CAGCAGTCTTCG |
| GATCACGAGAGG | CGATATCAGTAG | CTCGTTTCAGTT | TGGCATGTTGGT | CAGATGTCGCTA | CGTAGCCAACAT |
| GTAAATTCAGGC | CATAAGGGAGGC | GCGAACCTATAC | AATCGTAAGGTC | TGAGCAACATAC | ATACAGCATACG |
| AGTGTTTCGGAC | TGTGTTACTCCT | CTCTCATATGCT | CTTACGAGTAGA | GGTTCATGAACA | CTGAGTGAGTAT |
| ACACGCGGTTTA | GGTACCTGCAAT | CCAGTATCGCGT | CAACTGTCAGAC | GAGCGAGTTAGG | GCTTGTACCGAC |

TABLE 1-continued

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| TGGCAAATCTAG | TCGCCTATAAGG | TCGTTTCTTCAG | TGACTGCGTTAG | GCTCAATCAGAA | CGCTAGGATGTT |
| CACCTTACCTTA | AGTGGCACTATC | AGTACCTAAGTG | GGCTGATGTCAT | GACCATGTAGTA | GGACAAGTGCGA |
| TTAACCTTCCTG | TAACCCGATAGA | GGATGCAGGATG | TGTCCAGTTCGG | CACACGCCTGAT | GTTCGTATACGG |
| TGCCGTATGCCA | GTGTGCTAACGT | CCACTTGAGAGT | ACTCGTGATAGC | TCTTCGCAGCAG | CGGGTAGGGTAA |
| CGTGACAATAGT | CTTGCGGCAATC | GCACTTCATTTC | GCCCTCAAATGC | TCTCATGTGGAG | ATGCGCCCGTAT |
| CGCTACAACTCG | TGAGGTTTGATG | AGAATCCACCAC | TAAATCACGCGC | TTCCATCATGTC | CTGTCGTGTCAG |
| TTAAGACAGTCG | ATTGCTGGTCGA | CTCAAGTCAAAG | GGCGTGCATTAT | GTCCTACACAGC | ACGGTGAAAGCG |
| TCTGCACTGAGC | AAGAAGCCGGAC | GTACCTAGCCTG | GGTCAATATTGG | GAGGTGGGAGTT | TCACGTATTCTC |
| CGCAGATTAGTA | ACGGGATACAGG | CACTGAGTACGT | AGGTTCTTAGGC | TGGCCTAGTCAA | GAAGGTGAAGGT |
| TGGGTCCCACAT | AAGAGTCTCTAG | TCAAGCAATACG | TAGGTGCAATCA | TCCTTCCCTGCT | CACATGGGTTTG |
| CACTGGTGCATA | TCCGTCATGGGT | CATGTTGGAACA | GTCCAAAGCGTT | CTCACTGCTTCT | TAGGTAACCGAT |
| AACGTAGGCTCT | AGATCTATGCAG | ATGGGACCTTCA | AGATCGTGCCTA | TAGGAGAGACAG | GGTCGAATTGCT |
| AGTTGTAGTCCG | GCACAAGGCAAG | GCTATTCCTCAT | CTCCTCCCTTAC | TGTTCCTCTCAC | TGTAAACAGGTC |
| TCGTCAAACCCG | CGGCAAACACTT | GTCTCTGAAAGA | GAGCATTACATG | GCGTTAACCCAA | GTTACGTGGTTG |
| TAATCGGTGCCA | GCGAGTTCCTGT | GTTCTGCTTGTT | AAGCACGTCTCA | CCACACGTTTGG | AGGATCAGGGAA |
| TTGATCCGGTAG | TTCCGAATCGGC | GTCAAGACCTCA | TAGGGAGACCGA | ACAGCATAGCTC | TAGGACGGGAGT |
| CGGGTGTTTGCT | TACCTAGTGAGA | TTGTTACGTTCC | ATAAGCCCAATG | AATGTGGCTCAC | GCAACGAACGAG |
| TTGACCGCGGTT | CGTTCTGGTGGT | CAGTTCGAGATA | ACGTGCCTTAGA | GAGTTCCATTGG | TGACGGTTTAGC |
| GTGCAACCAATC | TTGGTCTCCTCT | AATGTCACCAGA | TCCTGCTATCTA | TCTGATCGAGGT | AAGTGTGGTTGT |
| GCTTGAGCTTGA | CTGCATACTGAG | CAGCCTGCAAAT | CACGAAAGCAGG | CAAGTGAAGGGA | CTTCGTTTCGTA |
| CGCTGTGGATTA | CAGGGCCTTTGT | TTGCAAGTACCG | TCAAGTCCGCAC | TGCCCATCAGGT | CACCGCTCACAA |
| CTGTCAGTGACC | CGATGAATATCG | GCTTCTCTCACT | TAGCACCTAAAG | AGGTTGCTGTAA | CTGAACAGTTGC |
| ACGATTCGAGTC | GTCAATTAGTGG | CGAGATAGTTTG | GTTTCTTGTTGC | TAAGTACTGCAG | CGCTCTTAACGG |
| GGTTCGGTCCAT | AGTACGCAGTCT | CGCGTCAAACTA | ACCTAAAGCTGC | GCCGATTGTAAC | GGAGTCTCTTGC |
| CTGATCCATCTT | AGCAGCTATTGC | TTGACACACGAC | ACCACGATGCTA | CGGTGGAAGCAA | AAGTTCCGGCCT |
| TATGTGCCGGCT | CTCGGATAGATC | ATAAGGTCGCCT | GCATCTAAAGCC | GTTGAAGCACCT | GCGCTGTTTAAG |
| TGGTCGCATCGT | TTCCCGAAACGA | TTGCCCTTTGAT | CGTTGACACCCA | TGTCTTTACCTG | GACAATTCCGAA |
| TGTAAGACTTGG | GAACTTTAGCGC | CCTGGAATTAAG | CTTGGGTTAGGT | CCTTGTTCACCT | AGGTCTCCCGAT |
| CGGATCTAGTGT | TCCTTAGAAGGC | TGAGACCCTACA | CTACGTGAAATG | CAACCACTCGGT | ACGATGGTTGAT |
| CGATCTTCGAGC | GATGGACTTCAA | AAGTATCCTGCG | GCCAGCTTCATG | TCTTAGTCGGGC | AGACTTCTCAGG |
| GTCGAATTTGCG | TACTGAGCCTCG | CAAATGGTCGTC | GTGCATTCGCCA | GTACCGTTGCAA | GGATGTCTTCGC |
| GCATCAGAGTTA | AGAAGGCCTTAT | ACACATAAGTCG | TGAGAGTCCCTC | CTGATAGCACAC | TCCTGAACACAG |
| GTGGTCATCGTA | TGGAGCCTTGTC | TACTGCCAGTGA | CTCTGTAGCCGA | ACAGGTAGAGAG | AAGCCTCTACGA |
| CTGAAGGGCGAA | CTCGATGTAAGC | GAGTTTACGGTC | GCAGTAACTGTC | TGCTCACGTGTG | TACTTGCCACGG |
| CGCTCACAGAAT | AGCTTCGACAGT | GGCACACCCTTA | CATATAGCCCGA | GTAATAATGCCG | GCATAAACGACT |
| ATTCGGTAGTGC | ATACGCATCAAG | GTCCAGCTATGA | CAGTGCACGTCT | TCCGGCACCAAT | CTTTGCACTTTG |
| CGAGCTGTTACC | AGATGTCCGTCA | TCGCGCAACTGT | CAAGACTGACCT | ACTCGAAACCAA | TGACACGACATC |
| CAACACATGCTG | GCACCTGTTGAA | ATTCCTCTCCAC | CCGATAAAGGTT | ACCGTAAGACAT | TGTTGACGATGC |

TABLE 1-continued

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| ATTCTCTCACGT | CCTAGAGAAACT | TGGTTCATCCTT | CTTTGTCAGGGC | ATCACGGGAGAG | GACAAGAAGGTG |
| CGACTCTAAACG | GAGGTTCTTGAC | AGCACTTTGAGA | TCCGAAGACAAT | TCACTGCTAGGA | GAGTGCTCTAAC |
| GTCTTCAGCAAG | CTGTAAAGGTTG | CCACGGTACTTG | ACTTCGGATGCA | CTAATCAGAGTG | TTGTGTCTCCCT |
| CGGATAACCTCC | TGAGTCATTGAG | ACTAGTTGGACC | TAACATCAGGCA | TTGGCATTGGCA | CGTTACCGGACT |
| AGGGTGACTTTA | TACGGCAGTTCA | GATCAACCCACA | TAATGAGATGCC | TATAATCCGAGG | TGTGCACGCCAT |
| GACTTCATGCGA | CTCTAGAAGAGT | ATGCGAGACTTC | ATCGGTGGAATT | TCCAGATAGCGT | TCCCAGAAGCTC |
| GCCTGTCTGCAA | TGCACAGTCGCT | CGCTTGTGTAGC | TATAGTGGGCCT | AATCCGGTCACC | ACGCTAGATTGA |
| ACTGATGGCCTC | CATGCGGATCCT | ATGAATGCGTCC | TCGACGGAGAGA | AAGTGCTTGGTA | TTACGGCTGGTC |
| TTCGATGCCGCA | TGCTCCGTAGAA | GACTCTGCTCAG | ATCTGACATCGG | GGTAAAGGGTCG | TGCAATGGTACC |
| TGTGGCTCGTGT | TGATAGGTACAC | CACGTACACGTA | GATAGGGCCAAG | GCTTTCTCAATC | AACAGGTCTCTG |
| AACTTTCAGGAG | CGAGTTCATCGA | CAGAGCTAATTG | CGGGCTTCATCA | ACAGTGCGTCCT | GTGCTAATAGGT |
| TGCACGTGATAA | AAGCAGATTGTC | TTATCCAGTCCT | CGTAACGTAATG | TAGGAACTCACC | GCGATCACACCT |
| GTTCGGTGTCCA | TAGAGGCGTAGG | CTAAGACGTCGT | TAGCGACCTCAC | TGTATTGGACAG | AATGGACCGTTC |
| AAGACAGCTATC | TCAGCGCCGTTA | GGCTCAGATTCC | ACCCTGGGTATC | AGAAAGGGTGTG | GTACGTCACTGA |
| ATTGACCGGTCA | TAGACCGACTCC | CTTGGTAGTGCC | AGCGAGAAGTGA | GCTCACAATGTG | TAGCCTGTCGTG |
| TTCTCCATCACA | GTCAACGCTGTC | GTGCTGCGCTTA | CTTCAAGATGGA | TATTGCAGCAGC | ACAGACGACGGA |
| CGTAGGTAGAGG | ACAGGAGGGTGT | AGTAGGAGGCAC | GCTGCGTATACC | AGATTCGCTCGA | TCTATGCGAACG |
| ATTTAGGACGAC | GCTGTCGTCAAC | ACCCGGATTTCG | ACAAGGCAAGGC | AGCCGGAGAGTA | CTATGAGTCCAG |
| GGATAGCCAAGG | ATAGAGGCCATT | CGTCCGTATGAA | CGTTAGTGACTG | CCTGTAGGTTGC | AGTCCTTTATCC |
| TGGTTGGTTACG | AAGCTTGAAACC | CGATTAGGAATC | GCCGTTGATGCT | AAGGCCTTTACG | AGTTTGCGAGAT |
| GTCGTCCAAATG | TAAGCGTCTCGA | ACGTCTCAGTGC | TTCAACCTTTCG | CTAGGCAATCAA | TCAACGTGCTGC |
| CAACGTGCTCCA | ATAGCTTCGTGG | TAGTAGCACCTG | TGGGAGGTGGTA | AGGACCTCGTTC | GAACCAGTACTC |
| TACACAAGTCGC | CGGGATCAAATT | AGGTCATCTTGG | CGCCTGCCAATA | CTTGTCTGGAGC | TGATAATGCACG |
| GCGTCCATGAAT | AGTCATCGAATG | TGCTGTGACCAC | TTGAGCTTGAGC | ACCGCATCAATG | TAGTGATGACCA |
| GTAATGCGTAAC | ATCTTGGAGTCG | ACACTTCGGCAA | TACTAACGCGGT | AAGGTCAATCGT | ACAGCCACCCAT |
| GTCGCCGTACAT | AGCACCGGTCTT | ACCTCCCGGATA | ATCCGCAGTCAC | ACCTACTTGTCT | TATGTTGACGGC |
| GGAATCCGATTA | GCAAATCAGCCT | GAAGAGGGTTGA | AGTGTACCATGA | TGTTGGATCGTG | CGAGTATACAAC |
| CACCCGATGGTT | GCAAGCTGTCTC | AGTAGACTTACG | CCGATTGAATCG | ACTGGATCTCGC | TACACCTTACCT |
| TTCTGAGAGGTA | AGCGGCCTATTA | TGGAAACCATTG | TATATGTGCGAG | TCAAGGGACCTT | CGTTCAAGCTAG |
| ATCCCTACGGAA | TCTTCAACTACC | AGTCCGAGTTGT | CACCCACGTTGA | AAGTCGACACAT | AACTCGCGCTAC |
| GGTTCCATTAGG | TGGAATTCGGCT | CCGCGATTTCGA | TAGTGGGTCAAT | AACATTGCAGGT | TACCAGGATTGC |
| GTGTTCCCAGAA | TAAGATGCAGTC | ACACACCCTGAC | CCTAAACTACGG | CCATGAAGTGTA | GGTTGTAAGTGT |
| CCGAGGTATAAT | TGCCGAGTAATC | TCACGAGTCACA | ACTCCCGTGTGA | TCCACAGGGTTC | CAACGAACCATC |
| AGCGTAATTAGC | ACCTTGACAAGA | CACAAAGCGATT | CTGCAAGCCTGT | TCATTAGCGTGG | CCATGCTTAGAG |
| CTCGTGAATGAC | GTAACCACCACC | CACCGTGACACT | CCAACAGCCAAT | ATGTCGAATAGC | AATGGCGACTAT |
| AGGTGAGTTCTA | CATAGCTCGGTC | GAAGATCTATCG | CGGTTCACATAG | CTGACCGTTAAG | GACAGGTTGTAT |
| CCTGTCCTATCT | AACCATGCCAAC | GACGGAACAGAC | TCAACAGTAGTG | TCGGGCTCTTAG | GACTATAATGGC |
| GGTTTAACACGC | TATGGAGCTAGT | GGACCGCTTTCA | AACACATGGGTT | ACTTTAAGGGTG | TTCAGGAACTAG |

TABLE 1-continued

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| AGACAGTAGGAG | ACTACCTCTTCA | CACGGTCCTATG | ATCGTAGTGGTC | TGGACCACTAGT | CAACAGGTAACT |
| GCCACGACTTAC | GATGATAACCCA | GAATGACGTTTG | CGAGTCACGATT | AACCAGCAGATT | TAGTTGAGCTGA |
| ATTGTTCCTACC | GGCCCAATATAA | ACTTACGCCACG | AGTGCGTTCTAG | ATCGAGGATCTA | GTCTCAAAGCAC |
| GCCGTAAACTTG | TTGTATGACAGG | ACGCCTTTCTTA | TTCTTAACGCCT | TAGCTGGCGTTC | AGTTGCCTGAAC |
| GCAGATTTCCAG | GGTAAGTTTGAC | TTGGTGCCTGTG | ACCCAGTATGGT | CACAAGTATCGA | TGGTAGTCTGAA |
| AGATGATCAGTC | CTACCACGGTAC | CATCGGATCTGA | CGTTAAGTCAGC | GATTGTGCAACC | GCATGTCGAAAT |
| GAGACGTGTTCT | CGGTCTGTCTGA | CATGTCTTCCAT | TCACAACACCGC | CTACAGGGTCTC | CCTATGCACGGT |
| TATCACCGGCAC | GTACATGTCGCC | GTTACAGTTGGC | AGCAAGGTCTTC | GTACCAGGTACT | GCGTGGTCATTA |
| TATGCCAGAGAT | TTCTAGAGTGCG | CGGACTCGTTAC | TCTAAACCCTCT | GTATACCCTTCT | AGTCACATCCGC |
| AGGTCCAAATCA | ACGGATGTTATG | TCTCGCACTGGA | CCTGATCACACG | TAGGTCTAGGTC | AGCGTCTGAACT |
| ACCGTGCTCACA | TTGAGGCTACAA | TTCTGGTCTTGT | AAGCTGCCTAGT | GACAGTAGCTTC | ATCGCGACTGCT |
| CTCCCTTTGTGT | GTAGGAACCGGA | GTCCACTTGGAC | ATTTGTGGGTAG | TGAACGTTGGAT | TGGAGGTTCTCA |
| AGCTGCACCTAA | ACATCTAGCAGA | GATTTAGAGGCT | TACATGGAGCAT | AGTGTGAACGTT | TGCTTGTAGGCA |
| CCTTGACCGATG | CCGACATTGTAG | GTCAGCCGTTAA | GCCTCAGCAGTT | ATGGTCACAAAC | CTTAAATGGGCA |
| CTATCATCCTCA | CATGTAAGGCTC | ACGGTTTCTGGA | CATCTTCTGATC | ACATAGCGGTTC | GGTATCACCCTG |
| ACTCTAGCCGGT | TGCAAGCTAAGT | GCAGCCATATTG | CAGGTTGTGCCT | GCTGTTTGACCG | CGCCTTGATAAG |
| CGATAGGCCTTA | GTGTGTGCCATA | ATAGGTGTGCTA | GGTTGCCCTGTA | CGAATACTGACA | CGTTTATCCGTT |
| AATGACCTCGTG | TGACAACCGAAT | ACCTAGCTAGTG | TGGTTTCGAAGA | TATCCTGGTTTC | TTGTACTCACTC |
| CTTAGGCATGTG | TAGGCTCGTGCT | GTCCTGACACTG | TGCGTTCTAGCG | CATTGTCCCTAT | TTCCCACCCATT |
| CCAGATATAGCA | CTCCTTAAGGCG | GGACTCAACTAA | AGTCCACTGGTA | ACCGACGCTTGT | GCCGCATTCGAT |
| GAGAGTCCACTT | TTGCCTGGGTCA | ATACGGGTTCGT | GAACTCGCTATG | CTGTGATCGGAT | |
| GAACGGGACGTA | CAATTCTGCTTC | CCTTTCACCTGT | GGTAGTTCATAG | ATGTACACCGGT | |
| ACGTGTAGGCTT | ACTGGCAAACCT | ATCAGCCAGCTC | AGGATGGGATGC | TAAGCTAAACCG | |
| GGTCTCCTACAG | AATCAGAGCTTG | GCTCCACAACGT | CAGTGATACTGC | CATTGGGAGTTC | |
| ACTGACTTAAGG | CAATGTAGACAC | AAGGAGTGCGCA | GAGGATACTACT | GATCGGTTAATG | |
| GATGCTGCCGTT | TGGCGATACGTT | AGGGAAAGGATC | GCATCGTCTGGT | CAGCGACTGTTA | |
| TTCCTAGGCCAG | GCCTTACGATAG | ACGACGCATTTG | TATGGGTAGCTA | GAGCCCAAAGAG | |
| ATTAAGCCTGGA | TACCTGTGTCTT | CGTCACTCCAAG | AGGTATTACCGA | CGATCACCACAA | |
| TGGCTTTCTATC | AACGAGGCAACG | TTACACAAAGGC | TGTCAAAGTGAC | CTAGAGCTCCCA | |
| ACAGCTCAAACA | GAAGACAGCGAC | GTATAGTCCGTG | GTAACGGCTCTA | GAACGCAATTCC | |
| GAGCGTATCCAT | ACACCTGCGATC | TCGTAAGCCGTC | GTGTACATAACG | ATCCGTCTGACG | |
| ATGGGCGAATGG | GGCGTTGCATTC | TGACGCCTCCAA | TGCTGCTCAACG | TGAAATGTCCCG | |
| GATCTCTGGGTA | ACTAGCGTTCAG | TTCTCGGTTCTC | CGGATGCAAGAG | ATTCGCCAAGAA | |
| CATCATACGGGT | TTGCGACAAAGT | GCTACTGGTATG | TGACATTCACGG | TACGTGATCCCG | |
| TACGGATTATGG | TGCGAGTATATG | GAATCCTCACCG | CACATATTGGGC | TGGGTAGATCTC | |
| ATAGCGAACTCA | TACCACAACGAA | CCTGACACACAC | TTCAATAGGGAC | AGCAATCGGTAT | |
| TAACGCTGTGTG | TCTGGAACGGTT | CAGCGTTTAGCC | ATAGCCGATGTC | GTTGGACGAAGG | |
| AACCAAACTCGA | GTACTACCTCGG | GGTATGGCTACT | ATGCGTAATGCA | ACACTATGAAGC | |

TABLE 1-continued

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| GCCGTCTCGTAA | TTCCTGTTAACC | ACAATGTCACAG | ACTCCGATAGAC | ACGGAAATCCCT | |
| CTGGGTATCTCG | CTATCCAAGTGG | GCCATAGTGTGT | GCTGAGCCTTTG | GGTTTCTATCCT | |
| GACTACCCGTTG | CAGTCTAGTACG | GGTCCCGAAATT | AACAGAGAGAGC | ACGCAATGTCTG | |
| GCGTTGCAAACT | GTGTCCGGATTC | TCTGCGAGTCTG | AATTCCGAACGC | TCGGTTACGCTG | |
| AACCGCATAAGT | TGTGGTGATGTA | ATGTAGGCTTAG | TTAGTACGCAGA | AAGCCATTGAAC | |
| ACCTTACACCTT | CTTTCGTTCAAC | TGCTTCCAATTC | GAATCTGACAAC | CGATTGTTCCGG | |
| GTAGGTGCTTAC | CCGAAGATTCTG | GCCGAGATAATT | CACACTGAAGTC | CCTAAGAGCATC | |
| CGCATTTGGATG | GTTGGCGTTACA | TCGAGTATCGAA | ACTATCAGTGGC | GATGGTTTCAGC | |
| ATAACATGTGCG | GAAGTAGCGAGC | GCCCTATCTTCT | AGACTCAGACTC | TAATTGCAGAGC | |
| CTTGAGAAATCG | TTGCGGACCCTA | AGGTACGCAATT | GACCTTTCAAGG | TACCGGCTTGCA | |
| CTACACAGCACA | GCGGAAACATGG | GTCCCTATTATC | CAAGCAGGTGAG | AGTCGGCATCTC | |
| GAAATGCTACGT | AACGTTAGTGTG | TGGGACATATCC | GGAGAACGACAC | ATATACCTGCGG | |
| TCTGAGGTTGCC | TGCATGACAGTC | GAACGATCATGT | CAGCTTCGACTG | TGTCTGACGCAA | |
| GATCATTCTCTC | TCAATCGCTTTC | TTCAGACCAGCC | ATCTTTCCCTGA | CATATCCAGCCG | |
| AGACATACCGTA | CTACCGATTGCG | ACGCATCGCACT | CTCCGAACAACA | TCTCACTGTTCC | |
| GATCCTCATGCG | TCACCCAAGGTA | CAGTAGCGATAT | GGTCACACATCA | GCTATGGAACTC | |
| ATTATCGTCCCT | AGCCAGTCATAC | GGATACTCGCAT | AGAACTTGACGT | CTCCACATTCCT | |
| CCAGACCGCTAT | TAACGGCGCTCT | CTAAGTTGCAAG | CTTGAACCCGAC | TACGTTTGGCGA | |
| AGCTCTAGAAAC | GTTTGCTCGAGA | CGCGATATCGTC | GACGTGTCCATC | AATCGCCCTTGG | |
| TCCATCGACGTG | CAAACGCACTAA | CTGATGTACACG | AGAGCCAAGAGC | CGGCGATGAAAG | |
| CGATGTGTGGTT | GAACAAAGAGCG | AGGCATCTGCTC | TGGGAATGTTGT | CCGCTACGTGAT | |
| GCGAAGTTGGGA | GCTAAGTGATGT | AGACCTGACCCT | CAATCATAGGTG | CTGGTAAGTCCA | |
| GCATTCGGCGTT | AAGGGACAAGTG | CATCGACGAGTT | ATAAGTAACCGC | AGAGCTCCTCTG | |
| CGCCATTGTGCA | AGTGTCGATTCG | GGAGTTGAGGTG | GACTTGGTAAAC | GACAAACCTTGC | |
| TCCAACTGCAGA | CTATTAAGCGGC | AGCATCCCTAAG | AATCACGGTGCT | CATTAGCTGGAA | |
| TAAAGACCCGTA | CCTACCATTGTT | CAGACGAGGAAC | ACGACCTACGCT | CCACAACGATCA | |
| TGTATCTTCACC | GAGTCCGTTGCT | TCGCTACAGATG | GATGTCATAGCC | CCGGTGTGATTC | |
| GACTGACTCGTC | GATAACTGTACG | TCGGTGTACCAA | TGTTGCGTTTCT | ATAGTGTTCGGC | |
| TCGTGGATAGCT | TAAACCTGGACA | AACACGGTTTGA | GCATACTACAGC | TAATCTCGCCGG | |
| GACGCACTAACT | CCGAATTGACAA | CTTGTGCGACAA | GAGGTATTCTGA | CAGATCCCAACC | |
| GGCGATTTACGT | CTGGCATCTAGC | AGAGTAAGCCGG | ATGTTCCTCATC | AGAGATTATGCC | |
| TAAGGCATCGCT | GGTGGTCGTTCT | AGACACCAATGT | CGGTATAGCAAT | TGAATACCTGGC | |
| ACCCATACAGCC | ACTATGGGCTAA | AATACGTCAAGC | CTTGGCCTGTAG | CTCCCACTAGAG | |
| CGCACTACGCAT | GCATTGAGTTCG | ATGGCAATTCAG | ATCAAACGCATG | AGCCCTGCTACA | |
| CAGTCGTTAAGA | GTTGCTGAGTCC | CAGTGTCATGAA | CGGTCCTGAGTT | CCTTATAGAAGG | |
| CTACGAAAGCCT | CTATGGTGAACC | CGGTGACCTACT | CTCGAGCGTACT | GGCCAAGGAAGT | |
| ATAATTGCCGAG | GGACCAAGGGAT | ACATCCCTACTT | TTAAGGACTGAC | CCTCTACTCTAA | |
| GGCATGTTATCG | GTATTGGTCAGA | TGAAGCACACTA | GTGGAAGAGACA | GAGTCGATCTTG | |

TABLE 1-continued

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| AGGCACAGTAGG | AGAACCGTCATA | GTGAATGTTCGA | TAACTAGGACGT | GACCTACCGCAT | |
| CTACTTACATCC | AACTGGAACCCT | AGTCGCTACACA | GAAAGAGTCTCT | ATGTAATAGGCC | |
| CTCTTCTGATCA | ATACTCGGCTGC | AACCACTAACCG | TCACCGGAATCC | GACTCGCAACTA | |
| ATGCTAACCACG | ACGCTTAACGAC | TTCGCTAACCTT | CGACTGCAGCTT | CTGACGATCCGT | |
| ACCAATCTCGGC | AGCTTACCGACC | GACACTCACCGT | GTTACCCGAGCT | GTGCGAGGACAA | |
| TATCCAAGCGCA | AGGGCTATAGTT | TCAGAGTAGACT | CCTAGGTCCCAA | GCAGAGAGGCTA | |
| GTACTGAAGATC | TGTCTCGCAAGC | GACCAAATGTCC | TTGAGTGGTCTG | TCCTTGTCCTTG | |
| TCGCCGTGTACA | CAGCCGCATATC | GATGCAACTTCG | CGACGAGATTAT | CTACAATTGAGG | |
| AACTGCGATATG | GATACGTTCGCA | CACCACAGAATC | AGTACTGCCTGC | GTTGACCATCGC | |
| CTTCCAACTCAT | CCAAGATTCGCC | GGAGCTCTGTAT | GAAGTCCACACT | CAATGAGGGAGA | |
| GAGATCGCCTAT | GAGGCTGATTTA | CCTTAAGGGCAT | GTAGAATGCTCC | AAGCAACGGTGG | |
| TGTACATCGCCG | GAGTTAGCATCA | GCTGCTACAAGT | ACACCCTATCGG | CTCCAATGACGC | |
| TGTTAAGCAGCA | TGTAGTATAGGC | GTAAACGACTTG | AGGAGGATAAAG | ATGGAAGGTGGC | |
| ACGGCGTTATGT | CTCACGCAATGC | CGCCCTCTTCTT | GCATGGGTTATC | CCGGCTTATGTG | |
| ACTTTGCTTTGC | GTCCCGTGAAAT | ACTAGACGACTA | GTTCCCAACGGT | CTGTGCAACGTC | |
| CAAAGCGGTATT | GGACAGTGTATT | AGGTTAAGTGCT | GTCAGAGTATTG | AGTCAATGGCCT | |
| CGAAACTACGTA | ACACGACTATAG | ATATCCTGGGAC | ATGACAGAACCT | GGAACACATGTT | |
| GAGGACCAGCAA | GTGTAGGTGCTT | TTGTAGCCGACA | ACAAGTGCTGCT | AGCGCATATCCA | |
| AATAGCATGTCG | TGAACTAGCGTC | TCAGAAGCTCAA | AATAGTCGTGAC | TGCAACTTGCAG | |
| CGGAGTAATCCT | TCCGAGTCACCA | ACTGTGACGTCC | TACAAGTGGTCC | GTGTGGCAGAAG | |
| CTGTGTCCATGG | TCCTCTTTGGTC | TTGCAGTGCAAC | GCTGGTCTAGTC | GTGACCCTGTCA | |
| CTTCGCGGATGT | TCCACCCTCTAT | TGTCATGGCTGA | GGCATCCTGGTT | CACGCAGTCTAC | |
| ATAGGCTGTAGT | TCGTGACGCTAA | TTCGTGAGGATA | GTGCCTCAGGTT | TTCACTGTGCGG | |
| TGTGTAGCCATG | ACGGCTAGTTCC | TCCCAACCTAGG | ATTACAGCGACA | AACGAATACCAC | |
| AAGGGCGCTGAA | GCACTGGCATAT | TAGAATCAACGC | ATGCAGAGATCT | ATGGTTCACCCG | |
| GTTTCCGTGGTG | GGCATTAGTTGA | CACAATACACCG | CGTATGCCGTAC | TAGCGGAAGACG | |
| AGGAACCAGACG | CGGTAGTTGATC | GTATGACTAGCA | AGCCGACTCTGT | CCTCATGCTATT | |
| TAATGCCCAGGT | TGAAAGCGGCGA | ATGCTCTAGAGA | CTATTCTTGGCT | CCATCTTACCAT | |
| TATGAACGTCCG | GGTTACGGTTAC | AGCTAGCGTTCA | TCGGTAGCAACT | TATGCTCTCTCA | |
| CCACATTGGGTC | ACATCAGGTCAC | GGTCTTAGCACC | CCAAATGATGAC | CGTGTAGTAGAT | |
| TCAGTCAGATGA | GTTGATACGATG | TACCATCCATCT | GCAGGTAACATT | ACATGGGCGGAA | |
| AAGTCACACACA | CAGACACTTCCG | AGGGATGGACCA | GCACGTTCTACG | CCGCTGATGTCA | |
| GCTGTGATTCGA | TCACCATCCGAG | ACTAATACGCGA | GACTGGAGATGG | ACGAGTTTACCG | |
| CTAGCTATGGAC | ACCCACCACTAG | TCATACAGCCAG | ACTAAGTACCCG | GGAGATTGGAGA | |
| CTTGACGAGGTT | CAGAAGGTGTGG | GGAGGCCATAAG | TAAGTGAGTACC | AAGCCCAGCATT | |
| ACCTGGGAATAT | GAAGCTTGAATC | GTCCGATCCTAG | ATCGACAACACC | GGTGAAACCTAT | |
| CTCTGCCTAATT | ACTAGGATCAGT | CTGTGGGATTCA | AGCACACTACAC | TGGTAAGAGTCT | |
| ATATGACCCAGC | GCTCCTTAGAAG | TTGTCTACCTAC | GAATGTTGCGCT | GCGCTTAGAATA | |

TABLE 1-continued

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| CTCTATTCCACC | TCCCATTCCCAT | GAAGGCTCCTTA | CGCGCAAGTATT | AGGTGTATCACC | |
| ATTGAGTGAGTC | TGGCGTCATTCG | AGATTACAACCG | ATAGTTAGGGCT | ATTGTCAAGCAG | |
| TTATGGTACGGA | AATCCTCGGAGT | TCTTCTGCCCTA | GTTCAACAGCTG | TTCGCAGATACG | |
| GCTAGTTATGGA | CTGGACGCATTA | TGAAGTCACAGT | TCAGCAAATGGT | CATAGGCCATCA | |
| CAGATTAACCAG | ACCGATTAGGTA | CTTAGTGCAGAA | AGGGACTTCAAT | CCTTGGAATCGC | |
| GGCTGCATACTC | ATGTGCTGCTCG | CATCAGTACGCC | GAAGTGTATCTG | CACTTGCTCTCT | |
| TTGGTAAAGTGC | TACGTACGAAAC | TAGAACACCATG | TCCTGTGCGAGT | GCAACTTCGGTA | |
| AAGTGGCTATCC | ATCACATTCTCC | CCGCATGACCTA | CCAACGTAACCA | GCCAATCCAACA | |
| AACCGATGTACC | AGCCTGGTACCT | GAGAATGGAAAG | AAGGTGGACAAG | CTGGAACATTAG | |
| TCGATTGGCCGT | GCTAAAGTCGTA | AACCCTAACTGG | CAATTGCGTGCA | TTAGCCCAGCGT | |
| GCATTACTGGAC | TCTCAGCGCGTA | TCCATACCGGAA | ACCAGCTCAGAT | AATGGTTCAGCA | |
| TTGGGCCACATA | GACCCTAGACCT | GTTCAGACTAGC | ACGGTACCCTAC | CAGCAAGAGGAC | |
| CACACAAAGTCA | TATTCAGCGGAC | GACACCACAATA | TCATAGGGTAGT | CTAGTACAAGCC | |
| GCCAAGGATAGG | GTTCCGGATTAG | CGATTTAGGCCA | ATGGAGTTGTTG | AGAGCGGAACAA | |
| CGCCACGTGTAT | GCGTGTAATTAG | AGGATATTCGTG | CGTATCTCAGGA | GCAGTTGCCTCA | |
| GCAACCGATTGT | CTGTAGCTTGGC | CAATACGACCGT | TAGTTCGGTGAC | CGCGCCTTAAAC | |
| CATGTGCTTAGG | ATGCCTCGTAAG | GCCATGTGTGTA | CCATGGCTGTGT | TCCGCGCAAGTT | |
| GTTCCTCCATTA | ACCTATGGTGAA | GACTCCTAGACC | CTAGTCGCTGGT | TAACCACCAACG | |
| ACCTGTCCTTTC | CTGTTACAGCGA | AAGGCAAGAAGA | TCCAAGCGTCAC | TGCGTCAGCTAC | |
| GTTCACGCCCAA | CAGTCAGGCCTT | ACGAGGAGTCGA | GCTTCATTTCTG | CGAAATGCATGT | |
| CGATCGAACACT | ACTGAGCTGCAT | GCGGTACTACTA | AACTTGGCCGTA | ATGATCGGTACA | |
| CATGCCAACATG | ACGAAGTCTACC | TCAGCTGACTAG | CATACGATACAG | TTACCCGCACAG | |
| GAGTACAGTCTA | ACCGTCTTTCTC | ACCTGATCCGCA | GGTTGAGAAGAG | CCTGTTAGCGAA | |
| CCTACATGAGAC | AGTCTGTCTGCG | CAAGCTAGCTGT | CTGGGAGTTGTT | GCTCCGACCATA | |
| TCCGTGGTATAG | CCGCACTCAAGT | GTGGATAAACTC | ATCATCTCGGCG | ACAAATCGTTGG | |
| TCTACGGCACGT | TGTGGAAACTCC | GGTACAATGATC | ATTACCCACAGG | GAAGGAAAGTAG | |
| ATGCTGCAACAC | TTAGGCAGGTTC | ACTGTCGCAGTA | CACATCAGCGCT | ACAAACATGGTC | |
| TTCTCATGGAGG | TAAGACTACTGG | CATCCTGAGCAA | TGACCATAGTGA | GGACTATCGTTG | |
| CATAGTGATTGG | CGCGAAGTTTCA | CAACATCGTAGC | GATAAGCGCCTT | GCTATATCCAGG | |
| GCTATCAAGACA | CGATACACTGCC | GGCAATCATCTG | TAGTCTAAGGGT | TATTCCCACGTT | |
| CCGTGACAACTC | TTGAAATCCCGG | TATCGCGCGATA | AATTAGGCGTGT | CCATTAGTTCCT | |
| CGTTCCTTGTTA | GTTAGGGAGCGA | TACGGTCTGGAT | TGCTCTTGCTCT | TAACCTTCGCTT | |
| GGAATTATCGGT | TTACTGTGGCCG | TCGTTCAGGACC | TCCACTAGAGCA | GTAATCTGCCGA | |
| CATCAAGCATAG | ATATAAGGCCCA | TGATCCGGGTAT | CATTGCAAAGCA | GGTGGCATGGAA | |

TABLE 2

| | forward primer binding site fragment | 5' universal sequence fragment | barcode sequence fragment | 3' universal sequence fragment | reverse primer binding site fragment |
|---|---|---|---|---|---|
| (SEQ ID NO: 1) | CCTACGGGAGGCATCAG | GCAGATCTCG | CCTACGGGAGGCATCAG | AGTCAGTCAGCC | GGATTAGATACCCTAGTAGTC |
| (SEQ ID NO: 2) | CCTACGGGAGGCATCAG | GCAGATCTCG | CCTACGGGAGGCATCAG | AGTCAGTCAGCC | GGATTAGATACCCTAGTAGTC |
| (SEQ ID NO: 3) | CCTACGGGAGGCATCAG | GCAGATCTCG | CCTACGGGAGGCATCAG | AGTCAGTCAGCC | GGATTAGATACCCTAGTAGTC |
| (SEQ ID NO: 4) | CCTACGGGAGGCATCAG | GCAGATCTCG | CCTACGGGAGGCATCAG | AGTCAGTCAGCC | GGATTAGATACCCTAGTAGTC |
| (SEQ ID NO: 5) | CCTACGGGAGGCATCAG | GCAGATCTCG | CCTACGGGAGGCATCAG | AGTCAGTCAGCC | GGATTAGATACCCTAGTAGTC |
| (SEQ ID NO: 6) | CCTACGGGAGGCATCAG | GCAGATCTCG | CCTACGGGAGGCATCAG | AGTCAGTCAGCC | GGATTAGATACCCTAGTAGTC |
| (SEQ ID NO: 7) | CCTACGGGAGGCATCAG | GCAGATCTCG | CCTACGGGAGGCATCAG | AGTCAGTCAGCC | GGATTAGATACCCTAGTAGTC |
| (SEQ ID NO: 8) | CCTACGGGAGGCATCAG | GCAGATCTCG | CCTACGGGAGGCATCAG | AGTCAGTCAGCC | GGATTAGATACCCTAGTAGTC |
| (SEQ ID NO: 9) | CCTACGGGAGGCATCAG | GCAGATCTCG | CCTACGGGAGGCATCAG | AGTCAGTCAGCC | GGATTAGATACCCTAGTAGTC |
| (SEQ ID NO: 10) | CCTACGGGAGGCATCAG | GCAGATCTCG | CCTACGGGAGGCATCAG | AGTCAGTCAGCC | GGATTAGATACCCTAGTAGTC |
| (SEQ ID NO: 11) | CCTACGGGAGGCATCAG | GCAGATCTCG | CCTACGGGAGGCATCAG | AGTCAGTCAGCC | GGATTAGATACCCTAGTAGTC |
| (SEQ ID NO: 12) | CCTACGGGAGGCATCAG | GCAGATCTCG | CCTACGGGAGGCATCAG | AGTCAGTCAGCC | GGATTAGATACCCTAGTAGTC |
| (SEQ ID NO: 13) | CCTACGGGAGGCATCAG | GCAGATCTCG | CCTACGGGAGGCATCAG | AGTCAGTCAGCC | GGATTAGATACCCTAGTAGTC |
| (SEQ ID NO: 14) | CCTACGGGAGGCATCAG | GCAGATCTCG | CCTACGGGAGGCATCAG | AGTCAGTCAGCC | GGATTAGATACCCTAGTAGTC |
| (SEQ ID NO: 15) | CCTACGGGAGGCATCAG | GCAGATCTCG | CCTACGGGAGGCATCAG | AGTCAGTCAGCC | GGATTAGATACCCTAGTAGTC |
| (SEQ ID NO: 16) | CCTACGGGAGGCATCAG | GCAGATCTCG | CCTACGGGAGGCATCAG | AGTCAGTCAGCC | GGATTAGATACCCTAGTAGTC |
| (SEQ ID NO: 17) | CCTACGGGAGGCATCAG | GCAGATCTCG | CCTACGGGAGGCATCAG | AGTCAGTCAGCC | GGATTAGATACCCTAGTAGTC |
| (SEQ ID NO: 18) | CCTACGGGAGGCATCAG | GCAGATCTCG | CCTACGGGAGGCATCAG | AGTCAGTCAGCC | GGATTAGATACCCTAGTAGTC |
| (SEQ ID NO: 19) | CCTACGGGAGGCATCAG | GCAGATCTCG | CCTACGGGAGGCATCAG | AGTCAGTCAGCC | GGATTAGATACCCTAGTAGTC |
| (SEQ ID NO: 20) | CCTACGGGAGGCATCAG | GCAGATCTCG | CCTACGGGAGGCATCAG | AGTCAGTCAGCC | GGATTAGATACCCTAGTAGTC |
| (SEQ ID NO: 21) | CCTACGGGAGGCATCAG | GCAGATCTCG | CCTACGGGAGGCATCAG | AGTCAGTCAGCC | GGATTAGATACCCTAGTAGTC |
| (SEQ ID NO: 22) | CCTACGGGAGGCATCAG | GCAGATCTCG | CCTACGGGAGGCATCAG | AGTCAGTCAGCC | GGATTAGATACCCTAGTAGTC |
| (SEQ ID NO: 23) | CCTACGGGAGGCATCAG | GCAGATCTCG | CCTACGGGAGGCATCAG | AGTCAGTCAGCC | GGATTAGATACCCTAGTAGTC |
| (SEQ ID NO: 24) | CCTACGGGAGGCATCAG | GCAGATCTCG | CCTACGGGAGGCATCAG | AGTCAGTCAGCC | GGATTAGATACCCTAGTAGTC |
| (SEQ ID NO: 25) | CCTACGGGAGGCATCAG | GCAGATCTCG | CCTACGGGAGGCATCAG | AGTCAGTCAGCC | GGATTAGATACCCTAGTAGTC |
| (SEQ ID NO: 26) | CCTACGGGAGGCATCAG | GCAGATCTCG | CCTACGGGAGGCATCAG | AGTCAGTCAGCC | GGATTAGATACCCTAGTAGTC |
| (SEQ ID NO: 27) | CCTACGGGAGGCATCAG | GCAGATCTCG | CCTACGGGAGGCATCAG | AGTCAGTCAGCC | GGATTAGATACCCTAGTAGTC |
| (SEQ ID NO: 28) | CCTACGGGAGGCATCAG | GCAGATCTCG | CCTACGGGAGGCATCAG | AGTCAGTCAGCC | GGATTAGATACCCTAGTAGTC |
| (SEQ ID NO: 29) | CCTACGGGAGGCATCAG | GCAGATCTCG | CCTACGGGAGGCATCAG | AGTCAGTCAGCC | GGATTAGATACCCTAGTAGTC |
| (SEQ ID NO: 30) | CCTACGGGAGGCATCAG | GCAGATCTCG | CCTACGGGAGGCATCAG | AGTCAGTCAGCC | GGATTAGATACCCTAGTAGTC |
| (SEQ ID NO: 31) | CCTACGGGAGGCATCAG | GCAGATCTCG | CCTACGGGAGGCATCAG | AGTCAGTCAGCC | GGATTAGATACCCTAGTAGTC |
| (SEQ ID NO: 32) | CCTACGGGAGGCATCAG | GCAGATCTCG | CCTACGGGAGGCATCAG | AGTCAGTCAGCC | GGATTAGATACCCTAGTAGTC |
| (SEQ ID NO: 33) | CCTACGGGAGGCATCAG | GCAGATCTCG | CCTACGGGAGGCATCAG | AGTCAGTCAGCC | GGATTAGATACCCTAGTAGTC |
| (SEQ ID NO: 34) | CCTACGGGAGGCATCAG | GCAGATCTCG | CCTACGGGAGGCATCAG | AGTCAGTCAGCC | GGATTAGATACCCTAGTAGTC |
| (SEQ ID NO: 35) | CCTACGGGAGGCATCAG | GCAGATCTCG | CCTACGGGAGGCATCAG | AGTCAGTCAGCC | GGATTAGATACCCTAGTAGTC |
| (SEQ ID NO: 36) | CCTACGGGAGGCATCAG | GCAGATCTCG | CCTACGGGAGGCATCAG | AGTCAGTCAGCC | GGATTAGATACCCTAGTAGTC |
| (SEQ ID NO: 37) | CCTACGGGAGGCATCAG | GCAGATCTCG | CCTACGGGAGGCATCAG | AGTCAGTCAGCC | GGATTAGATACCCTAGTAGTC |
| (SEQ ID NO: 38) | CCTACGGGAGGCATCAG | GCAGATCTCG | CCTACGGGAGGCATCAG | AGTCAGTCAGCC | GGATTAGATACCCTAGTAGTC |

TABLE 2-continued

| | forward primer binding site fragment | 5' universal sequence fragment | barcode sequence fragment | 3' universal sequence fragment | reverse primer binding site fragment |
|---|---|---|---|---|---|
| (SEQ ID NO: 39) | CCTACGGGAGGCATCAG | GCAGATCTCG | CCTACGGGAGGCATCAG | AGTCAGTCAGCC | GGATTAGATACCCTAGTAGTC |
| (SEQ ID NO: 40) | CCTACGGGAGGCATCAG | GCAGATCTCG | CCTACGGGAGGCATCAG | AGTCAGTCAGCC | GGATTAGATACCCTAGTAGTC |
| (SEQ ID NO: 41) | CCTACGGGAGGCATCAG | GCAGATCTCG | CCTACGGGAGGCATCAG | AGTCAGTCAGCC | GGATTAGATACCCTAGTAGTC |
| (SEQ ID NO: 42) | CCTACGGGAGGCATCAG | GCAGATCTCG | CCTACGGGAGGCATCAG | AGTCAGTCAGCC | GGATTAGATACCCTAGTAGTC |
| (SEQ ID NO: 43) | CCTACGGGAGGCATCAG | GCAGATCTCG | CCTACGGGAGGCATCAG | AGTCAGTCAGCC | GGATTAGATACCCTAGTAGTC |
| (SEQ ID NO: 44) | CCTACGGGAGGCATCAG | GCAGATCTCG | CCTACGGGAGGCATCAG | AGTCAGTCAGCC | GGATTAGATACCCTAGTAGTC |
| (SEQ ID NO: 45) | CCTACGGGAGGCATCAG | GCAGATCTCG | CCTACGGGAGGCATCAG | AGTCAGTCAGCC | GGATTAGATACCCTAGTAGTC |
| (SEQ ID NO: 46) | CCTACGGGAGGCATCAG | GCAGATCTCG | CCTACGGGAGGCATCAG | AGTCAGTCAGCC | GGATTAGATACCCTAGTAGTC |
| (SEQ ID NO: 47) | CCTACGGGAGGCATCAG | GCAGATCTCG | CCTACGGGAGGCATCAG | AGTCAGTCAGCC | GGATTAGATACCCTAGTAGTC |
| (SEQ ID NO: 48) | CCTACGGGAGGCATCAG | GCAGATCTCG | CCTACGGGAGGCATCAG | AGTCAGTCAGCC | GGATTAGATACCCTAGTAGTC |
| (SEQ ID NO: 49) | CCTACGGGAGGCATCAG | GCAGATCTCG | CCTACGGGAGGCATCAG | AGTCAGTCAGCC | GGATTAGATACCCTAGTAGTC |
| (SEQ ID NO: 50) | CCTACGGGAGGCATCAG | GCAGATCTCG | CCTACGGGAGGCATCAG | AGTCAGTCAGCC | GGATTAGATACCCTAGTAGTC |
| (SEQ ID NO: 51) | CCTACGGGAGGCATCAG | GCAGATCTCG | CCTACGGGAGGCATCAG | AGTCAGTCAGCC | GGATTAGATACCCTAGTAGTC |
| (SEQ ID NO: 52) | CCTACGGGAGGCATCAG | GCAGATCTCG | CCTACGGGAGGCATCAG | AGTCAGTCAGCC | GGATTAGATACCCTAGTAGTC |
| (SEQ ID NO: 53) | CCTACGGGAGGCATCAG | GCAGATCTCG | CCTACGGGAGGCATCAG | AGTCAGTCAGCC | GGATTAGATACCCTAGTAGTC |
| (SEQ ID NO: 54) | CCTACGGGAGGCATCAG | GCAGATCTCG | CCTACGGGAGGCATCAG | AGTCAGTCAGCC | GGATTAGATACCCTAGTAGTC |
| (SEQ ID NO: 55) | CCTACGGGAGGCATCAG | GCAGATCTCG | CCTACGGGAGGCATCAG | AGTCAGTCAGCC | GGATTAGATACCCTAGTAGTC |
| (SEQ ID NO: 56) | CCTACGGGAGGCATCAG | GCAGATCTCG | CCTACGGGAGGCATCAG | AGTCAGTCAGCC | GGATTAGATACCCTAGTAGTC |
| (SEQ ID NO: 57) | CCTACGGGAGGCATCAG | GCAGATCTCG | CCTACGGGAGGCATCAG | AGTCAGTCAGCC | GGATTAGATACCCTAGTAGTC |
| (SEQ ID NO: 58) | CCTACGGGAGGCATCAG | GCAGATCTCG | CCTACGGGAGGCATCAG | AGTCAGTCAGCC | GGATTAGATACCCTAGTAGTC |
| (SEQ ID NO: 59) | CCTACGGGAGGCATCAG | GCAGATCTCG | CCTACGGGAGGCATCAG | AGTCAGTCAGCC | GGATTAGATACCCTAGTAGTC |
| (SEQ ID NO: 60) | CCTACGGGAGGCATCAG | GCAGATCTCG | CCTACGGGAGGCATCAG | AGTCAGTCAGCC | GGATTAGATACCCTAGTAGTC |
| (SEQ ID NO: 61) | CCTACGGGAGGCATCAG | GCAGATCTCG | CCTACGGGAGGCATCAG | AGTCAGTCAGCC | GGATTAGATACCCTAGTAGTC |
| (SEQ ID NO: 62) | CCTACGGGAGGCATCAG | GCAGATCTCG | CCTACGGGAGGCATCAG | AGTCAGTCAGCC | GGATTAGATACCCTAGTAGTC |
| (SEQ ID NO: 63) | CCTACGGGAGGCATCAG | GCAGATCTCG | CCTACGGGAGGCATCAG | AGTCAGTCAGCC | GGATTAGATACCCTAGTAGTC |
| (SEQ ID NO: 64) | CCTACGGGAGGCATCAG | GCAGATCTCG | CCTACGGGAGGCATCAG | AGTCAGTCAGCC | GGATTAGATACCCTAGTAGTC |
| (SEQ ID NO: 65) | CCTACGGGAGGCATCAG | GCAGATCTCG | CCTACGGGAGGCATCAG | AGTCAGTCAGCC | GGATTAGATACCCTAGTAGTC |
| (SEQ ID NO: 66) | CCTACGGGAGGCATCAG | GCAGATCTCG | CCTACGGGAGGCATCAG | AGTCAGTCAGCC | GGATTAGATACCCTAGTAGTC |
| (SEQ ID NO: 67) | CCTACGGGAGGCATCAG | GCAGATCTCG | CCTACGGGAGGCATCAG | AGTCAGTCAGCC | GGATTAGATACCCTAGTAGTC |
| (SEQ ID NO: 68) | CCTACGGGAGGCATCAG | GCAGATCTCG | CCTACGGGAGGCATCAG | AGTCAGTCAGCC | GGATTAGATACCCTAGTAGTC |
| (SEQ ID NO: 69) | CCTACGGGAGGCATCAG | GCAGATCTCG | CCTACGGGAGGCATCAG | AGTCAGTCAGCC | GGATTAGATACCCTAGTAGTC |
| (SEQ ID NO: 70) | CCTACGGGAGGCATCAG | GCAGATCTCG | CCTACGGGAGGCATCAG | AGTCAGTCAGCC | GGATTAGATACCCTAGTAGTC |
| (SEQ ID NO: 71) | CCTACGGGAGGCATCAG | GCAGATCTCG | CCTACGGGAGGCATCAG | AGTCAGTCAGCC | GGATTAGATACCCTAGTAGTC |
| (SEQ ID NO: 72) | CCTACGGGAGGCATCAG | GCAGATCTCG | CCTACGGGAGGCATCAG | AGTCAGTCAGCC | GGATTAGATACCCTAGTAGTC |
| (SEQ ID NO: 73) | CCTACGGGAGGCATCAG | GCAGATCTCG | CCTACGGGAGGCATCAG | AGTCAGTCAGCC | GGATTAGATACCCTAGTAGTC |
| (SEQ ID NO: 74) | CCTACGGGAGGCATCAG | GCAGATCTCG | CCTACGGGAGGCATCAG | AGTCAGTCAGCC | GGATTAGATACCCTAGTAGTC |
| (SEQ ID NO: 75) | CCTACGGGAGGCATCAG | GCAGATCTCG | CCTACGGGAGGCATCAG | AGTCAGTCAGCC | GGATTAGATACCCTAGTAGTC |

TABLE 2-continued

| | forward primer binding site fragment | 5' universal sequence fragment | barcode sequence fragment | 3' universal sequence fragment | reverse primer binding site fragment |
|---|---|---|---|---|---|
| (SEQ ID NO: 76) | CCTACGGGAGGCATCAG | GCAGATCTCG | CCTACGGGAGGCATCAG | AGTCAGTCAGCC | GGATTAGATACCCTAGTAGTC |
| (SEQ ID NO: 77) | CCTACGGGAGGCATCAG | GCAGATCTCG | CCTACGGGAGGCATCAG | AGTCAGTCAGCC | GGATTAGATACCCTAGTAGTC |
| (SEQ ID NO: 78) | CCTACGGGAGGCATCAG | GCAGATCTCG | CCTACGGGAGGCATCAG | AGTCAGTCAGCC | GGATTAGATACCCTAGTAGTC |
| (SEQ ID NO: 79) | CCTACGGGAGGCATCAG | GCAGATCTCG | CCTACGGGAGGCATCAG | AGTCAGTCAGCC | GGATTAGATACCCTAGTAGTC |
| (SEQ ID NO: 80) | CCTACGGGAGGCATCAG | GCAGATCTCG | CCTACGGGAGGCATCAG | AGTCAGTCAGCC | GGATTAGATACCCTAGTAGTC |
| (SEQ ID NO: 81) | CCTACGGGAGGCATCAG | GCAGATCTCG | CCTACGGGAGGCATCAG | AGTCAGTCAGCC | GGATTAGATACCCTAGTAGTC |
| (SEQ ID NO: 82) | CCTACGGGAGGCATCAG | GCAGATCTCG | CCTACGGGAGGCATCAG | AGTCAGTCAGCC | GGATTAGATACCCTAGTAGTC |
| (SEQ ID NO: 83) | CCTACGGGAGGCATCAG | GCAGATCTCG | CCTACGGGAGGCATCAG | AGTCAGTCAGCC | GGATTAGATACCCTAGTAGTC |
| (SEQ ID NO: 84) | CCTACGGGAGGCATCAG | GCAGATCTCG | CCTACGGGAGGCATCAG | AGTCAGTCAGCC | GGATTAGATACCCTAGTAGTC |
| (SEQ ID NO: 85) | CCTACGGGAGGCATCAG | GCAGATCTCG | CCTACGGGAGGCATCAG | AGTCAGTCAGCC | GGATTAGATACCCTAGTAGTC |
| (SEQ ID NO: 86) | CCTACGGGAGGCATCAG | GCAGATCTCG | CCTACGGGAGGCATCAG | AGTCAGTCAGCC | GGATTAGATACCCTAGTAGTC |
| (SEQ ID NO: 87) | CCTACGGGAGGCATCAG | GCAGATCTCG | CCTACGGGAGGCATCAG | AGTCAGTCAGCC | GGATTAGATACCCTAGTAGTC |
| (SEQ ID NO: 88) | CCTACGGGAGGCATCAG | GCAGATCTCG | CCTACGGGAGGCATCAG | AGTCAGTCAGCC | GGATTAGATACCCTAGTAGTC |
| (SEQ ID NO: 89) | CCTACGGGAGGCATCAG | GCAGATCTCG | CCTACGGGAGGCATCAG | AGTCAGTCAGCC | GGATTAGATACCCTAGTAGTC |
| (SEQ ID NO: 90) | CCTACGGGAGGCATCAG | GCAGATCTCG | CCTACGGGAGGCATCAG | AGTCAGTCAGCC | GGATTAGATACCCTAGTAGTC |
| (SEQ ID NO: 91) | CCTACGGGAGGCATCAG | GCAGATCTCG | CCTACGGGAGGCATCAG | AGTCAGTCAGCC | GGATTAGATACCCTAGTAGTC |
| (SEQ ID NO: 92) | CCTACGGGAGGCATCAG | GCAGATCTCG | CCTACGGGAGGCATCAG | AGTCAGTCAGCC | GGATTAGATACCCTAGTAGTC |
| (SEQ ID NO: 93) | CCTACGGGAGGCATCAG | GCAGATCTCG | CCTACGGGAGGCATCAG | AGTCAGTCAGCC | GGATTAGATACCCTAGTAGTC |
| (SEQ ID NO: 94) | CCTACGGGAGGCATCAG | GCAGATCTCG | CCTACGGGAGGCATCAG | AGTCAGTCAGCC | GGATTAGATACCCTAGTAGTC |
| (SEQ ID NO: 95) | CCTACGGGAGGCATCAG | GCAGATCTCG | CCTACGGGAGGCATCAG | AGTCAGTCAGCC | GGATTAGATACCCTAGTAGTC |
| (SEQ ID NO: 96) | CCTACGGGAGGCATCAG | GCAGATCTCG | CCTACGGGAGGCATCAG | AGTCAGTCAGCC | GGATTAGATACCCTAGTAGTC |
| (SEQ ID NO: 97) | CCTACGGGAGGCATCAG | GCAGATCTCG | CCTACGGGAGGCATCAG | AGTCAGTCAGCC | GGATTAGATACCCTAGTAGTC |
| (SEQ ID NO: 98) | CCTACGGGAGGCATCAG | GCAGATCTCG | CCTACGGGAGGCATCAG | AGTCAGTCAGCC | GGATTAGATACCCTAGTAGTC |
| (SEQ ID NO: 99) | CCTACGGGAGGCATCAG | GCAGATCTCG | CCTACGGGAGGCATCAG | AGTCAGTCAGCC | GGATTAGATACCCTAGTAGTC |
| (SEQ ID NO: 100) | CCTACGGGAGGCATCAG | GCAGATCTCG | CCTACGGGAGGCATCAG | AGTCAGTCAGCC | GGATTAGATACCCTAGTAGTC |
| (SEQ ID NO: 101) | CCTACGGGAGGCATCAG | GCAGATCTCG | CCTACGGGAGGCATCAG | AGTCAGTCAGCC | GGATTAGATACCCTAGTAGTC |
| (SEQ ID NO: 102) | CCTACGGGAGGCATCAG | GCAGATCTCG | CCTACGGGAGGCATCAG | AGTCAGTCAGCC | GGATTAGATACCCTAGTAGTC |
| (SEQ ID NO: 103) | CCTACGGGAGGCATCAG | GCAGATCTCG | CCTACGGGAGGCATCAG | AGTCAGTCAGCC | GGATTAGATACCCTAGTAGTC |
| (SEQ ID NO: 104) | CCTACGGGAGGCATCAG | GCAGATCTCG | CCTACGGGAGGCATCAG | AGTCAGTCAGCC | GGATTAGATACCCTAGTAGTC |
| (SEQ ID NO: 105) | CCTACGGGAGGCATCAG | GCAGATCTCG | CCTACGGGAGGCATCAG | AGTCAGTCAGCC | GGATTAGATACCCTAGTAGTC |
| (SEQ ID NO: 106) | CCTACGGGAGGCATCAG | GCAGATCTCG | CCTACGGGAGGCATCAG | AGTCAGTCAGCC | GGATTAGATACCCTAGTAGTC |
| (SEQ ID NO: 107) | CCTACGGGAGGCATCAG | GCAGATCTCG | CCTACGGGAGGCATCAG | AGTCAGTCAGCC | GGATTAGATACCCTAGTAGTC |
| (SEQ ID NO: 108) | CCTACGGGAGGCATCAG | GCAGATCTCG | CCTACGGGAGGCATCAG | AGTCAGTCAGCC | GGATTAGATACCCTAGTAGTC |
| (SEQ ID NO: 109) | CCTACGGGAGGCATCAG | GCAGATCTCG | CCTACGGGAGGCATCAG | AGTCAGTCAGCC | GGATTAGATACCCTAGTAGTC |
| (SEQ ID NO: 110) | CCTACGGGAGGCATCAG | GCAGATCTCG | CCTACGGGAGGCATCAG | AGTCAGTCAGCC | GGATTAGATACCCTAGTAGTC |
| (SEQ ID NO: 111) | CCTACGGGAGGCATCAG | GCAGATCTCG | CCTACGGGAGGCATCAG | AGTCAGTCAGCC | GGATTAGATACCCTAGTAGTC |
| (SEQ ID NO: 112) | CCTACGGGAGGCATCAG | GCAGATCTCG | CCTACGGGAGGCATCAG | AGTCAGTCAGCC | GGATTAGATACCCTAGTAGTC |
| (SEQ ID NO: 113) | CCTACGGGAGGCATCAG | GCAGATCTCG | CCTACGGGAGGCATCAG | AGTCAGTCAGCC | GGATTAGATACCCTAGTAGTC |

TABLE 2-continued

| | forward primer binding site fragment | 5' universal sequence fragment | barcode sequence fragment | 3' universal sequence fragment | reverse primer binding site fragment |
|---|---|---|---|---|---|
| (SEQ ID NO: 114) | CCTACGGGAGGCATCAG | GCAGATCTCG | CCTACGGGAGGCATCAG | AGTCAGTCAGCC | GGATTAGATACCCTAGTAGTC |
| (SEQ ID NO: 115) | CCTACGGGAGGCATCAG | GCAGATCTCG | CCTACGGGAGGCATCAG | AGTCAGTCAGCC | GGATTAGATACCCTAGTAGTC |
| (SEQ ID NO: 116) | CCTACGGGAGGCATCAG | GCAGATCTCG | CCTACGGGAGGCATCAG | AGTCAGTCAGCC | GGATTAGATACCCTAGTAGTC |
| (SEQ ID NO: 117) | CCTACGGGAGGCATCAG | GCAGATCTCG | CCTACGGGAGGCATCAG | AGTCAGTCAGCC | GGATTAGATACCCTAGTAGTC |
| (SEQ ID NO: 118) | CCTACGGGAGGCATCAG | GCAGATCTCG | CCTACGGGAGGCATCAG | AGTCAGTCAGCC | GGATTAGATACCCTAGTAGTC |
| (SEQ ID NO: 119) | CCTACGGGAGGCATCAG | GCAGATCTCG | CCTACGGGAGGCATCAG | AGTCAGTCAGCC | GGATTAGATACCCTAGTAGTC |
| (SEQ ID NO: 120) | CCTACGGGAGGCATCAG | GCAGATCTCG | CCTACGGGAGGCATCAG | AGTCAGTCAGCC | GGATTAGATACCCTAGTAGTC |
| (SEQ ID NO: 121) | CCTACGGGAGGCATCAG | GCAGATCTCG | CCTACGGGAGGCATCAG | AGTCAGTCAGCC | GGATTAGATACCCTAGTAGTC |
| (SEQ ID NO: 122) | CCTACGGGAGGCATCAG | GCAGATCTCG | CCTACGGGAGGCATCAG | AGTCAGTCAGCC | GGATTAGATACCCTAGTAGTC |
| (SEQ ID NO: 123) | CCTACGGGAGGCATCAG | GCAGATCTCG | CCTACGGGAGGCATCAG | AGTCAGTCAGCC | GGATTAGATACCCTAGTAGTC |
| (SEQ ID NO: 124) | CCTACGGGAGGCATCAG | GCAGATCTCG | CCTACGGGAGGCATCAG | AGTCAGTCAGCC | GGATTAGATACCCTAGTAGTC |
| (SEQ ID NO: 125) | CCTACGGGAGGCATCAG | GCAGATCTCG | CCTACGGGAGGCATCAG | AGTCAGTCAGCC | GGATTAGATACCCTAGTAGTC |
| (SEQ ID NO: 126) | CCTACGGGAGGCATCAG | GCAGATCTCG | CCTACGGGAGGCATCAG | AGTCAGTCAGCC | GGATTAGATACCCTAGTAGTC |
| (SEQ ID NO: 127) | CCTACGGGAGGCATCAG | GCAGATCTCG | CCTACGGGAGGCATCAG | AGTCAGTCAGCC | GGATTAGATACCCTAGTAGTC |
| (SEQ ID NO: 128) | CCTACGGGAGGCATCAG | GCAGATCTCG | CCTACGGGAGGCATCAG | AGTCAGTCAGCC | GGATTAGATACCCTAGTAGTC |
| (SEQ ID NO: 129) | CCTACGGGAGGCATCAG | GCAGATCTCG | CCTACGGGAGGCATCAG | AGTCAGTCAGCC | GGATTAGATACCCTAGTAGTC |
| (SEQ ID NO: 130) | CCTACGGGAGGCATCAG | GCAGATCTCG | CCTACGGGAGGCATCAG | AGTCAGTCAGCC | GGATTAGATACCCTAGTAGTC |
| (SEQ ID NO: 131) | CCTACGGGAGGCATCAG | GCAGATCTCG | CCTACGGGAGGCATCAG | AGTCAGTCAGCC | GGATTAGATACCCTAGTAGTC |
| (SEQ ID NO: 132) | CCTACGGGAGGCATCAG | GCAGATCTCG | CCTACGGGAGGCATCAG | AGTCAGTCAGCC | GGATTAGATACCCTAGTAGTC |
| (SEQ ID NO: 133) | CCTACGGGAGGCATCAG | GCAGATCTCG | CCTACGGGAGGCATCAG | AGTCAGTCAGCC | GGATTAGATACCCTAGTAGTC |
| (SEQ ID NO: 134) | CCTACGGGAGGCATCAG | GCAGATCTCG | CCTACGGGAGGCATCAG | AGTCAGTCAGCC | GGATTAGATACCCTAGTAGTC |
| (SEQ ID NO: 135) | CCTACGGGAGGCATCAG | GCAGATCTCG | CCTACGGGAGGCATCAG | AGTCAGTCAGCC | GGATTAGATACCCTAGTAGTC |
| (SEQ ID NO: 136) | CCTACGGGAGGCATCAG | GCAGATCTCG | CCTACGGGAGGCATCAG | AGTCAGTCAGCC | GGATTAGATACCCTAGTAGTC |
| (SEQ ID NO: 137) | CCTACGGGAGGCATCAG | GCAGATCTCG | CCTACGGGAGGCATCAG | AGTCAGTCAGCC | GGATTAGATACCCTAGTAGTC |
| (SEQ ID NO: 138) | CCTACGGGAGGCATCAG | GCAGATCTCG | CCTACGGGAGGCATCAG | AGTCAGTCAGCC | GGATTAGATACCCTAGTAGTC |
| (SEQ ID NO: 139) | CCTACGGGAGGCATCAG | GCAGATCTCG | CCTACGGGAGGCATCAG | AGTCAGTCAGCC | GGATTAGATACCCTAGTAGTC |
| (SEQ ID NO: 140) | CCTACGGGAGGCATCAG | GCAGATCTCG | CCTACGGGAGGCATCAG | AGTCAGTCAGCC | GGATTAGATACCCTAGTAGTC |
| (SEQ ID NO: 141) | CCTACGGGAGGCATCAG | GCAGATCTCG | CCTACGGGAGGCATCAG | AGTCAGTCAGCC | GGATTAGATACCCTAGTAGTC |
| (SEQ ID NO: 142) | CCTACGGGAGGCATCAG | GCAGATCTCG | CCTACGGGAGGCATCAG | AGTCAGTCAGCC | GGATTAGATACCCTAGTAGTC |
| (SEQ ID NO: 143) | CCTACGGGAGGCATCAG | GCAGATCTCG | CCTACGGGAGGCATCAG | AGTCAGTCAGCC | GGATTAGATACCCTAGTAGTC |
| (SEQ ID NO: 144) | CCTACGGGAGGCATCAG | GCAGATCTCG | CCTACGGGAGGCATCAG | AGTCAGTCAGCC | GGATTAGATACCCTAGTAGTC |
| (SEQ ID NO: 145) | CCTACGGGAGGCATCAG | GCAGATCTCG | CCTACGGGAGGCATCAG | AGTCAGTCAGCC | GGATTAGATACCCTAGTAGTC |
| (SEQ ID NO: 146) | CCTACGGGAGGCATCAG | GCAGATCTCG | CCTACGGGAGGCATCAG | AGTCAGTCAGCC | GGATTAGATACCCTAGTAGTC |
| (SEQ ID NO: 147) | CCTACGGGAGGCATCAG | GCAGATCTCG | CCTACGGGAGGCATCAG | AGTCAGTCAGCC | GGATTAGATACCCTAGTAGTC |
| (SEQ ID NO: 148) | CCTACGGGAGGCATCAG | GCAGATCTCG | CCTACGGGAGGCATCAG | AGTCAGTCAGCC | GGATTAGATACCCTAGTAGTC |
| (SEQ ID NO: 149) | CCTACGGGAGGCATCAG | GCAGATCTCG | CCTACGGGAGGCATCAG | AGTCAGTCAGCC | GGATTAGATACCCTAGTAGTC |
| (SEQ ID NO: 150) | CCTACGGGAGGCATCAG | GCAGATCTCG | CCTACGGGAGGCATCAG | AGTCAGTCAGCC | GGATTAGATACCCTAGTAGTC |

TABLE 2-continued

| | forward primer binding site fragment | 5' universal sequence fragment | barcode sequence fragment | 3' universal sequence fragment | reverse primer binding site fragment |
|---|---|---|---|---|---|
| (SEQ ID NO: 151) | CCTACGGGAGGCATCAG | GCAGATCTCG | CCTACGGGAGGCATCAG | AGTCAGTCAGCC | GGATTAGATACCCTAGTAGTC |
| (SEQ ID NO: 152) | CCTACGGGAGGCATCAG | GCAGATCTCG | CCTACGGGAGGCATCAG | AGTCAGTCAGCC | GGATTAGATACCCTAGTAGTC |
| (SEQ ID NO: 153) | CCTACGGGAGGCATCAG | GCAGATCTCG | CCTACGGGAGGCATCAG | AGTCAGTCAGCC | GGATTAGATACCCTAGTAGTC |
| (SEQ ID NO: 154) | CCTACGGGAGGCATCAG | GCAGATCTCG | CCTACGGGAGGCATCAG | AGTCAGTCAGCC | GGATTAGATACCCTAGTAGTC |
| (SEQ ID NO: 155) | CCTACGGGAGGCATCAG | GCAGATCTCG | CCTACGGGAGGCATCAG | AGTCAGTCAGCC | GGATTAGATACCCTAGTAGTC |
| (SEQ ID NO: 156) | CCTACGGGAGGCATCAG | GCAGATCTCG | CCTACGGGAGGCATCAG | AGTCAGTCAGCC | GGATTAGATACCCTAGTAGTC |
| (SEQ ID NO: 157) | CCTACGGGAGGCATCAG | GCAGATCTCG | CCTACGGGAGGCATCAG | AGTCAGTCAGCC | GGATTAGATACCCTAGTAGTC |
| (SEQ ID NO: 158) | CCTACGGGAGGCATCAG | GCAGATCTCG | CCTACGGGAGGCATCAG | AGTCAGTCAGCC | GGATTAGATACCCTAGTAGTC |
| (SEQ ID NO: 159) | CCTACGGGAGGCATCAG | GCAGATCTCG | CCTACGGGAGGCATCAG | AGTCAGTCAGCC | GGATTAGATACCCTAGTAGTC |
| (SEQ ID NO: 160) | CCTACGGGAGGCATCAG | GCAGATCTCG | CCTACGGGAGGCATCAG | AGTCAGTCAGCC | GGATTAGATACCCTAGTAGTC |
| (SEQ ID NO: 161) | CCTACGGGAGGCATCAG | GCAGATCTCG | CCTACGGGAGGCATCAG | AGTCAGTCAGCC | GGATTAGATACCCTAGTAGTC |
| (SEQ ID NO: 162) | CCTACGGGAGGCATCAG | GCAGATCTCG | CCTACGGGAGGCATCAG | AGTCAGTCAGCC | GGATTAGATACCCTAGTAGTC |
| (SEQ ID NO: 163) | CCTACGGGAGGCATCAG | GCAGATCTCG | CCTACGGGAGGCATCAG | AGTCAGTCAGCC | GGATTAGATACCCTAGTAGTC |
| (SEQ ID NO: 164) | CCTACGGGAGGCATCAG | GCAGATCTCG | CCTACGGGAGGCATCAG | AGTCAGTCAGCC | GGATTAGATACCCTAGTAGTC |
| (SEQ ID NO: 165) | CCTACGGGAGGCATCAG | GCAGATCTCG | CCTACGGGAGGCATCAG | AGTCAGTCAGCC | GGATTAGATACCCTAGTAGTC |
| (SEQ ID NO: 166) | CCTACGGGAGGCATCAG | GCAGATCTCG | CCTACGGGAGGCATCAG | AGTCAGTCAGCC | GGATTAGATACCCTAGTAGTC |
| (SEQ ID NO: 167) | CCTACGGGAGGCATCAG | GCAGATCTCG | CCTACGGGAGGCATCAG | AGTCAGTCAGCC | GGATTAGATACCCTAGTAGTC |
| (SEQ ID NO: 168) | CCTACGGGAGGCATCAG | GCAGATCTCG | CCTACGGGAGGCATCAG | AGTCAGTCAGCC | GGATTAGATACCCTAGTAGTC |
| (SEQ ID NO: 169) | CCTACGGGAGGCATCAG | GCAGATCTCG | CCTACGGGAGGCATCAG | AGTCAGTCAGCC | GGATTAGATACCCTAGTAGTC |
| (SEQ ID NO: 170) | CCTACGGGAGGCATCAG | GCAGATCTCG | CCTACGGGAGGCATCAG | AGTCAGTCAGCC | GGATTAGATACCCTAGTAGTC |
| (SEQ ID NO: 171) | CCTACGGGAGGCATCAG | GCAGATCTCG | CCTACGGGAGGCATCAG | AGTCAGTCAGCC | GGATTAGATACCCTAGTAGTC |
| (SEQ ID NO: 172) | CCTACGGGAGGCATCAG | GCAGATCTCG | CCTACGGGAGGCATCAG | AGTCAGTCAGCC | GGATTAGATACCCTAGTAGTC |
| (SEQ ID NO: 173) | CCTACGGGAGGCATCAG | GCAGATCTCG | CCTACGGGAGGCATCAG | AGTCAGTCAGCC | GGATTAGATACCCTAGTAGTC |
| (SEQ ID NO: 174) | CCTACGGGAGGCATCAG | GCAGATCTCG | CCTACGGGAGGCATCAG | AGTCAGTCAGCC | GGATTAGATACCCTAGTAGTC |
| (SEQ ID NO: 175) | CCTACGGGAGGCATCAG | GCAGATCTCG | CCTACGGGAGGCATCAG | AGTCAGTCAGCC | GGATTAGATACCCTAGTAGTC |
| (SEQ ID NO: 176) | CCTACGGGAGGCATCAG | GCAGATCTCG | CCTACGGGAGGCATCAG | AGTCAGTCAGCC | GGATTAGATACCCTAGTAGTC |
| (SEQ ID NO: 177) | CCTACGGGAGGCATCAG | GCAGATCTCG | CCTACGGGAGGCATCAG | AGTCAGTCAGCC | GGATTAGATACCCTAGTAGTC |
| (SEQ ID NO: 178) | CCTACGGGAGGCATCAG | GCAGATCTCG | CCTACGGGAGGCATCAG | AGTCAGTCAGCC | GGATTAGATACCCTAGTAGTC |
| (SEQ ID NO: 179) | CCTACGGGAGGCATCAG | GCAGATCTCG | CCTACGGGAGGCATCAG | AGTCAGTCAGCC | GGATTAGATACCCTAGTAGTC |
| (SEQ ID NO: 180) | CCTACGGGAGGCATCAG | GCAGATCTCG | CCTACGGGAGGCATCAG | AGTCAGTCAGCC | GGATTAGATACCCTAGTAGTC |
| (SEQ ID NO: 181) | CCTACGGGAGGCATCAG | GCAGATCTCG | CCTACGGGAGGCATCAG | AGTCAGTCAGCC | GGATTAGATACCCTAGTAGTC |
| (SEQ ID NO: 182) | CCTACGGGAGGCATCAG | GCAGATCTCG | CCTACGGGAGGCATCAG | AGTCAGTCAGCC | GGATTAGATACCCTAGTAGTC |
| (SEQ ID NO: 183) | CCTACGGGAGGCATCAG | GCAGATCTCG | CCTACGGGAGGCATCAG | AGTCAGTCAGCC | GGATTAGATACCCTAGTAGTC |
| (SEQ ID NO: 184) | CCTACGGGAGGCATCAG | GCAGATCTCG | CCTACGGGAGGCATCAG | AGTCAGTCAGCC | GGATTAGATACCCTAGTAGTC |
| (SEQ ID NO: 185) | CCTACGGGAGGCATCAG | GCAGATCTCG | CCTACGGGAGGCATCAG | AGTCAGTCAGCC | GGATTAGATACCCTAGTAGTC |
| (SEQ ID NO: 186) | CCTACGGGAGGCATCAG | GCAGATCTCG | CCTACGGGAGGCATCAG | AGTCAGTCAGCC | GGATTAGATACCCTAGTAGTC |
| (SEQ ID NO: 187) | CCTACGGGAGGCATCAG | GCAGATCTCG | CCTACGGGAGGCATCAG | AGTCAGTCAGCC | GGATTAGATACCCTAGTAGTC |
| (SEQ ID NO: 188) | CCTACGGGAGGCATCAG | GCAGATCTCG | CCTACGGGAGGCATCAG | AGTCAGTCAGCC | GGATTAGATACCCTAGTAGTC |

TABLE 2-continued

| | forward primer binding site fragment | 5' universal sequence fragment | barcode sequence fragment | 3' universal sequence fragment | reverse primer binding site fragment |
|---|---|---|---|---|---|
| (SEQ ID NO: 189) | CCTACGGGAGGCATCAG | GCAGATCTCG | CCTACGGGAGGCATCAG | AGTCAGTCAGCC | GGATTAGATACCCTAGTAGTC |
| (SEQ ID NO: 190) | CCTACGGGAGGCATCAG | GCAGATCTCG | CCTACGGGAGGCATCAG | AGTCAGTCAGCC | GGATTAGATACCCTAGTAGTC |
| (SEQ ID NO: 191) | CCTACGGGAGGCATCAG | GCAGATCTCG | CCTACGGGAGGCATCAG | AGTCAGTCAGCC | GGATTAGATACCCTAGTAGTC |
| (SEQ ID NO: 192) | CCTACGGGAGGCATCAG | GCAGATCTCG | CCTACGGGAGGCATCAG | AGTCAGTCAGCC | GGATTAGATACCCTAGTAGTC |
| (SEQ ID NO: 193) | CCTACGGGAGGCATCAG | GCAGATCTCG | CCTACGGGAGGCATCAG | AGTCAGTCAGCC | GGATTAGATACCCTAGTAGTC |
| (SEQ ID NO: 194) | CCTACGGGAGGCATCAG | GCAGATCTCG | CCTACGGGAGGCATCAG | AGTCAGTCAGCC | GGATTAGATACCCTAGTAGTC |
| (SEQ ID NO: 195) | CCTACGGGAGGCATCAG | GCAGATCTCG | CCTACGGGAGGCATCAG | AGTCAGTCAGCC | GGATTAGATACCCTAGTAGTC |
| (SEQ ID NO: 196) | CCTACGGGAGGCATCAG | GCAGATCTCG | CCTACGGGAGGCATCAG | AGTCAGTCAGCC | GGATTAGATACCCTAGTAGTC |
| (SEQ ID NO: 197) | CCTACGGGAGGCATCAG | GCAGATCTCG | CCTACGGGAGGCATCAG | AGTCAGTCAGCC | GGATTAGATACCCTAGTAGTC |
| (SEQ ID NO: 198) | CCTACGGGAGGCATCAG | GCAGATCTCG | CCTACGGGAGGCATCAG | AGTCAGTCAGCC | GGATTAGATACCCTAGTAGTC |
| (SEQ ID NO: 199) | CCTACGGGAGGCATCAG | GCAGATCTCG | CCTACGGGAGGCATCAG | AGTCAGTCAGCC | GGATTAGATACCCTAGTAGTC |
| (SEQ ID NO: 200) | CCTACGGGAGGCATCAG | GCAGATCTCG | CCTACGGGAGGCATCAG | AGTCAGTCAGCC | GGATTAGATACCCTAGTAGTC |
| (SEQ ID NO: 201) | CCTACGGGAGGCATCAG | GCAGATCTCG | CCTACGGGAGGCATCAG | AGTCAGTCAGCC | GGATTAGATACCCTAGTAGTC |
| (SEQ ID NO: 202) | CCTACGGGAGGCATCAG | GCAGATCTCG | CCTACGGGAGGCATCAG | AGTCAGTCAGCC | GGATTAGATACCCTAGTAGTC |
| (SEQ ID NO: 203) | CCTACGGGAGGCATCAG | GCAGATCTCG | CCTACGGGAGGCATCAG | AGTCAGTCAGCC | GGATTAGATACCCTAGTAGTC |
| (SEQ ID NO: 204) | CCTACGGGAGGCATCAG | GCAGATCTCG | CCTACGGGAGGCATCAG | AGTCAGTCAGCC | GGATTAGATACCCTAGTAGTC |
| (SEQ ID NO: 205) | CCTACGGGAGGCATCAG | GCAGATCTCG | CCTACGGGAGGCATCAG | AGTCAGTCAGCC | GGATTAGATACCCTAGTAGTC |
| (SEQ ID NO: 206) | CCTACGGGAGGCATCAG | GCAGATCTCG | CCTACGGGAGGCATCAG | AGTCAGTCAGCC | GGATTAGATACCCTAGTAGTC |
| (SEQ ID NO: 207) | CCTACGGGAGGCATCAG | GCAGATCTCG | CCTACGGGAGGCATCAG | AGTCAGTCAGCC | GGATTAGATACCCTAGTAGTC |
| (SEQ ID NO: 208) | CCTACGGGAGGCATCAG | GCAGATCTCG | CCTACGGGAGGCATCAG | AGTCAGTCAGCC | GGATTAGATACCCTAGTAGTC |
| (SEQ ID NO: 209) | CCTACGGGAGGCATCAG | GCAGATCTCG | CCTACGGGAGGCATCAG | AGTCAGTCAGCC | GGATTAGATACCCTAGTAGTC |
| (SEQ ID NO: 210) | CCTACGGGAGGCATCAG | GCAGATCTCG | CCTACGGGAGGCATCAG | AGTCAGTCAGCC | GGATTAGATACCCTAGTAGTC |
| (SEQ ID NO: 211) | CCTACGGGAGGCATCAG | GCAGATCTCG | CCTACGGGAGGCATCAG | AGTCAGTCAGCC | GGATTAGATACCCTAGTAGTC |
| (SEQ ID NO: 212) | CCTACGGGAGGCATCAG | GCAGATCTCG | CCTACGGGAGGCATCAG | AGTCAGTCAGCC | GGATTAGATACCCTAGTAGTC |
| (SEQ ID NO: 213) | CCTACGGGAGGCATCAG | GCAGATCTCG | CCTACGGGAGGCATCAG | AGTCAGTCAGCC | GGATTAGATACCCTAGTAGTC |
| (SEQ ID NO: 214) | CCTACGGGAGGCATCAG | GCAGATCTCG | CCTACGGGAGGCATCAG | AGTCAGTCAGCC | GGATTAGATACCCTAGTAGTC |
| (SEQ ID NO: 215) | CCTACGGGAGGCATCAG | GCAGATCTCG | CCTACGGGAGGCATCAG | AGTCAGTCAGCC | GGATTAGATACCCTAGTAGTC |
| (SEQ ID NO: 216) | CCTACGGGAGGCATCAG | GCAGATCTCG | CCTACGGGAGGCATCAG | AGTCAGTCAGCC | GGATTAGATACCCTAGTAGTC |
| (SEQ ID NO: 217) | CCTACGGGAGGCATCAG | GCAGATCTCG | CCTACGGGAGGCATCAG | AGTCAGTCAGCC | GGATTAGATACCCTAGTAGTC |
| (SEQ ID NO: 218) | CCTACGGGAGGCATCAG | GCAGATCTCG | CCTACGGGAGGCATCAG | AGTCAGTCAGCC | GGATTAGATACCCTAGTAGTC |
| (SEQ ID NO: 219) | CCTACGGGAGGCATCAG | GCAGATCTCG | CCTACGGGAGGCATCAG | AGTCAGTCAGCC | GGATTAGATACCCTAGTAGTC |
| (SEQ ID NO: 220) | CCTACGGGAGGCATCAG | GCAGATCTCG | CCTACGGGAGGCATCAG | AGTCAGTCAGCC | GGATTAGATACCCTAGTAGTC |
| (SEQ ID NO: 221) | CCTACGGGAGGCATCAG | GCAGATCTCG | CCTACGGGAGGCATCAG | AGTCAGTCAGCC | GGATTAGATACCCTAGTAGTC |
| (SEQ ID NO: 222) | CCTACGGGAGGCATCAG | GCAGATCTCG | CCTACGGGAGGCATCAG | AGTCAGTCAGCC | GGATTAGATACCCTAGTAGTC |
| (SEQ ID NO: 223) | CCTACGGGAGGCATCAG | GCAGATCTCG | CCTACGGGAGGCATCAG | AGTCAGTCAGCC | GGATTAGATACCCTAGTAGTC |
| (SEQ ID NO: 224) | CCTACGGGAGGCATCAG | GCAGATCTCG | CCTACGGGAGGCATCAG | AGTCAGTCAGCC | GGATTAGATACCCTAGTAGTC |
| (SEQ ID NO: 225) | CCTACGGGAGGCATCAG | GCAGATCTCG | CCTACGGGAGGCATCAG | AGTCAGTCAGCC | GGATTAGATACCCTAGTAGTC |

TABLE 2-continued

| | forward primer binding site fragment | 5' universal sequence fragment | barcode sequence fragment | 3' universal sequence fragment | reverse primer binding site fragment |
|---|---|---|---|---|---|
| (SEQ ID NO: 226) | CCTACGGGAGGCATCAG | GCAGATCTCG | CCTACGGGAGGCATCAG | AGTCAGTCAGCC | GGATTAGATACCCTAGTAGTC |
| (SEQ ID NO: 227) | CCTACGGGAGGCATCAG | GCAGATCTCG | CCTACGGGAGGCATCAG | AGTCAGTCAGCC | GGATTAGATACCCTAGTAGTC |
| (SEQ ID NO: 228) | CCTACGGGAGGCATCAG | GCAGATCTCG | CCTACGGGAGGCATCAG | AGTCAGTCAGCC | GGATTAGATACCCTAGTAGTC |
| (SEQ ID NO: 229) | CCTACGGGAGGCATCAG | GCAGATCTCG | CCTACGGGAGGCATCAG | AGTCAGTCAGCC | GGATTAGATACCCTAGTAGTC |
| (SEQ ID NO: 230) | CCTACGGGAGGCATCAG | GCAGATCTCG | CCTACGGGAGGCATCAG | AGTCAGTCAGCC | GGATTAGATACCCTAGTAGTC |
| (SEQ ID NO: 231) | CCTACGGGAGGCATCAG | GCAGATCTCG | CCTACGGGAGGCATCAG | AGTCAGTCAGCC | GGATTAGATACCCTAGTAGTC |
| (SEQ ID NO: 232) | CCTACGGGAGGCATCAG | GCAGATCTCG | CCTACGGGAGGCATCAG | AGTCAGTCAGCC | GGATTAGATACCCTAGTAGTC |
| (SEQ ID NO: 233) | CCTACGGGAGGCATCAG | GCAGATCTCG | CCTACGGGAGGCATCAG | AGTCAGTCAGCC | GGATTAGATACCCTAGTAGTC |
| (SEQ ID NO: 234) | CCTACGGGAGGCATCAG | GCAGATCTCG | CCTACGGGAGGCATCAG | AGTCAGTCAGCC | GGATTAGATACCCTAGTAGTC |
| (SEQ ID NO: 235) | CCTACGGGAGGCATCAG | GCAGATCTCG | CCTACGGGAGGCATCAG | AGTCAGTCAGCC | GGATTAGATACCCTAGTAGTC |
| (SEQ ID NO: 236) | CCTACGGGAGGCATCAG | GCAGATCTCG | CCTACGGGAGGCATCAG | AGTCAGTCAGCC | GGATTAGATACCCTAGTAGTC |
| (SEQ ID NO: 237) | CCTACGGGAGGCATCAG | GCAGATCTCG | CCTACGGGAGGCATCAG | AGTCAGTCAGCC | GGATTAGATACCCTAGTAGTC |
| (SEQ ID NO: 238) | CCTACGGGAGGCATCAG | GCAGATCTCG | CCTACGGGAGGCATCAG | AGTCAGTCAGCC | GGATTAGATACCCTAGTAGTC |
| (SEQ ID NO: 239) | CCTACGGGAGGCATCAG | GCAGATCTCG | CCTACGGGAGGCATCAG | AGTCAGTCAGCC | GGATTAGATACCCTAGTAGTC |
| (SEQ ID NO: 240) | CCTACGGGAGGCATCAG | GCAGATCTCG | CCTACGGGAGGCATCAG | AGTCAGTCAGCC | GGATTAGATACCCTAGTAGTC |
| (SEQ ID NO: 241) | CCTACGGGAGGCATCAG | GCAGATCTCG | CCTACGGGAGGCATCAG | AGTCAGTCAGCC | GGATTAGATACCCTAGTAGTC |
| (SEQ ID NO: 242) | CCTACGGGAGGCATCAG | GCAGATCTCG | CCTACGGGAGGCATCAG | AGTCAGTCAGCC | GGATTAGATACCCTAGTAGTC |
| (SEQ ID NO: 243) | CCTACGGGAGGCATCAG | GCAGATCTCG | CCTACGGGAGGCATCAG | AGTCAGTCAGCC | GGATTAGATACCCTAGTAGTC |
| (SEQ ID NO: 244) | CCTACGGGAGGCATCAG | GCAGATCTCG | CCTACGGGAGGCATCAG | AGTCAGTCAGCC | GGATTAGATACCCTAGTAGTC |
| (SEQ ID NO: 245) | CCTACGGGAGGCATCAG | GCAGATCTCG | CCTACGGGAGGCATCAG | AGTCAGTCAGCC | GGATTAGATACCCTAGTAGTC |
| (SEQ ID NO: 246) | CCTACGGGAGGCATCAG | GCAGATCTCG | CCTACGGGAGGCATCAG | AGTCAGTCAGCC | GGATTAGATACCCTAGTAGTC |
| (SEQ ID NO: 247) | CCTACGGGAGGCATCAG | GCAGATCTCG | CCTACGGGAGGCATCAG | AGTCAGTCAGCC | GGATTAGATACCCTAGTAGTC |
| (SEQ ID NO: 248) | CCTACGGGAGGCATCAG | GCAGATCTCG | CCTACGGGAGGCATCAG | AGTCAGTCAGCC | GGATTAGATACCCTAGTAGTC |
| (SEQ ID NO: 249) | CCTACGGGAGGCATCAG | GCAGATCTCG | CCTACGGGAGGCATCAG | AGTCAGTCAGCC | GGATTAGATACCCTAGTAGTC |
| (SEQ ID NO: 250) | CCTACGGGAGGCATCAG | GCAGATCTCG | CCTACGGGAGGCATCAG | AGTCAGTCAGCC | GGATTAGATACCCTAGTAGTC |
| (SEQ ID NO: 251) | CCTACGGGAGGCATCAG | GCAGATCTCG | CCTACGGGAGGCATCAG | AGTCAGTCAGCC | GGATTAGATACCCTAGTAGTC |
| (SEQ ID NO: 252) | CCTACGGGAGGCATCAG | GCAGATCTCG | CCTACGGGAGGCATCAG | AGTCAGTCAGCC | GGATTAGATACCCTAGTAGTC |
| (SEQ ID NO: 253) | CCTACGGGAGGCATCAG | GCAGATCTCG | CCTACGGGAGGCATCAG | AGTCAGTCAGCC | GGATTAGATACCCTAGTAGTC |
| (SEQ ID NO: 254) | CCTACGGGAGGCATCAG | GCAGATCTCG | CCTACGGGAGGCATCAG | AGTCAGTCAGCC | GGATTAGATACCCTAGTAGTC |
| (SEQ ID NO: 255) | CCTACGGGAGGCATCAG | GCAGATCTCG | CCTACGGGAGGCATCAG | AGTCAGTCAGCC | GGATTAGATACCCTAGTAGTC |
| (SEQ ID NO: 256) | CCTACGGGAGGCATCAG | GCAGATCTCG | CCTACGGGAGGCATCAG | AGTCAGTCAGCC | GGATTAGATACCCTAGTAGTC |
| (SEQ ID NO: 257) | CCTACGGGAGGCATCAG | GCAGATCTCG | CCTACGGGAGGCATCAG | AGTCAGTCAGCC | GGATTAGATACCCTAGTAGTC |
| (SEQ ID NO: 258) | CCTACGGGAGGCATCAG | GCAGATCTCG | CCTACGGGAGGCATCAG | AGTCAGTCAGCC | GGATTAGATACCCTAGTAGTC |
| (SEQ ID NO: 259) | CCTACGGGAGGCATCAG | GCAGATCTCG | CCTACGGGAGGCATCAG | AGTCAGTCAGCC | GGATTAGATACCCTAGTAGTC |
| (SEQ ID NO: 260) | CCTACGGGAGGCATCAG | GCAGATCTCG | CCTACGGGAGGCATCAG | AGTCAGTCAGCC | GGATTAGATACCCTAGTAGTC |
| (SEQ ID NO: 261) | CCTACGGGAGGCATCAG | GCAGATCTCG | CCTACGGGAGGCATCAG | AGTCAGTCAGCC | GGATTAGATACCCTAGTAGTC |
| (SEQ ID NO: 262) | CCTACGGGAGGCATCAG | GCAGATCTCG | CCTACGGGAGGCATCAG | AGTCAGTCAGCC | GGATTAGATACCCTAGTAGTC |
| (SEQ ID NO: 263) | CCTACGGGAGGCATCAG | GCAGATCTCG | CCTACGGGAGGCATCAG | AGTCAGTCAGCC | GGATTAGATACCCTAGTAGTC |

TABLE 2-continued

| | forward primer binding site fragment | 5' universal sequence fragment | barcode sequence fragment | 3' universal sequence fragment | reverse primer binding site fragment |
|---|---|---|---|---|---|
| (SEQ ID NO: 264) | CCTACGGGAGGCATCAG | GCAGATCTCG | CCTACGGGAGGCATCAG | AGTCAGTCAGCC | GGATTAGATACCCTAGTAGTC |
| (SEQ ID NO: 265) | CCTACGGGAGGCATCAG | GCAGATCTCG | CCTACGGGAGGCATCAG | AGTCAGTCAGCC | GGATTAGATACCCTAGTAGTC |
| (SEQ ID NO: 266) | CCTACGGGAGGCATCAG | GCAGATCTCG | CCTACGGGAGGCATCAG | AGTCAGTCAGCC | GGATTAGATACCCTAGTAGTC |
| (SEQ ID NO: 267) | CCTACGGGAGGCATCAG | GCAGATCTCG | CCTACGGGAGGCATCAG | AGTCAGTCAGCC | GGATTAGATACCCTAGTAGTC |
| (SEQ ID NO: 268) | CCTACGGGAGGCATCAG | GCAGATCTCG | CCTACGGGAGGCATCAG | AGTCAGTCAGCC | GGATTAGATACCCTAGTAGTC |
| (SEQ ID NO: 269) | CCTACGGGAGGCATCAG | GCAGATCTCG | CCTACGGGAGGCATCAG | AGTCAGTCAGCC | GGATTAGATACCCTAGTAGTC |
| (SEQ ID NO: 270) | CCTACGGGAGGCATCAG | GCAGATCTCG | CCTACGGGAGGCATCAG | AGTCAGTCAGCC | GGATTAGATACCCTAGTAGTC |
| (SEQ ID NO: 271) | CCTACGGGAGGCATCAG | GCAGATCTCG | CCTACGGGAGGCATCAG | AGTCAGTCAGCC | GGATTAGATACCCTAGTAGTC |
| (SEQ ID NO: 272) | CCTACGGGAGGCATCAG | GCAGATCTCG | CCTACGGGAGGCATCAG | AGTCAGTCAGCC | GGATTAGATACCCTAGTAGTC |
| (SEQ ID NO: 273) | CCTACGGGAGGCATCAG | GCAGATCTCG | CCTACGGGAGGCATCAG | AGTCAGTCAGCC | GGATTAGATACCCTAGTAGTC |
| (SEQ ID NO: 274) | CCTACGGGAGGCATCAG | GCAGATCTCG | CCTACGGGAGGCATCAG | AGTCAGTCAGCC | GGATTAGATACCCTAGTAGTC |
| (SEQ ID NO: 275) | CCTACGGGAGGCATCAG | GCAGATCTCG | CCTACGGGAGGCATCAG | AGTCAGTCAGCC | GGATTAGATACCCTAGTAGTC |
| (SEQ ID NO: 276) | CCTACGGGAGGCATCAG | GCAGATCTCG | CCTACGGGAGGCATCAG | AGTCAGTCAGCC | GGATTAGATACCCTAGTAGTC |
| (SEQ ID NO: 277) | CCTACGGGAGGCATCAG | GCAGATCTCG | CCTACGGGAGGCATCAG | AGTCAGTCAGCC | GGATTAGATACCCTAGTAGTC |
| (SEQ ID NO: 278) | CCTACGGGAGGCATCAG | GCAGATCTCG | CCTACGGGAGGCATCAG | AGTCAGTCAGCC | GGATTAGATACCCTAGTAGTC |
| (SEQ ID NO: 279) | CCTACGGGAGGCATCAG | GCAGATCTCG | CCTACGGGAGGCATCAG | AGTCAGTCAGCC | GGATTAGATACCCTAGTAGTC |
| (SEQ ID NO: 280) | CCTACGGGAGGCATCAG | GCAGATCTCG | CCTACGGGAGGCATCAG | AGTCAGTCAGCC | GGATTAGATACCCTAGTAGTC |
| (SEQ ID NO: 281) | CCTACGGGAGGCATCAG | GCAGATCTCG | CCTACGGGAGGCATCAG | AGTCAGTCAGCC | GGATTAGATACCCTAGTAGTC |
| (SEQ ID NO: 282) | CCTACGGGAGGCATCAG | GCAGATCTCG | CCTACGGGAGGCATCAG | AGTCAGTCAGCC | GGATTAGATACCCTAGTAGTC |
| (SEQ ID NO: 283) | CCTACGGGAGGCATCAG | GCAGATCTCG | CCTACGGGAGGCATCAG | AGTCAGTCAGCC | GGATTAGATACCCTAGTAGTC |
| (SEQ ID NO: 284) | CCTACGGGAGGCATCAG | GCAGATCTCG | CCTACGGGAGGCATCAG | AGTCAGTCAGCC | GGATTAGATACCCTAGTAGTC |
| (SEQ ID NO: 285) | CCTACGGGAGGCATCAG | GCAGATCTCG | CCTACGGGAGGCATCAG | AGTCAGTCAGCC | GGATTAGATACCCTAGTAGTC |
| (SEQ ID NO: 286) | CCTACGGGAGGCATCAG | GCAGATCTCG | CCTACGGGAGGCATCAG | AGTCAGTCAGCC | GGATTAGATACCCTAGTAGTC |
| (SEQ ID NO: 287) | CCTACGGGAGGCATCAG | GCAGATCTCG | CCTACGGGAGGCATCAG | AGTCAGTCAGCC | GGATTAGATACCCTAGTAGTC |
| (SEQ ID NO: 288) | CCTACGGGAGGCATCAG | GCAGATCTCG | CCTACGGGAGGCATCAG | AGTCAGTCAGCC | GGATTAGATACCCTAGTAGTC |
| (SEQ ID NO: 289) | CCTACGGGAGGCATCAG | GCAGATCTCG | CCTACGGGAGGCATCAG | AGTCAGTCAGCC | GGATTAGATACCCTAGTAGTC |
| (SEQ ID NO: 290) | CCTACGGGAGGCATCAG | GCAGATCTCG | CCTACGGGAGGCATCAG | AGTCAGTCAGCC | GGATTAGATACCCTAGTAGTC |
| (SEQ ID NO: 291) | CCTACGGGAGGCATCAG | GCAGATCTCG | CCTACGGGAGGCATCAG | AGTCAGTCAGCC | GGATTAGATACCCTAGTAGTC |
| (SEQ ID NO: 292) | CCTACGGGAGGCATCAG | GCAGATCTCG | CCTACGGGAGGCATCAG | AGTCAGTCAGCC | GGATTAGATACCCTAGTAGTC |
| (SEQ ID NO: 293) | CCTACGGGAGGCATCAG | GCAGATCTCG | CCTACGGGAGGCATCAG | AGTCAGTCAGCC | GGATTAGATACCCTAGTAGTC |
| (SEQ ID NO: 294) | CCTACGGGAGGCATCAG | GCAGATCTCG | CCTACGGGAGGCATCAG | AGTCAGTCAGCC | GGATTAGATACCCTAGTAGTC |
| (SEQ ID NO: 295) | CCTACGGGAGGCATCAG | GCAGATCTCG | CCTACGGGAGGCATCAG | AGTCAGTCAGCC | GGATTAGATACCCTAGTAGTC |
| (SEQ ID NO: 296) | CCTACGGGAGGCATCAG | GCAGATCTCG | CCTACGGGAGGCATCAG | AGTCAGTCAGCC | GGATTAGATACCCTAGTAGTC |
| (SEQ ID NO: 297) | CCTACGGGAGGCATCAG | GCAGATCTCG | CCTACGGGAGGCATCAG | AGTCAGTCAGCC | GGATTAGATACCCTAGTAGTC |
| (SEQ ID NO: 298) | CCTACGGGAGGCATCAG | GCAGATCTCG | CCTACGGGAGGCATCAG | AGTCAGTCAGCC | GGATTAGATACCCTAGTAGTC |
| (SEQ ID NO: 299) | CCTACGGGAGGCATCAG | GCAGATCTCG | CCTACGGGAGGCATCAG | AGTCAGTCAGCC | GGATTAGATACCCTAGTAGTC |
| (SEQ ID NO: 300) | CCTACGGGAGGCATCAG | GCAGATCTCG | CCTACGGGAGGCATCAG | AGTCAGTCAGCC | GGATTAGATACCCTAGTAGTC |

TABLE 2-continued

| | forward primer binding site fragment | 5' universal sequence fragment | barcode sequence fragment | 3' universal sequence fragment | reverse primer binding site fragment |
|---|---|---|---|---|---|
| (SEQ ID NO: 301) | CCTACGGGAGGCATCAG | GCAGATCTCG | CCTACGGGAGGCATCAG | AGTCAGTCAGCC | GGATTAGATACCCTAGTAGTC |
| (SEQ ID NO: 302) | CCTACGGGAGGCATCAG | GCAGATCTCG | CCTACGGGAGGCATCAG | AGTCAGTCAGCC | GGATTAGATACCCTAGTAGTC |
| (SEQ ID NO: 303) | CCTACGGGAGGCATCAG | GCAGATCTCG | CCTACGGGAGGCATCAG | AGTCAGTCAGCC | GGATTAGATACCCTAGTAGTC |
| (SEQ ID NO: 304) | CCTACGGGAGGCATCAG | GCAGATCTCG | CCTACGGGAGGCATCAG | AGTCAGTCAGCC | GGATTAGATACCCTAGTAGTC |
| (SEQ ID NO: 305) | CCTACGGGAGGCATCAG | GCAGATCTCG | CCTACGGGAGGCATCAG | AGTCAGTCAGCC | GGATTAGATACCCTAGTAGTC |
| (SEQ ID NO: 306) | CCTACGGGAGGCATCAG | GCAGATCTCG | CCTACGGGAGGCATCAG | AGTCAGTCAGCC | GGATTAGATACCCTAGTAGTC |
| (SEQ ID NO: 307) | CCTACGGGAGGCATCAG | GCAGATCTCG | CCTACGGGAGGCATCAG | AGTCAGTCAGCC | GGATTAGATACCCTAGTAGTC |
| (SEQ ID NO: 308) | CCTACGGGAGGCATCAG | GCAGATCTCG | CCTACGGGAGGCATCAG | AGTCAGTCAGCC | GGATTAGATACCCTAGTAGTC |
| (SEQ ID NO: 309) | CCTACGGGAGGCATCAG | GCAGATCTCG | CCTACGGGAGGCATCAG | AGTCAGTCAGCC | GGATTAGATACCCTAGTAGTC |
| (SEQ ID NO: 310) | CCTACGGGAGGCATCAG | GCAGATCTCG | CCTACGGGAGGCATCAG | AGTCAGTCAGCC | GGATTAGATACCCTAGTAGTC |
| (SEQ ID NO: 311) | CCTACGGGAGGCATCAG | GCAGATCTCG | CCTACGGGAGGCATCAG | AGTCAGTCAGCC | GGATTAGATACCCTAGTAGTC |
| (SEQ ID NO: 312) | CCTACGGGAGGCATCAG | GCAGATCTCG | CCTACGGGAGGCATCAG | AGTCAGTCAGCC | GGATTAGATACCCTAGTAGTC |
| (SEQ ID NO: 313) | CCTACGGGAGGCATCAG | GCAGATCTCG | CCTACGGGAGGCATCAG | AGTCAGTCAGCC | GGATTAGATACCCTAGTAGTC |
| (SEQ ID NO: 314) | CCTACGGGAGGCATCAG | GCAGATCTCG | CCTACGGGAGGCATCAG | AGTCAGTCAGCC | GGATTAGATACCCTAGTAGTC |
| (SEQ ID NO: 315) | CCTACGGGAGGCATCAG | GCAGATCTCG | CCTACGGGAGGCATCAG | AGTCAGTCAGCC | GGATTAGATACCCTAGTAGTC |
| (SEQ ID NO: 316) | CCTACGGGAGGCATCAG | GCAGATCTCG | CCTACGGGAGGCATCAG | AGTCAGTCAGCC | GGATTAGATACCCTAGTAGTC |
| (SEQ ID NO: 317) | CCTACGGGAGGCATCAG | GCAGATCTCG | CCTACGGGAGGCATCAG | AGTCAGTCAGCC | GGATTAGATACCCTAGTAGTC |
| (SEQ ID NO: 318) | CCTACGGGAGGCATCAG | GCAGATCTCG | CCTACGGGAGGCATCAG | AGTCAGTCAGCC | GGATTAGATACCCTAGTAGTC |
| (SEQ ID NO: 319) | CCTACGGGAGGCATCAG | GCAGATCTCG | CCTACGGGAGGCATCAG | AGTCAGTCAGCC | GGATTAGATACCCTAGTAGTC |
| (SEQ ID NO: 320) | CCTACGGGAGGCATCAG | GCAGATCTCG | CCTACGGGAGGCATCAG | AGTCAGTCAGCC | GGATTAGATACCCTAGTAGTC |
| (SEQ ID NO: 321) | CCTACGGGAGGCATCAG | GCAGATCTCG | CCTACGGGAGGCATCAG | AGTCAGTCAGCC | GGATTAGATACCCTAGTAGTC |
| (SEQ ID NO: 322) | CCTACGGGAGGCATCAG | GCAGATCTCG | CCTACGGGAGGCATCAG | AGTCAGTCAGCC | GGATTAGATACCCTAGTAGTC |
| (SEQ ID NO: 323) | CCTACGGGAGGCATCAG | GCAGATCTCG | CCTACGGGAGGCATCAG | AGTCAGTCAGCC | GGATTAGATACCCTAGTAGTC |
| (SEQ ID NO: 324) | CCTACGGGAGGCATCAG | GCAGATCTCG | CCTACGGGAGGCATCAG | AGTCAGTCAGCC | GGATTAGATACCCTAGTAGTC |
| (SEQ ID NO: 325) | CCTACGGGAGGCATCAG | GCAGATCTCG | CCTACGGGAGGCATCAG | AGTCAGTCAGCC | GGATTAGATACCCTAGTAGTC |
| (SEQ ID NO: 326) | CCTACGGGAGGCATCAG | GCAGATCTCG | CCTACGGGAGGCATCAG | AGTCAGTCAGCC | GGATTAGATACCCTAGTAGTC |
| (SEQ ID NO: 327) | CCTACGGGAGGCATCAG | GCAGATCTCG | CCTACGGGAGGCATCAG | AGTCAGTCAGCC | GGATTAGATACCCTAGTAGTC |
| (SEQ ID NO: 328) | CCTACGGGAGGCATCAG | GCAGATCTCG | CCTACGGGAGGCATCAG | AGTCAGTCAGCC | GGATTAGATACCCTAGTAGTC |
| (SEQ ID NO: 329) | CCTACGGGAGGCATCAG | GCAGATCTCG | CCTACGGGAGGCATCAG | AGTCAGTCAGCC | GGATTAGATACCCTAGTAGTC |
| (SEQ ID NO: 330) | CCTACGGGAGGCATCAG | GCAGATCTCG | CCTACGGGAGGCATCAG | AGTCAGTCAGCC | GGATTAGATACCCTAGTAGTC |
| (SEQ ID NO: 331) | CCTACGGGAGGCATCAG | GCAGATCTCG | CCTACGGGAGGCATCAG | AGTCAGTCAGCC | GGATTAGATACCCTAGTAGTC |
| (SEQ ID NO: 332) | CCTACGGGAGGCATCAG | GCAGATCTCG | CCTACGGGAGGCATCAG | AGTCAGTCAGCC | GGATTAGATACCCTAGTAGTC |
| (SEQ ID NO: 333) | CCTACGGGAGGCATCAG | GCAGATCTCG | CCTACGGGAGGCATCAG | AGTCAGTCAGCC | GGATTAGATACCCTAGTAGTC |
| (SEQ ID NO: 334) | CCTACGGGAGGCATCAG | GCAGATCTCG | CCTACGGGAGGCATCAG | AGTCAGTCAGCC | GGATTAGATACCCTAGTAGTC |
| (SEQ ID NO: 335) | CCTACGGGAGGCATCAG | GCAGATCTCG | CCTACGGGAGGCATCAG | AGTCAGTCAGCC | GGATTAGATACCCTAGTAGTC |
| (SEQ ID NO: 336) | CCTACGGGAGGCATCAG | GCAGATCTCG | CCTACGGGAGGCATCAG | AGTCAGTCAGCC | GGATTAGATACCCTAGTAGTC |
| (SEQ ID NO: 337) | CCTACGGGAGGCATCAG | GCAGATCTCG | CCTACGGGAGGCATCAG | AGTCAGTCAGCC | GGATTAGATACCCTAGTAGTC |
| (SEQ ID NO: 338) | CCTACGGGAGGCATCAG | GCAGATCTCG | CCTACGGGAGGCATCAG | AGTCAGTCAGCC | GGATTAGATACCCTAGTAGTC |

TABLE 2-continued

| | forward primer binding site fragment | 5' universal sequence fragment | barcode sequence fragment | 3' universal sequence fragment | reverse primer binding site fragment |
|---|---|---|---|---|---|
| (SEQ ID NO: 339) | CCTACGGGAGGCATCAG | GCAGATCTCG | CCTACGGGAGGCATCAG | AGTCAGTCAGCC | GGATTAGATACCCTAGTAGTC |
| (SEQ ID NO: 340) | CCTACGGGAGGCATCAG | GCAGATCTCG | CCTACGGGAGGCATCAG | AGTCAGTCAGCC | GGATTAGATACCCTAGTAGTC |
| (SEQ ID NO: 341) | CCTACGGGAGGCATCAG | GCAGATCTCG | CCTACGGGAGGCATCAG | AGTCAGTCAGCC | GGATTAGATACCCTAGTAGTC |
| (SEQ ID NO: 342) | CCTACGGGAGGCATCAG | GCAGATCTCG | CCTACGGGAGGCATCAG | AGTCAGTCAGCC | GGATTAGATACCCTAGTAGTC |
| (SEQ ID NO: 343) | CCTACGGGAGGCATCAG | GCAGATCTCG | CCTACGGGAGGCATCAG | AGTCAGTCAGCC | GGATTAGATACCCTAGTAGTC |
| (SEQ ID NO: 344) | CCTACGGGAGGCATCAG | GCAGATCTCG | CCTACGGGAGGCATCAG | AGTCAGTCAGCC | GGATTAGATACCCTAGTAGTC |
| (SEQ ID NO: 345) | CCTACGGGAGGCATCAG | GCAGATCTCG | CCTACGGGAGGCATCAG | AGTCAGTCAGCC | GGATTAGATACCCTAGTAGTC |
| (SEQ ID NO: 346) | CCTACGGGAGGCATCAG | GCAGATCTCG | CCTACGGGAGGCATCAG | AGTCAGTCAGCC | GGATTAGATACCCTAGTAGTC |
| (SEQ ID NO: 347) | CCTACGGGAGGCATCAG | GCAGATCTCG | CCTACGGGAGGCATCAG | AGTCAGTCAGCC | GGATTAGATACCCTAGTAGTC |
| (SEQ ID NO: 348) | CCTACGGGAGGCATCAG | GCAGATCTCG | CCTACGGGAGGCATCAG | AGTCAGTCAGCC | GGATTAGATACCCTAGTAGTC |
| (SEQ ID NO: 349) | CCTACGGGAGGCATCAG | GCAGATCTCG | CCTACGGGAGGCATCAG | AGTCAGTCAGCC | GGATTAGATACCCTAGTAGTC |
| (SEQ ID NO: 350) | CCTACGGGAGGCATCAG | GCAGATCTCG | CCTACGGGAGGCATCAG | AGTCAGTCAGCC | GGATTAGATACCCTAGTAGTC |
| (SEQ ID NO: 351) | CCTACGGGAGGCATCAG | GCAGATCTCG | CCTACGGGAGGCATCAG | AGTCAGTCAGCC | GGATTAGATACCCTAGTAGTC |
| (SEQ ID NO: 352) | CCTACGGGAGGCATCAG | GCAGATCTCG | CCTACGGGAGGCATCAG | AGTCAGTCAGCC | GGATTAGATACCCTAGTAGTC |
| (SEQ ID NO: 353) | CCTACGGGAGGCATCAG | GCAGATCTCG | CCTACGGGAGGCATCAG | AGTCAGTCAGCC | GGATTAGATACCCTAGTAGTC |
| (SEQ ID NO: 354) | CCTACGGGAGGCATCAG | GCAGATCTCG | CCTACGGGAGGCATCAG | AGTCAGTCAGCC | GGATTAGATACCCTAGTAGTC |
| (SEQ ID NO: 355) | CCTACGGGAGGCATCAG | GCAGATCTCG | CCTACGGGAGGCATCAG | AGTCAGTCAGCC | GGATTAGATACCCTAGTAGTC |
| (SEQ ID NO: 356) | CCTACGGGAGGCATCAG | GCAGATCTCG | CCTACGGGAGGCATCAG | AGTCAGTCAGCC | GGATTAGATACCCTAGTAGTC |
| (SEQ ID NO: 357) | CCTACGGGAGGCATCAG | GCAGATCTCG | CCTACGGGAGGCATCAG | AGTCAGTCAGCC | GGATTAGATACCCTAGTAGTC |
| (SEQ ID NO: 358) | CCTACGGGAGGCATCAG | GCAGATCTCG | CCTACGGGAGGCATCAG | AGTCAGTCAGCC | GGATTAGATACCCTAGTAGTC |
| (SEQ ID NO: 359) | CCTACGGGAGGCATCAG | GCAGATCTCG | CCTACGGGAGGCATCAG | AGTCAGTCAGCC | GGATTAGATACCCTAGTAGTC |
| (SEQ ID NO: 360) | CCTACGGGAGGCATCAG | GCAGATCTCG | CCTACGGGAGGCATCAG | AGTCAGTCAGCC | GGATTAGATACCCTAGTAGTC |
| (SEQ ID NO: 361) | CCTACGGGAGGCATCAG | GCAGATCTCG | CCTACGGGAGGCATCAG | AGTCAGTCAGCC | GGATTAGATACCCTAGTAGTC |
| (SEQ ID NO: 362) | CCTACGGGAGGCATCAG | GCAGATCTCG | CCTACGGGAGGCATCAG | AGTCAGTCAGCC | GGATTAGATACCCTAGTAGTC |
| (SEQ ID NO: 363) | CCTACGGGAGGCATCAG | GCAGATCTCG | CCTACGGGAGGCATCAG | AGTCAGTCAGCC | GGATTAGATACCCTAGTAGTC |
| (SEQ ID NO: 364) | CCTACGGGAGGCATCAG | GCAGATCTCG | CCTACGGGAGGCATCAG | AGTCAGTCAGCC | GGATTAGATACCCTAGTAGTC |
| (SEQ ID NO: 365) | CCTACGGGAGGCATCAG | GCAGATCTCG | CCTACGGGAGGCATCAG | AGTCAGTCAGCC | GGATTAGATACCCTAGTAGTC |
| (SEQ ID NO: 366) | CCTACGGGAGGCATCAG | GCAGATCTCG | CCTACGGGAGGCATCAG | AGTCAGTCAGCC | GGATTAGATACCCTAGTAGTC |
| (SEQ ID NO: 367) | CCTACGGGAGGCATCAG | GCAGATCTCG | CCTACGGGAGGCATCAG | AGTCAGTCAGCC | GGATTAGATACCCTAGTAGTC |
| (SEQ ID NO: 368) | CCTACGGGAGGCATCAG | GCAGATCTCG | CCTACGGGAGGCATCAG | AGTCAGTCAGCC | GGATTAGATACCCTAGTAGTC |
| (SEQ ID NO: 369) | CCTACGGGAGGCATCAG | GCAGATCTCG | CCTACGGGAGGCATCAG | AGTCAGTCAGCC | GGATTAGATACCCTAGTAGTC |
| (SEQ ID NO: 370) | CCTACGGGAGGCATCAG | GCAGATCTCG | CCTACGGGAGGCATCAG | AGTCAGTCAGCC | GGATTAGATACCCTAGTAGTC |
| (SEQ ID NO: 371) | CCTACGGGAGGCATCAG | GCAGATCTCG | CCTACGGGAGGCATCAG | AGTCAGTCAGCC | GGATTAGATACCCTAGTAGTC |
| (SEQ ID NO: 372) | CCTACGGGAGGCATCAG | GCAGATCTCG | CCTACGGGAGGCATCAG | AGTCAGTCAGCC | GGATTAGATACCCTAGTAGTC |
| (SEQ ID NO: 373) | CCTACGGGAGGCATCAG | GCAGATCTCG | CCTACGGGAGGCATCAG | AGTCAGTCAGCC | GGATTAGATACCCTAGTAGTC |
| (SEQ ID NO: 374) | CCTACGGGAGGCATCAG | GCAGATCTCG | CCTACGGGAGGCATCAG | AGTCAGTCAGCC | GGATTAGATACCCTAGTAGTC |
| (SEQ ID NO: 375) | CCTACGGGAGGCATCAG | GCAGATCTCG | CCTACGGGAGGCATCAG | AGTCAGTCAGCC | GGATTAGATACCCTAGTAGTC |

TABLE 2-continued

| | forward primer binding site fragment | 5' universal sequence fragment | barcode sequence fragment | 3' universal sequence fragment | reverse primer binding site fragment |
|---|---|---|---|---|---|
| (SEQ ID NO: 376) | CCTACGGGAGGCATCAG | GCAGATCTCG | CCTACGGGAGGCATCAG | AGTCAGTCAGCC | GGATTAGATACCCTAGTAGTC |
| (SEQ ID NO: 377) | CCTACGGGAGGCATCAG | GCAGATCTCG | CCTACGGGAGGCATCAG | AGTCAGTCAGCC | GGATTAGATACCCTAGTAGTC |
| (SEQ ID NO: 378) | CCTACGGGAGGCATCAG | GCAGATCTCG | CCTACGGGAGGCATCAG | AGTCAGTCAGCC | GGATTAGATACCCTAGTAGTC |
| (SEQ ID NO: 379) | CCTACGGGAGGCATCAG | GCAGATCTCG | CCTACGGGAGGCATCAG | AGTCAGTCAGCC | GGATTAGATACCCTAGTAGTC |
| (SEQ ID NO: 380) | CCTACGGGAGGCATCAG | GCAGATCTCG | CCTACGGGAGGCATCAG | AGTCAGTCAGCC | GGATTAGATACCCTAGTAGTC |
| (SEQ ID NO: 381) | CCTACGGGAGGCATCAG | GCAGATCTCG | CCTACGGGAGGCATCAG | AGTCAGTCAGCC | GGATTAGATACCCTAGTAGTC |
| (SEQ ID NO: 382) | CCTACGGGAGGCATCAG | GCAGATCTCG | CCTACGGGAGGCATCAG | AGTCAGTCAGCC | GGATTAGATACCCTAGTAGTC |
| (SEQ ID NO: 383) | CCTACGGGAGGCATCAG | GCAGATCTCG | CCTACGGGAGGCATCAG | AGTCAGTCAGCC | GGATTAGATACCCTAGTAGTC |
| (SEQ ID NO: 384) | CCTACGGGAGGCATCAG | GCAGATCTCG | CCTACGGGAGGCATCAG | AGTCAGTCAGCC | GGATTAGATACCCTAGTAGTC |

In one illustrative aspect, the control composition for qPCR comprises a nucleic acid construct comprising at least one barcode sequence fragment linked at its 5' or 3' end to primer binding site fragments. In another embodiment, the nucleic acid construct comprises at least one universal sequence fragment. In another embodiment, the nucleic acid construct comprises at least a first and a second universal sequence fragment, and the first universal sequence fragment can be linked to the 5' end of the barcode sequence fragment and the second universal sequence fragment can be linked to the 3' end of the barcode sequence fragment. In one aspect, the universal sequence fragments can be extended as needed to make the nucleic acid construct longer for different applications.

In various embodiments, the universal sequence fragments can be from about 10 base pairs in length to about 270 base pairs in length, from about 10 base pairs in length to about 260 base pairs in length, from about 10 base pairs in length to about 250 base pairs in length, from about 10 base pairs in length to about 240 base pairs in length, from about 10 base pairs in length to about 230 base pairs in length, from about 10 base pairs in length to about 220 base pairs in length, from about 10 base pairs in length to about 210 base pairs in length, from about 10 base pairs in length to about 200 base pairs in length, from about 10 base pairs in length to about 190 base pairs in length, from about 10 base pairs in length to about 180 base pairs in length, from about 10 base pairs in length to about 170 base pairs in length, from about 10 base pairs in length to about 160 base pairs in length, from about 10 base pairs in length to about 150 base pairs in length, from about 10 base pairs in length to about 140 base pairs in length, from about 10 base pairs in length to about 130 base pairs in length, from about 10 base pairs in length to about 120 base pairs in length, from about 10 base pairs in length to about 110 base pairs in length, from about 10 base pairs in length to about 100 base pairs in length, from about 10 base pairs in length to about 90 base pairs in length, from about 10 base pairs in length to about 80 base pairs in length, from about 10 base pairs in length to about 70 base pairs in length, from about 10 base pairs in length to about 60 base pairs in length, from about 10 base pairs in length to about 50 base pairs in length, from about 10 base pairs in length to about 40 base pairs in length, from about 10 base pairs in length to about 30 base pairs in length, from about 10 base pairs in length to about 20 base pairs in length, from about 10 base pairs in length to about 15 base pairs in length, from about 8 base pairs in length to about 15 base pairs in length, or from about 8 base pairs in length to about 12 base pairs in length.

First and second primer binding site fragments are included in the nucleic acid construct. In this aspect, the primers can be any primers of interest. In one embodiment, the first primer binding site fragment is linked at its 3'end to the 5' end of a first universal sequence fragment and the second primer binding site fragment is linked at its 5' end to the 3' end of a second universal sequence fragment (see FIG. 1 for an example). In various embodiments, the primer binding site fragments can range in length from about 15 base pairs to about 28 base pairs, from about 15 base pairs to about 26 base pairs, from about 15 base pairs to about 24 base pairs, from about 15 base pairs to about 22 base pairs, from about 15 base pairs to about 20 base pairs, from about 16 base pairs to about 22 base pairs, from about 16 base pairs to about 20 base pairs, from about 17 base pairs to about 20 base pairs, or can be about 18 base pairs.

In all of the various embodiments described above, the entire nucleic acid construct, not including plasmid sequence if a plasmid is present, can range in length from about 80 base pairs to about 300 base pairs, from about 80 base pairs to about 290 base pairs, from about 80 base pairs to about 280 base pairs, from about 80 base pairs to about 270 base pairs, from about 80 base pairs to about 260 base pairs, from about 80 base pairs to about 250 base pairs, from about 80 base pairs to about 240 base pairs, from about 80 base pairs to about 230 base pairs, from about 80 base pairs to about 220 base pairs, from about 80 base pairs to about 210 base pairs, from about 80 base pairs to about 200 base pairs, from about 80 base pairs to about 190 base pairs, from about 80 base pairs to about 180 base pairs, from about 80 base pairs to about 170 base pairs, or from about 80 base pairs to about 160 base pairs.

Various embodiments of the nucleic acid constructs, including the forward and reverse primer binding site fragments, 5' and 3' universal sequence fragments, and the barcode sequence fragment are shown in Table 2 above having SEQ ID NOS:1 to 384. The corresponding full sequences are also shown as SEQ ID NOS:385 to 768 in Table 3 below. These embodiments have primer binding site fragments in accordance with the nucleic acid construct exemplified in FIG. 1.

TABLE 3

| | full sequence |
|---|---|
| (SEQ ID NO: 385) | CCTACGGGAGGCATCAGGCAGATCTCGTCCCTTGTCTCCACGAGACTGATTAGTCAGTCAGCCGGATTAGATACCCTAGTAGTC |
| (SEQ ID NO: 386) | CCTACGGGAGGCATCAGGCAGATCTCGGCTGTACGGATTATCACCAGGTGTAGTCAGTCAGCCGGATTAGATACCCTAGTAGTC |
| (SEQ ID NO: 387) | CCTACGGGAGGCATCAGGCAGATCTCGTGGTCAACGATACATCGCGTTGACAGTCAGTCAGCCGGATTAGATACCCTAGTAGTC |
| (SEQ ID NO: 388) | CCTACGGGAGGCATCAGGCAGATCTCGATCGCACAGTAAGCACATAGTCGTAGTCAGTCAGCCGGATTAGATACCCTAGTAGTC |
| (SEQ ID NO: 389) | CCTACGGGAGGCATCAGGCAGATCTCGGTCGTGTAGCCTGGCAAATACACTAGTCAGTCAGCCGGATTAGATACCCTAGTAGTC |
| (SEQ ID NO: 390) | CCTACGGGAGGCATCAGGCAGATCTCGAGCGGAGGTTAGGTCATGCTCCAGAGTCAGTCAGCCGGATTAGATACCCTAGTAGTC |
| (SEQ ID NO: 391) | CCTACGGGAGGCATCAGGCAGATCTCGATCCTTTGGTTCCCTAGTAAGCTGAGTCAGTCAGCCGGATTAGATACCCTAGTAGTC |
| (SEQ ID NO: 392) | CCTACGGGAGGCATCAGGCAGATCTCGTACAGCGCATACTTACCGACGAGTAGTCAGTCAGCCGGATTAGATACCCTAGTAGTC |
| (SEQ ID NO: 393) | CCTACGGGAGGCATCAGGCAGATCTCGACCGGTATGTACGCTTAGATGTAGAGTCAGTCAGCCGGATTAGATACCCTAGTAGTC |
| (SEQ ID NO: 394) | CCTACGGGAGGCATCAGGCAGATCTCGAATTGTGTCGGAAAGACGTAGCGGAGTCAGTCAGCCGGATTAGATACCCTAGTAGTC |
| (SEQ ID NO: 395) | CCTACGGGAGGCATCAGGCAGATCTCGTGCATACACTGGTTACCTTACACCAGTCAGTCAGCCGGATTAGATACCCTAGTAGTC |
| (SEQ ID NO: 396) | CCTACGGGAGGCATCAGGCAGATCTCGAGTCGAACGAGGTGACTAATGGCCAGTCAGTCAGCCGGATTAGATACCCTAGTAGTC |
| (SEQ ID NO: 397) | CCTACGGGAGGCATCAGGCAGATCTCGACCAGTGACTCACTCTCTCACTTGAGTCAGTCAGCCGGATTAGATACCCTAGTAGTC |
| (SEQ ID NO: 398) | CCTACGGGAGGCATCAGGCAGATCTCGGAATACCAAGTCATTGCAAGCAACAGTCAGTCAGCCGGATTAGATACCCTAGTAGTC |
| (SEQ ID NO: 399) | CCTACGGGAGGCATCAGGCAGATCTCGGTAGATCGTGTACACGTGACATGTAGTCAGTCAGCCGGATTAGATACCCTAGTAGTC |
| (SEQ ID NO: 400) | CCTACGGGAGGCATCAGGCAGATCTCGTAACGTGTGTGCCACAGTTGAAGTAGTCAGTCAGCCGGATTAGATACCCTAGTAGTC |
| (SEQ ID NO: 401) | CCTACGGGAGGCATCAGGCAGATCTCGCATTATGGCGTGCTAGGATCACTGAGTCAGTCAGCCGGATTAGATACCCTAGTAGTC |
| (SEQ ID NO: 402) | CCTACGGGAGGCATCAGGCAGATCTCGCCAATACGCCTGGATGACCCAAATAGTCAGTCAGCCGGATTAGATACCCTAGTAGTC |
| (SEQ ID NO: 403) | CCTACGGGAGGCATCAGGCAGATCTCGGATCTGCGATCCACCGGAGTAGGAAGTCAGTCAGCCGGATTAGATACCCTAGTAGTC |
| (SEQ ID NO: 404) | CCTACGGGAGGCATCAGGCAGATCTCGCAGCTCATCAGCTGAGGACTACCTAGTCAGTCAGCCGGATTAGATACCCTAGTAGTC |
| (SEQ ID NO: 405) | CCTACGGGAGGCATCAGGCAGATCTCGCAAACAACAGCTCAATCGGCTTGCAGTCAGTCAGCCGGATTAGATACCCTAGTAGTC |
| (SEQ ID NO: 406) | CCTACGGGAGGCATCAGGCAGATCTCGGCAACACCATCCAACACTCGATCGAGTCAGTCAGCCGGATTAGATACCCTAGTAGTC |
| (SEQ ID NO: 407) | CCTACGGGAGGCATCAGGCAGATCTCGGCGATATATCGCTGACCGGCTGTTAGTCAGTCAGCCGGATTAGATACCCTAGTAGTC |
| (SEQ ID NO: 408) | CCTACGGGAGGCATCAGGCAGATCTCGCGAGCAATCCTAGGAGGAGCAATAAGTCAGTCAGCCGGATTAGATACCCTAGTAGTC |
| (SEQ ID NO: 409) | CCTACGGGAGGCATCAGGCAGATCTCGAGTCGTGCACATAGCGACGAAGACAGTCAGTCAGCCGGATTAGATACCCTAGTAGTC |
| (SEQ ID NO: 410) | CCTACGGGAGGCATCAGGCAGATCTCGGTATCTGCGCGTCTTCCCTAACTCAGTCAGTCAGCCGGATTAGATACCCTAGTAGTC |
| (SEQ ID NO: 411) | CCTACGGGAGGCATCAGGCAGATCTCGCGAGGGAAAGTCTGGAAGAACGGCAGTCAGTCAGCCGGATTAGATACCCTAGTAGTC |
| (SEQ ID NO: 412) | CCTACGGGAGGCATCAGGCAGATCTCGCAAATTCGGGATGCTAGACACTACAGTCAGTCAGCCGGATTAGATACCCTAGTAGTC |
| (SEQ ID NO: 413) | CCTACGGGAGGCATCAGGCAGATCTCGAGATTGACCAACTTGGATTGAACGAGTCAGTCAGCCGGATTAGATACCCTAGTAGTC |
| (SEQ ID NO: 414) | CCTACGGGAGGCATCAGGCAGATCTCGAGTTACGAGCTAGATATACCAGTGAGTCAGTCAGCCGGATTAGATACCCTAGTAGTC |
| (SEQ ID NO: 415) | CCTACGGGAGGCATCAGGCAGATCTCGGCATATGCACTGAACAAACTGCCAAGTCAGTCAGCCGGATTAGATACCCTAGTAGTC |
| (SEQ ID NO: 406) | CCTACGGGAGGCATCAGGCAGATCTCGCAACTCCCGTGAGTAGACATGTGTAGTCAGTCAGCCGGATTAGATACCCTAGTAGTC |
| (SEQ ID NO: 407) | CCTACGGGAGGCATCAGGCAGATCTCGTTGCGTTAGCAGTACAGTTACGCGAGTCAGTCAGCCGGATTAGATACCCTAGTAGTC |
| (SEQ ID NO: 408) | CCTACGGGAGGCATCAGGCAGATCTCGTACGAGCCCTAACAAGCCCTAGTAAGTCAGTCAGCCGGATTAGATACCCTAGTAGTC |
| (SEQ ID NO: 409) | CCTACGGGAGGCATCAGGCAGATCTCGCACTACGCTAGATAGTGTCGGATCAGTCAGTCAGCCGGATTAGATACCCTAGTAGTC |
| (SEQ ID NO: 410) | CCTACGGGAGGCATCAGGCAGATCTCGTGCAGTCCTCGACTGAGCTCTGCAAGTCAGTCAGCCGGATTAGATACCCTAGTAGTC |
| (SEQ ID NO: 421) | CCTACGGGAGGCATCAGGCAGATCTCGACCATAGCTCCGCTTCGACTTTCCAGTCAGTCAGCCGGATTAGATACCCTAGTAGTC |
| (SEQ ID NO: 422) | CCTACGGGAGGCATCAGGCAGATCTCGTCGACATCTCTTGTCATAAGAACCAGTCAGTCAGCCGGATTAGATACCCTAGTAGTC |
| (SEQ ID NO: 423) | CCTACGGGAGGCATCAGGCAGATCTCGGAACACTTTGGAGTCCGCAAGTTAAGTCAGTCAGCCGGATTAGATACCCTAGTAGTC |

TABLE 3-continued

| | full sequence |
|---|---|
| (SEQ ID NO: 424) | CCTACGGGAGGCATCAGGCAGATCTCGGAGCCATCTGTACGTAGAGCTCTCAGTCAGTCAGCCGGATTAGATACCCTAGTAGTC |
| (SEQ ID NO: 425) | CCTACGGGAGGCATCAGGCAGATCTCGTTGGGTACACGTCCTCTGAGAGCTAGTCAGTCAGCCGGATTAGATACCCTAGTAGTC |
| (SEQ ID NO: 426) | CCTACGGGAGGCATCAGGCAGATCTCGAAGGCGCTCCTTCCTCGATGCAGTAGTCAGTCAGCCGGATTAGATACCCTAGTAGTC |
| (SEQ ID NO: 427) | CCTACGGGAGGCATCAGGCAGATCTCGTAATACGGATCGGCGGACTATTCAAGTCAGTCAGCCGGATTAGATACCCTAGTAGTC |
| (SEQ ID NO: 428) | CCTACGGGAGGCATCAGGCAGATCTCGTCGGAATTAGACCGTGCACAATTGAGTCAGTCAGCCGGATTAGATACCCTAGTAGTC |
| (SEQ ID NO: 429) | CCTACGGGAGGCATCAGGCAGATCTCGTGTGAATTCGGACGGCCTAAGTTCAGTCAGTCAGCCGGATTAGATACCCTAGTAGTC |
| (SEQ ID NO: 430) | CCTACGGGAGGCATCAGGCAGATCTCGCATTCGTGGCGTAGCGCTCACATCAGTCAGTCAGCCGGATTAGATACCCTAGTAGTC |
| (SEQ ID NO: 431) | CCTACGGGAGGCATCAGGCAGATCTCGTACTACGTGGCCTGGTTATGGCACAGTCAGTCAGCCGGATTAGATACCCTAGTAGTC |
| (SEQ ID NO: 432) | CCTACGGGAGGCATCAGGCAGATCTCGGGCCAGTTCCTACGAGGTTCTGATAGTCAGTCAGCCGGATTAGATACCCTAGTAGTC |
| (SEQ ID NO: 433) | CCTACGGGAGGCATCAGGCAGATCTCGGATGTTCGCTAGAACTCCTGTGGAAGTCAGTCAGCCGGATTAGATACCCTAGTAGTC |
| (SEQ ID NO: 434) | CCTACGGGAGGCATCAGGCAGATCTCGCTATCTCCTGTCTAATGGTCGTAGAGTCAGTCAGCCGGATTAGATACCCTAGTAGTC |
| (SEQ ID NO: 435) | CCTACGGGAGGCATCAGGCAGATCTCGACTCACAGGAATTTGCACCGTCGAAGTCAGTCAGCCGGATTAGATACCCTAGTAGTC |
| (SEQ ID NO: 436) | CCTACGGGAGGCATCAGGCAGATCTCGATGATGAGCCTCTGCTACAGACGTAGTCAGTCAGCCGGATTAGATACCCTAGTAGTC |
| (SEQ ID NO: 437) | CCTACGGGAGGCATCAGGCAGATCTCGGTCGACAGAGGAATGGCCTGACTAAGTCAGTCAGCCGGATTAGATACCCTAGTAGTC |
| (SEQ ID NO: 438) | CCTACGGGAGGCATCAGGCAGATCTCGTGTCGCAAATAGACGCACATACAAAGTCAGTCAGCCGGATTAGATACCCTAGTAGTC |
| (SEQ ID NO: 439) | CCTACGGGAGGCATCAGGCAGATCTCGCATCCCTCTACTTGAGTGGTCTGTAGTCAGTCAGCCGGATTAGATACCCTAGTAGTC |
| (SEQ ID NO: 440) | CCTACGGGAGGCATCAGGCAGATCTCGTATACCGCTGCGGATAGCACTCGTAGTCAGTCAGCCGGATTAGATACCCTAGTAGTC |
| (SEQ ID NO: 441) | CCTACGGGAGGCATCAGGCAGATCTCGAGTTGAGGCATTTAGCGCGAACTTAGTCAGTCAGCCGGATTAGATACCCTAGTAGTC |
| (SEQ ID NO: 442) | CCTACGGGAGGCATCAGGCAGATCTCGACAATAGACACCCATACACGCACCAGTCAGTCAGCCGGATTAGATACCCTAGTAGTC |
| (SEQ ID NO: 443) | CCTACGGGAGGCATCAGGCAGATCTCGCGGTCAATTGACACCTCAGTCAAGAGTCAGTCAGCCGGATTAGATACCCTAGTAGTC |
| (SEQ ID NO: 444) | CCTACGGGAGGCATCAGGCAGATCTCGGTGGAGTCTCATTCGACCAAACACAGTCAGTCAGCCGGATTAGATACCCTAGTAGTC |
| (SEQ ID NO: 445) | CCTACGGGAGGCATCAGGCAGATCTCGGCTCGAAGATTCCCACCCAGTAACAGTCAGTCAGCCGGATTAGATACCCTAGTAGTC |
| (SEQ ID NO: 446) | CCTACGGGAGGCATCAGGCAGATCTCGAGGCTTACGTGTATATCGCGATGAAGTCAGTCAGCCGGATTAGATACCCTAGTAGTC |
| (SEQ ID NO: 447) | CCTACGGGAGGCATCAGGCAGATCTCGTCTCTACCACTCCGCCGGTAATCTAGTCAGTCAGCCGGATTAGATACCCTAGTAGTC |
| (SEQ ID NO: 448) | CCTACGGGAGGCATCAGGCAGATCTCGACTTCCAACTTCCCGATGCCTTGAAGTCAGTCAGCCGGATTAGATACCCTAGTAGTC |
| (SEQ ID NO: 449) | CCTACGGGAGGCATCAGGCAGATCTCGCTCACCTAGGAAAGCAGGCACGAAAGTCAGTCAGCCGGATTAGATACCCTAGTAGTC |
| (SEQ ID NO: 450) | CCTACGGGAGGCATCAGGCAGATCTCGGTGTTGTCGTGCTACGCAGCACTAAGTCAGTCAGCCGGATTAGATACCCTAGTAGTC |
| (SEQ ID NO: 451) | CCTACGGGAGGCATCAGGCAGATCTCGCCACAGATCGATCGCTTAGTGCTGAGTCAGTCAGCCGGATTAGATACCCTAGTAGTC |
| (SEQ ID NO: 452) | CCTACGGGAGGCATCAGGCAGATCTCGTATCGACACAAGCAAAGTTTGCGAAGTCAGTCAGCCGGATTAGATACCCTAGTAGTC |
| (SEQ ID NO: 453) | CCTACGGGAGGCATCAGGCAGATCTCGGATTCCGGCTCATCGAGCCGATCTAGTCAGTCAGCCGGATTAGATACCCTAGTAGTC |
| (SEQ ID NO: 454) | CCTACGGGAGGCATCAGGCAGATCTCGCGTAATTGCCGCCTCATCATGTTCAGTCAGTCAGCCGGATTAGATACCCTAGTAGTC |
| (SEQ ID NO: 455) | CCTACGGGAGGCATCAGGCAGATCTCGGGTGACTAGTTCCCAGGGACTTCTAGTCAGTCAGCCGGATTAGATACCCTAGTAGTC |
| (SEQ ID NO: 456) | CCTACGGGAGGCATCAGGCAGATCTCGATGGGTTCCGTCGCAATCCTTGCGAGTCAGTCAGCCGGATTAGATACCCTAGTAGTC |
| (SEQ ID NO: 457) | CCTACGGGAGGCATCAGGCAGATCTCGTAGGCATGCTTGCCTGCTTCCTTCAGTCAGTCAGCCGGATTAGATACCCTAGTAGTC |
| (SEQ ID NO: 458) | CCTACGGGAGGCATCAGGCAGATCTCGAACTAGTTCAGGCAAGGCACAAGGAGTCAGTCAGCCGGATTAGATACCCTAGTAGTC |
| (SEQ ID NO: 459) | CCTACGGGAGGCATCAGGCAGATCTCGATTCTGCCGAAGGGCCTATAAGTCAGTCAGTCAGCCGGATTAGATACCCTAGTAGTC |
| (SEQ ID NO: 460) | CCTACGGGAGGCATCAGGCAGATCTCGAGCATGTCCCGTTCCATTTCATGCAGTCAGTCAGCCGGATTAGATACCCTAGTAGTC |
| (SEQ ID NO: 461) | CCTACGGGAGGCATCAGGCAGATCTCGGTACGATATGACTCGGCGATCATCAGTCAGTCAGCCGGATTAGATACCCTAGTAGTC |
| (SEQ ID NO: 462) | CCTACGGGAGGCATCAGGCAGATCTCGGTGGTGGTTTCCGTTTCACGCGAAAGTCAGTCAGCCGGATTAGATACCCTAGTAGTC |

TABLE 3-continued

| | full sequence |
|---|---|
| (SEQ ID NO: 463) | CCTACGGGAGGCATCAGGCAGATCTCGTAGTATGCGCAAACAAGAACCTTGAGTCAGTCAGCCGGATTAGATACCCTAGTAGTC |
| (SEQ ID NO: 464) | CCTACGGGAGGCATCAGGCAGATCTCGTGCGCTGAATGTTACTCTCTTAGCAGTCAGTCAGCCGGATTAGATACCCTAGTAGTC |
| (SEQ ID NO: 465) | CCTACGGGAGGCATCAGGCAGATCTCGATGGCTGTCAGTAACTGTTCGCGCAGTCAGTCAGCCGGATTAGATACCCTAGTAGTC |
| (SEQ ID NO: 466) | CCTACGGGAGGCATCAGGCAGATCTCGGTTCTCTTCTCGCGAAGCATCTACAGTCAGTCAGCCGGATTAGATACCCTAGTAGTC |
| (SEQ ID NO: 467) | CCTACGGGAGGCATCAGGCAGATCTCGCGTAAGATGCCTGTTTGGCCACACAGTCAGTCAGCCGGATTAGATACCCTAGTAGTC |
| (SEQ ID NO: 468) | CCTACGGGAGGCATCAGGCAGATCTCGGCGTTCTAGCTGTCAGGTTGCCCAAGTCAGTCAGCCGGATTAGATACCCTAGTAGTC |
| (SEQ ID NO: 469) | CCTACGGGAGGCATCAGGCAGATCTCGGTTGTTCTGGGATCATTCCACTCAAGTCAGTCAGCCGGATTAGATACCCTAGTAGTC |
| (SEQ ID NO: 470) | CCTACGGGAGGCATCAGGCAGATCTCGGGACTTCCAGCTGTCACATCACGAAGTCAGTCAGCCGGATTAGATACCCTAGTAGTC |
| (SEQ ID NO: 471) | CCTACGGGAGGCATCAGGCAGATCTCGCTCACAACCGTGCGACATTTCTCTAGTCAGTCAGCCGGATTAGATACCCTAGTAGTC |
| (SEQ ID NO: 472) | CCTACGGGAGGCATCAGGCAGATCTCGCTGCTATTCCTCGGACGTTAACTAAGTCAGTCAGCCGGATTAGATACCCTAGTAGTC |
| (SEQ ID NO: 473) | CCTACGGGAGGCATCAGGCAGATCTCGATGTCACCGCTGTAGCAGTTGCGTAGTCAGTCAGCCGGATTAGATACCCTAGTAGTC |
| (SEQ ID NO: 474) | CCTACGGGAGGCATCAGGCAGATCTCGTGTAACGCCGATCACGCTATTGGAAGTCAGTCAGCCGGATTAGATACCCTAGTAGTC |
| (SEQ ID NO: 475) | CCTACGGGAGGCATCAGGCAGATCTCGAGCAGAACATCTAACTTCACTTCCAGTCAGTCAGCCGGATTAGATACCCTAGTAGTC |
| (SEQ ID NO: 476) | CCTACGGGAGGCATCAGGCAGATCTCGTGGAGTAGGTGGCCAGTGGATATAAGTCAGTCAGCCGGATTAGATACCCTAGTAGTC |
| (SEQ ID NO: 477) | CCTACGGGAGGCATCAGGCAGATCTCGTTGGCTCTATTCTGTGTGTAACGCAGTCAGTCAGCCGGATTAGATACCCTAGTAGTC |
| (SEQ ID NO: 478) | CCTACGGGAGGCATCAGGCAGATCTCGGATCCCACGTACCCAATCGTGCAAAGTCAGTCAGCCGGATTAGATACCCTAGTAGTC |
| (SEQ ID NO: 479) | CCTACGGGAGGCATCAGGCAGATCTCGTACCGCTTCTTCAGGCTAGCAGAGAGTCAGTCAGCCGGATTAGATACCCTAGTAGTC |
| (SEQ ID NO: 480) | CCTACGGGAGGCATCAGGCAGATCTCGTGTGCGATAACAGTCACTCCGAACAGTCAGTCAGCCGGATTAGATACCCTAGTAGTC |
| (SEQ ID NO: 481) | CCTACGGGAGGCATCAGGCAGATCTCGGATTATCGACGACACCGAAATCTGAGTCAGTCAGCCGGATTAGATACCCTAGTAGTC |
| (SEQ ID NO: 482) | CCTACGGGAGGCATCAGGCAGATCTCGGCCTAGCCCAATTGACGTAGAACTAGTCAGTCAGCCGGATTAGATACCCTAGTAGTC |
| (SEQ ID NO: 483) | CCTACGGGAGGCATCAGGCAGATCTCGGATGTATGTGGTCTATGCCGGCTAAGTCAGTCAGCCGGATTAGATACCCTAGTAGTC |
| (SEQ ID NO: 484) | CCTACGGGAGGCATCAGGCAGATCTCGACTCCTTGTGTTGTGGTATGGGAGAGTCAGTCAGCCGGATTAGATACCCTAGTAGTC |
| (SEQ ID NO: 485) | CCTACGGGAGGCATCAGGCAGATCTCGGTCACGGACATTTGTACCAACCGAAGTCAGTCAGCCGGATTAGATACCCTAGTAGTC |
| (SEQ ID NO: 486) | CCTACGGGAGGCATCAGGCAGATCTCGGCGAGCGAAGTAAGGGTACAGGGTAGTCAGTCAGCCGGATTAGATACCCTAGTAGTC |
| (SEQ ID NO: 487) | CCTACGGGAGGCATCAGGCAGATCTCGATCTACCGAAGCAGAGTGCTAATCAGTCAGTCAGCCGGATTAGATACCCTAGTAGTC |
| (SEQ ID NO: 488) | CCTACGGGAGGCATCAGGCAGATCTCGACTTGGTGTAAGTTGGCGGGTTATAGTCAGTCAGCCGGATTAGATACCCTAGTAGTC |
| (SEQ ID NO: 489) | CCTACGGGAGGCATCAGGCAGATCTCGTCTTGGAGGTCACACGATGGTCATAGTCAGTCAGCCGGATTAGATACCCTAGTAGTC |
| (SEQ ID NO: 490) | CCTACGGGAGGCATCAGGCAGATCTCGTCACCTCCTTGTGTCACCAATCCGAGTCAGTCAGCCGGATTAGATACCCTAGTAGTC |
| (SEQ ID NO: 491) | CCTACGGGAGGCATCAGGCAGATCTCGGCACACCTGATACACTAACAAACGAGTCAGTCAGCCGGATTAGATACCCTAGTAGTC |
| (SEQ ID NO: 492) | CCTACGGGAGGCATCAGGCAGATCTCGGCGACAATTACATTCCAGGCAGATAGTCAGTCAGCCGGATTAGATACCCTAGTAGTC |
| (SEQ ID NO: 493) | CCTACGGGAGGCATCAGGCAGATCTCGTCATGCTCCATTTATGGTACCCAGAGTCAGTCAGCCGGATTAGATACCCTAGTAGTC |
| (SEQ ID NO: 494) | CCTACGGGAGGCATCAGGCAGATCTCGAGCTGTCAAGCTCACGACTTGACAAGTCAGTCAGCCGGATTAGATACCCTAGTAGTC |
| (SEQ ID NO: 495) | CCTACGGGAGGCATCAGGCAGATCTCGGAGAGCAACAGACTTGGAGGCTTAAGTCAGTCAGCCGGATTAGATACCCTAGTAGTC |
| (SEQ ID NO: 496) | CCTACGGGAGGCATCAGGCAGATCTCGTACTCGGGAACTACGTGGTTCCACAGTCAGTCAGCCGGATTAGATACCCTAGTAGTC |
| (SEQ ID NO: 497) | CCTACGGGAGGCATCAGGCAGATCTCGCGTGCTTAGGCTGACGCTTTGCTGAGTCAGTCAGCCGGATTAGATACCCTAGTAGTC |
| (SEQ ID NO: 498) | CCTACGGGAGGCATCAGGCAGATCTCGTACCGAAGGTATACAGGGTTTGTAAGTCAGTCAGCCGGATTAGATACCCTAGTAGTC |
| (SEQ ID NO: 499) | CCTACGGGAGGCATCAGGCAGATCTCGCACTCATCATTCGCCTATGAGATCAGTCAGTCAGCCGGATTAGATACCCTAGTAGTC |
| (SEQ ID NO: 500) | CCTACGGGAGGCATCAGGCAGATCTCGGTATTTCGGACGCAAACCTATGGCAGTCAGTCAGCCGGATTAGATACCCTAGTAGTC |
| (SEQ ID NO: 501) | CCTACGGGAGGCATCAGGCAGATCTCGTATCTATCCTGCATCGCTTAAGGCAGTCAGTCAGCCGGATTAGATACCCTAGTAGTC |

TABLE 3-continued

| | full sequence |
|---|---|
| (SEQ ID NO: 502) | CCTACGGGAGGCATCAGGCAGATCTCGTTGCCAAGAGTCACCATCCAACGAAGTCAGTCAGCCGGATTAGATACCCTAGTAGTC |
| (SEQ ID NO: 503) | CCTACGGGAGGCATCAGGCAGATCTCGAGTAGCGGAAGAGCAATAGGAGGAAGTCAGTCAGCCGGATTAGATACCCTAGTAGTC |
| (SEQ ID NO: 504) | CCTACGGGAGGCATCAGGCAGATCTCGGCAATTAGGTACCCGAACGTCACTAGTCAGTCAGCCGGATTAGATACCCTAGTAGTC |
| (SEQ ID NO: 505) | CCTACGGGAGGCATCAGGCAGATCTCGCATACCGTGAGTACACCAACACCAAGTCAGTCAGCCGGATTAGATACCCTAGTAGTC |
| (SEQ ID NO: 506) | CCTACGGGAGGCATCAGGCAGATCTCGATGTGTGTAGACCCATCACATAGGAGTCAGTCAGCCGGATTAGATACCCTAGTAGTC |
| (SEQ ID NO: 507) | CCTACGGGAGGCATCAGGCAGATCTCGCCTGCGAAGTATCGACACGGAGAAAGTCAGTCAGCCGGATTAGATACCCTAGTAGTC |
| (SEQ ID NO: 508) | CCTACGGGAGGCATCAGGCAGATCTCGTTCTCTCGACATGAACCTATGACAAGTCAGTCAGCCGGATTAGATACCCTAGTAGTC |
| (SEQ ID NO: 509) | CCTACGGGAGGCATCAGGCAGATCTCGGCTCTCCGTAGAATGCCGGTAATAAGTCAGTCAGCCGGATTAGATACCCTAGTAGTC |
| (SEQ ID NO: 510) | CCTACGGGAGGCATCAGGCAGATCTCGGTTAAGCTGACCGAACAGCTCTACAGTCAGTCAGCCGGATTAGATACCCTAGTAGTC |
| (SEQ ID NO: 511) | CCTACGGGAGGCATCAGGCAGATCTCGATGCCATGCCGTGTGAGTCATACCAGTCAGTCAGCCGGATTAGATACCCTAGTAGTC |
| (SEQ ID NO: 512) | CCTACGGGAGGCATCAGGCAGATCTCGGACATTGTCACGTGGCCGTTACTGAGTCAGTCAGCCGGATTAGATACCCTAGTAGTC |
| (SEQ ID NO: 513) | CCTACGGGAGGCATCAGGCAGATCTCGGCCAACAACCATTAGAGCTGCCATAGTCAGTCAGCCGGATTAGATACCCTAGTAGTC |
| (SEQ ID NO: 514) | CCTACGGGAGGCATCAGGCAGATCTCGATCAGTACTAGGATCTAGTGGCAAAGTCAGTCAGCCGGATTAGATACCCTAGTAGTC |
| (SEQ ID NO: 515) | CCTACGGGAGGCATCAGGCAGATCTCGTCCTCGAGCGATCCTTCAATGGGAAGTCAGTCAGCCGGATTAGATACCCTAGTAGTC |
| (SEQ ID NO: 516) | CCTACGGGAGGCATCAGGCAGATCTCGACCCAAGCGTTATTGACGACATCGAGTCAGTCAGCCGGATTAGATACCCTAGTAGTC |
| (SEQ ID NO: 517) | CCTACGGGAGGCATCAGGCAGATCTCGTGCAGCAAGATTACATACTGAGCAAGTCAGTCAGCCGGATTAGATACCCTAGTAGTC |
| (SEQ ID NO: 518) | CCTACGGGAGGCATCAGGCAGATCTCGAGCAACATTGCAGGCTAAACTATGAGTCAGTCAGCCGGATTAGATACCCTAGTAGTC |
| (SEQ ID NO: 519) | CCTACGGGAGGCATCAGGCAGATCTCGGATGTGGTGTTAAAGAGCAGAGCCAGTCAGTCAGCCGGATTAGATACCCTAGTAGTC |
| (SEQ ID NO: 520) | CCTACGGGAGGCATCAGGCAGATCTCGCAGAAATGTGTCGGAGAGATCACGAGTCAGTCAGCCGGATTAGATACCCTAGTAGTC |
| (SEQ ID NO: 521) | CCTACGGGAGGCATCAGGCAGATCTCGGTAGAGGTAGAGTCAACCCGTGAAAGTCAGTCAGCCGGATTAGATACCCTAGTAGTC |
| (SEQ ID NO: 522) | CCTACGGGAGGCATCAGGCAGATCTCGCGTGATCCGCTAGTTTGAAACACGAGTCAGTCAGCCGGATTAGATACCCTAGTAGTC |
| (SEQ ID NO: 523) | CCTACGGGAGGCATCAGGCAGATCTCGGGTTATTTGGCGAGAGAGACAGGTAGTCAGTCAGCCGGATTAGATACCCTAGTAGTC |
| (SEQ ID NO: 524) | CCTACGGGAGGCATCAGGCAGATCTCGGGATCGTAATACTCGCCAGTGCATAGTCAGTCAGCCGGATTAGATACCCTAGTAGTC |
| (SEQ ID NO: 525) | CCTACGGGAGGCATCAGGCAGATCTCGGCATAGCATCAAGCTCAGGACTCTAGTCAGTCAGCCGGATTAGATACCCTAGTAGTC |
| (SEQ ID NO: 526) | CCTACGGGAGGCATCAGGCAGATCTCGGTGTTAGATGTGCACTTTGGGTGCAGTCAGTCAGCCGGATTAGATACCCTAGTAGTC |
| (SEQ ID NO: 527) | CCTACGGGAGGCATCAGGCAGATCTCGTTAGAGCCATGCTCTAGCCTGGCAAGTCAGTCAGCCGGATTAGATACCCTAGTAGTC |
| (SEQ ID NO: 528) | CCTACGGGAGGCATCAGGCAGATCTCGTGAACCCTATGGAATGCAATGCGTAGTCAGTCAGCCGGATTAGATACCCTAGTAGTC |
| (SEQ ID NO: 529) | CCTACGGGAGGCATCAGGCAGATCTCGAGAGTCTTGCCACGAATGAGTCATAGTCAGTCAGCCGGATTAGATACCCTAGTAGTC |
| (SEQ ID NO: 530) | CCTACGGGAGGCATCAGGCAGATCTCGACAACACTCCGACAACGCTAGAATAGTCAGTCAGCCGGATTAGATACCCTAGTAGTC |
| (SEQ ID NO: 531) | CCTACGGGAGGCATCAGGCAGATCTCGCGATGCTGTTGAATCAGAGCCCATAGTCAGTCAGCCGGATTAGATACCCTAGTAGTC |
| (SEQ ID NO: 532) | CCTACGGGAGGCATCAGGCAGATCTCGACGACTGCATAATCTGTAGAGCCAAGTCAGTCAGCCGGATTAGATACCCTAGTAGTC |
| (SEQ ID NO: 533) | CCTACGGGAGGCATCAGGCAGATCTCGACGCGAACTAATCCGACTCTAGGTAGTCAGTCAGCCGGATTAGATACCCTAGTAGTC |
| (SEQ ID NO: 534) | CCTACGGGAGGCATCAGGCAGATCTCGAGCTATGTATGGATCCTACGAGCAAGTCAGTCAGCCGGATTAGATACCCTAGTAGTC |
| (SEQ ID NO: 535) | CCTACGGGAGGCATCAGGCAGATCTCGACGGGTCATCATGACAACGAATCTAGTCAGTCAGCCGGATTAGATACCCTAGTAGTC |
| (SEQ ID NO: 536) | CCTACGGGAGGCATCAGGCAGATCTCGGAAACATCCCACTGCGGTTGACTCAGTCAGTCAGCCGGATTAGATACCCTAGTAGTC |
| (SEQ ID NO: 537) | CCTACGGGAGGCATCAGGCAGATCTCGCGTACTCTCGAGTGAGAAGAAAGGAGTCAGTCAGCCGGATTAGATACCCTAGTAGTC |
| (SEQ ID NO: 538) | CCTACGGGAGGCATCAGGCAGATCTCGTCAGTTCTCGTTTCGGATCTGTGAAGTCAGTCAGCCGGATTAGATACCCTAGTAGTC |
| (SEQ ID NO: 539) | CCTACGGGAGGCATCAGGCAGATCTCGTCGTGCGTGTTGGCCGGTACTCTAAGTCAGTCAGCCGGATTAGATACCCTAGTAGTC |
| (SEQ ID NO: 540) | CCTACGGGAGGCATCAGGCAGATCTCGGTTATCGCATGGCACAGGATTACCAGTCAGTCAGCCGGATTAGATACCCTAGTAGTC |

TABLE 3-continued

| | full sequence |
|---|---|
| (SEQ ID NO: 541) | CCTACGGGAGGCATCAGGCAGATCTCGGATCACGAGAGGCGATATCAGTAGAGTCAGTCAGCCGGATTAGATACCCTAGTAGTC |
| (SEQ ID NO: 542) | CCTACGGGAGGCATCAGGCAGATCTCGGTAAATTCAGGCCATAAGGGAGGCAGTCAGTCAGCCGGATTAGATACCCTAGTAGTC |
| (SEQ ID NO: 543) | CCTACGGGAGGCATCAGGCAGATCTCGAGTGTTTCGGACTGTGTTACTCCTAGTCAGTCAGCCGGATTAGATACCCTAGTAGTC |
| (SEQ ID NO: 544) | CCTACGGGAGGCATCAGGCAGATCTCGACACGCGGTTTAGGTACCTGCAATAGTCAGTCAGCCGGATTAGATACCCTAGTAGTC |
| (SEQ ID NO: 545) | CCTACGGGAGGCATCAGGCAGATCTCGTGGCAAATCTAGTCGCCTATAAGGAGTCAGTCAGCCGGATTAGATACCCTAGTAGTC |
| (SEQ ID NO: 546) | CCTACGGGAGGCATCAGGCAGATCTCGCACCTTACCTTAAGTGGCACTATCAGTCAGTCAGCCGGATTAGATACCCTAGTAGTC |
| (SEQ ID NO: 547) | CCTACGGGAGGCATCAGGCAGATCTCGTTAACCTTCCTGTAACCCGATAGAAGTCAGTCAGCCGGATTAGATACCCTAGTAGTC |
| (SEQ ID NO: 548) | CCTACGGGAGGCATCAGGCAGATCTCGTGCCGTATGCCAGTGTGCTAACGTAGTCAGTCAGCCGGATTAGATACCCTAGTAGTC |
| (SEQ ID NO: 549) | CCTACGGGAGGCATCAGGCAGATCTCGCGTGACAATAGTCTTGCGGCAATCAGTCAGTCAGCCGGATTAGATACCCTAGTAGTC |
| (SEQ ID NO: 550) | CCTACGGGAGGCATCAGGCAGATCTCGCGCTACAACTCGTGAGGTTTGATGAGTCAGTCAGCCGGATTAGATACCCTAGTAGTC |
| (SEQ ID NO: 551) | CCTACGGGAGGCATCAGGCAGATCTCGTTAAGACAGTCGATTGCTGGTCGAAGTCAGTCAGCCGGATTAGATACCCTAGTAGTC |
| (SEQ ID NO: 552) | CCTACGGGAGGCATCAGGCAGATCTCGTCTGCACTGAGCAAGAAGCCGGACAGTCAGTCAGCCGGATTAGATACCCTAGTAGTC |
| (SEQ ID NO: 553) | CCTACGGGAGGCATCAGGCAGATCTCGCGCAGATTAGTAACGGGATACAGGAGTCAGTCAGCCGGATTAGATACCCTAGTAGTC |
| (SEQ ID NO: 554) | CCTACGGGAGGCATCAGGCAGATCTCGTGGGTCCCACATAAGAGTCTCTAGAGTCAGTCAGCCGGATTAGATACCCTAGTAGTC |
| (SEQ ID NO: 555) | CCTACGGGAGGCATCAGGCAGATCTCGCACTGGTGCATATCCGTCATGGGTAGTCAGTCAGCCGGATTAGATACCCTAGTAGTC |
| (SEQ ID NO: 556) | CCTACGGGAGGCATCAGGCAGATCTCGAACGTAGGCTCTAGATCTATGCAGAGTCAGTCAGCCGGATTAGATACCCTAGTAGTC |
| (SEQ ID NO: 557) | CCTACGGGAGGCATCAGGCAGATCTCGAGTTGTAGTCCGGCACAAGGCAAGAGTCAGTCAGCCGGATTAGATACCCTAGTAGTC |
| (SEQ ID NO: 558) | CCTACGGGAGGCATCAGGCAGATCTCGTCGTCAAACCCGCGGCAAACACTTAGTCAGTCAGCCGGATTAGATACCCTAGTAGTC |
| (SEQ ID NO: 559) | CCTACGGGAGGCATCAGGCAGATCTCGTAATCGGTGCCAGCGAGTTCCTGTAGTCAGTCAGCCGGATTAGATACCCTAGTAGTC |
| (SEQ ID NO: 560) | CCTACGGGAGGCATCAGGCAGATCTCGTTGATCCGGTAGTTCCGAATCGGCAGTCAGTCAGCCGGATTAGATACCCTAGTAGTC |
| (SEQ ID NO: 561) | CCTACGGGAGGCATCAGGCAGATCTCGCGGGTGTTTGCTTACCTAGTGAGAAGTCAGTCAGCCGGATTAGATACCCTAGTAGTC |
| (SEQ ID NO: 562) | CCTACGGGAGGCATCAGGCAGATCTCGTTGACCGCGGTTCGTTCTGGTGGTAGTCAGTCAGCCGGATTAGATACCCTAGTAGTC |
| (SEQ ID NO: 563) | CCTACGGGAGGCATCAGGCAGATCTCGGTGCAACCAATCTTGGTCTCCTCTAGTCAGTCAGCCGGATTAGATACCCTAGTAGTC |
| (SEQ ID NO: 564) | CCTACGGGAGGCATCAGGCAGATCTCGGCTTGAGCTTGACTGCATACTGAGAGTCAGTCAGCCGGATTAGATACCCTAGTAGTC |
| (SEQ ID NO: 565) | CCTACGGGAGGCATCAGGCAGATCTCGCGCTGTGGATTACAGGGCCTTTGTAGTCAGTCAGCCGGATTAGATACCCTAGTAGTC |
| (SEQ ID NO: 566) | CCTACGGGAGGCATCAGGCAGATCTCGCTGTCAGTGACCCGATGAATATCGAGTCAGTCAGCCGGATTAGATACCCTAGTAGTC |
| (SEQ ID NO: 567) | CCTACGGGAGGCATCAGGCAGATCTCGACGATTCGAGTCGTCAATTAGTGGAGTCAGTCAGCCGGATTAGATACCCTAGTAGTC |
| (SEQ ID NO: 568) | CCTACGGGAGGCATCAGGCAGATCTCGGGTTCGGTCCATAGTACGCAGTCTAGTCAGTCAGCCGGATTAGATACCCTAGTAGTC |
| (SEQ ID NO: 569) | CCTACGGGAGGCATCAGGCAGATCTCGCTGATCCATCTTAGCAGCTATTGCAGTCAGTCAGCCGGATTAGATACCCTAGTAGTC |
| (SEQ ID NO: 570) | CCTACGGGAGGCATCAGGCAGATCTCGTATGTGCCGGCTCTCGGATAGATCAGTCAGTCAGCCGGATTAGATACCCTAGTAGTC |
| (SEQ ID NO: 571) | CCTACGGGAGGCATCAGGCAGATCTCGTGGTCGCATCGTTTCCCGAAACGAAGTCAGTCAGCCGGATTAGATACCCTAGTAGTC |
| (SEQ ID NO: 572) | CCTACGGGAGGCATCAGGCAGATCTCGTGTAAGACTTGGGAACTTTAGCGCAGTCAGTCAGCCGGATTAGATACCCTAGTAGTC |
| (SEQ ID NO: 573) | CCTACGGGAGGCATCAGGCAGATCTCGCGGATCTAGTGTTCCTTAGAAGGCAGTCAGTCAGCCGGATTAGATACCCTAGTAGTC |
| (SEQ ID NO: 574) | CCTACGGGAGGCATCAGGCAGATCTCGCGATCTTCGAGCGATGGACTTCAAAGTCAGTCAGCCGGATTAGATACCCTAGTAGTC |
| (SEQ ID NO: 575) | CCTACGGGAGGCATCAGGCAGATCTCGGTCGAATTTGCGTACTGAGCCTCGAGTCAGTCAGCCGGATTAGATACCCTAGTAGTC |
| (SEQ ID NO: 576) | CCTACGGGAGGCATCAGGCAGATCTCGGCATCAGAGTTAAGAAGGCCTTATAGTCAGTCAGCCGGATTAGATACCCTAGTAGTC |
| (SEQ ID NO: 577) | CCTACGGGAGGCATCAGGCAGATCTCGTGGTCATCGTATGGAGCCTTGTCAGTCAGTCAGCCGGATTAGATACCCTAGTAGTC |
| (SEQ ID NO: 578) | CCTACGGGAGGCATCAGGCAGATCTCGCTGAAGGGCGAACTCGATGTAAGCAGTCAGTCAGCCGGATTAGATACCCTAGTAGTC |
| (SEQ ID NO: 579) | CCTACGGGAGGCATCAGGCAGATCTCGCGCTCACAGAATAGCTTCGACAGTAGTCAGTCAGCCGGATTAGATACCCTAGTAGTC |

TABLE 3-continued

| | full sequence |
|---|---|
| (SEQ ID NO: 580) | CCTACGGGAGGCATCAGGCAGATCTCGATTCGGTAGTGCATACGCATCAAGAGTCAGTCAGCCGGATTAGATACCCTAGTAGTC |
| (SEQ ID NO: 581) | CCTACGGGAGGCATCAGGCAGATCTCGCGAGCTGTTACCAGATGTCCGTCAAGTCAGTCAGCCGGATTAGATACCCTAGTAGTC |
| (SEQ ID NO: 582) | CCTACGGGAGGCATCAGGCAGATCTCGCAACACATGCTGGCACCTGTTGAAAGTCAGTCAGCCGGATTAGATACCCTAGTAGTC |
| (SEQ ID NO: 583) | CCTACGGGAGGCATCAGGCAGATCTCGATTCTCTCACGTCCTAGAGAAACTAGTCAGTCAGCCGGATTAGATACCCTAGTAGTC |
| (SEQ ID NO: 584) | CCTACGGGAGGCATCAGGCAGATCTCGCGACTCTAAACGGAGGTTCTTGACAGTCAGTCAGCCGGATTAGATACCCTAGTAGTC |
| (SEQ ID NO: 585) | CCTACGGGAGGCATCAGGCAGATCTCGGTCTTCAGCAAGCTGTAAAGGTTGAGTCAGTCAGCCGGATTAGATACCCTAGTAGTC |
| (SEQ ID NO: 586) | CCTACGGGAGGCATCAGGCAGATCTCGCGGATAACCTCCTGAGTCATTGAGAGTCAGTCAGCCGGATTAGATACCCTAGTAGTC |
| (SEQ ID NO: 587) | CCTACGGGAGGCATCAGGCAGATCTCGAGGGTGACTTTATACGGCAGTTCAAGTCAGTCAGCCGGATTAGATACCCTAGTAGTC |
| (SEQ ID NO: 588) | CCTACGGGAGGCATCAGGCAGATCTCGGACTTCATGCGACTCTAGAAGAGTAGTCAGTCAGCCGGATTAGATACCCTAGTAGTC |
| (SEQ ID NO: 589) | CCTACGGGAGGCATCAGGCAGATCTCGGCCTGTCTGCAATGCACAGTCGCTAGTCAGTCAGCCGGATTAGATACCCTAGTAGTC |
| (SEQ ID NO: 590) | CCTACGGGAGGCATCAGGCAGATCTCGACTGATGGCCTCCATGCGGATCCTAGTCAGTCAGCCGGATTAGATACCCTAGTAGTC |
| (SEQ ID NO: 591) | CCTACGGGAGGCATCAGGCAGATCTCGTTCGATGCCGCATGCTCCGTAGAAAGTCAGTCAGCCGGATTAGATACCCTAGTAGTC |
| (SEQ ID NO: 592) | CCTACGGGAGGCATCAGGCAGATCTCGTGTGGCTCGTGTTGATAGGTACACAGTCAGTCAGCCGGATTAGATACCCTAGTAGTC |
| (SEQ ID NO: 593) | CCTACGGGAGGCATCAGGCAGATCTCGAACTTTCAGGAGCGAGTTCATCGAAGTCAGTCAGCCGGATTAGATACCCTAGTAGTC |
| (SEQ ID NO: 594) | CCTACGGGAGGCATCAGGCAGATCTCGTGCACGTGATAAAAGCAGATTGTCAGTCAGCCGGATTAGATACCCTAGTAGTC |
| (SEQ ID NO: 595) | CCTACGGGAGGCATCAGGCAGATCTCGGTTCGGTGTCCATAGAGGCGTAGGAGTCAGTCAGCCGGATTAGATACCCTAGTAGTC |
| (SEQ ID NO: 596) | CCTACGGGAGGCATCAGGCAGATCTCGAAGACAGCTATCTCAGCGCCGTTAAGTCAGTCAGCCGGATTAGATACCCTAGTAGTC |
| (SEQ ID NO: 597) | CCTACGGGAGGCATCAGGCAGATCTCGATTGACCGGTCATAGACCGACTCCAGTCAGTCAGCCGGATTAGATACCCTAGTAGTC |
| (SEQ ID NO: 598) | CCTACGGGAGGCATCAGGCAGATCTCGTTCTCCATCACAGTCAACGCTGTCAGTCAGCCGGATTAGATACCCTAGTAGTC |
| (SEQ ID NO: 599) | CCTACGGGAGGCATCAGGCAGATCTCGCGTAGGTAGAGGACAGGAGGGTGTAGTCAGTCAGCCGGATTAGATACCCTAGTAGTC |
| (SEQ ID NO: 600) | CCTACGGGAGGCATCAGGCAGATCTCGATTTAGGACGACGCTGTCGTCAACAGTCAGTCAGCCGGATTAGATACCCTAGTAGTC |
| (SEQ ID NO: 601) | CCTACGGGAGGCATCAGGCAGATCTCGGGATAGCCAAGGATAGAGGCCATTAGTCAGTCAGCCGGATTAGATACCCTAGTAGTC |
| (SEQ ID NO: 602) | CCTACGGGAGGCATCAGGCAGATCTCGTGGTTGGTTACGAAGCTTGAAACCAGTCAGTCAGCCGGATTAGATACCCTAGTAGTC |
| (SEQ ID NO: 603) | CCTACGGGAGGCATCAGGCAGATCTCGGTCGTCCAAATGTAAGCGTCTCGAAGTCAGTCAGCCGGATTAGATACCCTAGTAGTC |
| (SEQ ID NO: 604) | CCTACGGGAGGCATCAGGCAGATCTCGCAACGTGCTCCAATAGCTTCGTGGAGTCAGTCAGCCGGATTAGATACCCTAGTAGTC |
| (SEQ ID NO: 605) | CCTACGGGAGGCATCAGGCAGATCTCGTACACAAGTCGCCGGGATCAAATTAGTCAGTCAGCCGGATTAGATACCCTAGTAGTC |
| (SEQ ID NO: 606) | CCTACGGGAGGCATCAGGCAGATCTCGGCGTCCATGAATAGTCATCGAATGAGTCAGTCAGCCGGATTAGATACCCTAGTAGTC |
| (SEQ ID NO: 607) | CCTACGGGAGGCATCAGGCAGATCTCGGTAATGCGTAACATCTTGGAGTCGAGTCAGTCAGCCGGATTAGATACCCTAGTAGTC |
| (SEQ ID NO: 608) | CCTACGGGAGGCATCAGGCAGATCTCGGTCGCCGTACATAGCACCGGTCTTAGTCAGTCAGCCGGATTAGATACCCTAGTAGTC |
| (SEQ ID NO: 609) | CCTACGGGAGGCATCAGGCAGATCTCGGGAATCCGATTAGCAAATCAGCCTAGTCAGTCAGCCGGATTAGATACCCTAGTAGTC |
| (SEQ ID NO: 610) | CCTACGGGAGGCATCAGGCAGATCTCGCACCCGATGGTTGCAAGCTGTCTCAGTCAGTCAGCCGGATTAGATACCCTAGTAGTC |
| (SEQ ID NO: 611) | CCTACGGGAGGCATCAGGCAGATCTCGTTCTGAGAGGTAAGCGGCCTATTAAGTCAGTCAGCCGGATTAGATACCCTAGTAGTC |
| (SEQ ID NO: 612) | CCTACGGGAGGCATCAGGCAGATCTCGATCCCTACGGAATCTTCAACTACCAGTCAGTCAGCCGGATTAGATACCCTAGTAGTC |
| (SEQ ID NO: 613) | CCTACGGGAGGCATCAGGCAGATCTCGGGTTCCATTAGGTGGAATTCGGCTAGTCAGTCAGCCGGATTAGATACCCTAGTAGTC |
| (SEQ ID NO: 614) | CCTACGGGAGGCATCAGGCAGATCTCGGTGTTCCCAGAATAAGATGCAGTCAGTCAGCCGGATTAGATACCCTAGTAGTC |
| (SEQ ID NO: 615) | CCTACGGGAGGCATCAGGCAGATCTCGCCGAGGTATAATTGCCGAGTAATCAGTCAGCCGGATTAGATACCCTAGTAGTC |
| (SEQ ID NO: 616) | CCTACGGGAGGCATCAGGCAGATCTCGAGCGTAATTAGCACCTTGACAAGAAGTCAGTCAGCCGGATTAGATACCCTAGTAGTC |
| (SEQ ID NO: 617) | CCTACGGGAGGCATCAGGCAGATCTCGCTCGTGAATGACGTAACCACCACCAGTCAGTCAGCCGGATTAGATACCCTAGTAGTC |
| (SEQ ID NO: 618) | CCTACGGGAGGCATCAGGCAGATCTCGAGGTGAGTTCTACATAGCTCGGTCAGTCAGTCAGCCGGATTAGATACCCTAGTAGTC |

TABLE 3-continued

| | full sequence |
|---|---|
| (SEQ ID NO: 619) | CCTACGGGAGGCATCAGGCAGATCTCGCCTGTCCTATCTAACCATGCCAACAGTCAGTCAGCCGGATTAGATACCCTAGTAGTC |
| (SEQ ID NO: 620) | CCTACGGGAGGCATCAGGCAGATCTCGGGTTTAACACGCTATGGAGCTAGTAGTCAGTCAGCCGGATTAGATACCCTAGTAGTC |
| (SEQ ID NO: 621) | CCTACGGGAGGCATCAGGCAGATCTCGAGACAGTAGGAGACTACCTCTTCAAGTCAGTCAGCCGGATTAGATACCCTAGTAGTC |
| (SEQ ID NO: 622) | CCTACGGGAGGCATCAGGCAGATCTCGGCCACGACTTACGATGATAACCCAAGTCAGTCAGCCGGATTAGATACCCTAGTAGTC |
| (SEQ ID NO: 623) | CCTACGGGAGGCATCAGGCAGATCTCGATTGTTCCTACCGGCCCAATATAAAGTCAGTCAGCCGGATTAGATACCCTAGTAGTC |
| (SEQ ID NO: 624) | CCTACGGGAGGCATCAGGCAGATCTCGGCCGTAAACTTGTTGTATGACAGGAGTCAGTCAGCCGGATTAGATACCCTAGTAGTC |
| (SEQ ID NO: 625) | CCTACGGGAGGCATCAGGCAGATCTCGGCAGATTTCCAGGGTAAGTTTGACAGTCAGTCAGCCGGATTAGATACCCTAGTAGTC |
| (SEQ ID NO: 626) | CCTACGGGAGGCATCAGGCAGATCTCGAGATGATCAGTCCTACCACGGTACAGTCAGTCAGCCGGATTAGATACCCTAGTAGTC |
| (SEQ ID NO: 627) | CCTACGGGAGGCATCAGGCAGATCTCGGAGACGTGTTCTCGGTCTGTCTGAAGTCAGTCAGCCGGATTAGATACCCTAGTAGTC |
| (SEQ ID NO: 628) | CCTACGGGAGGCATCAGGCAGATCTCGTATCACCGGCACGTACATGTCGCCAGTCAGTCAGCCGGATTAGATACCCTAGTAGTC |
| (SEQ ID NO: 629) | CCTACGGGAGGCATCAGGCAGATCTCGTATGCCAGAGATTTCTAGAGTGCGAGTCAGTCAGCCGGATTAGATACCCTAGTAGTC |
| (SEQ ID NO: 630) | CCTACGGGAGGCATCAGGCAGATCTCGAGGTCCAAATCAACGGATGTTATGAGTCAGTCAGCCGGATTAGATACCCTAGTAGTC |
| (SEQ ID NO: 631) | CCTACGGGAGGCATCAGGCAGATCTCGACCGTGCTCACATTGAGGCTACAAAGTCAGTCAGCCGGATTAGATACCCTAGTAGTC |
| (SEQ ID NO: 632) | CCTACGGGAGGCATCAGGCAGATCTCGCTCCCTTTGTGTGTAGGAACCGGAAGTCAGTCAGCCGGATTAGATACCCTAGTAGTC |
| (SEQ ID NO: 633) | CCTACGGGAGGCATCAGGCAGATCTCGAGCTGCACCTAAACATCTAGCAGAAGTCAGTCAGCCGGATTAGATACCCTAGTAGTC |
| (SEQ ID NO: 634) | CCTACGGGAGGCATCAGGCAGATCTCGCCTTGACCGATGCCGACATTGTAGAGTCAGTCAGCCGGATTAGATACCCTAGTAGTC |
| (SEQ ID NO: 635) | CCTACGGGAGGCATCAGGCAGATCTCGCTATCATCCTCACATGTAAGGCTCAGTCAGTCAGCCGGATTAGATACCCTAGTAGTC |
| (SEQ ID NO: 636) | CCTACGGGAGGCATCAGGCAGATCTCGACTCTAGCCGGTTGCAAGCTAAGTAGTCAGTCAGCCGGATTAGATACCCTAGTAGTC |
| (SEQ ID NO: 637) | CCTACGGGAGGCATCAGGCAGATCTCGCGATAGGCCTTAGTGTGTGCCATAAGTCAGTCAGCCGGATTAGATACCCTAGTAGTC |
| (SEQ ID NO: 638) | CCTACGGGAGGCATCAGGCAGATCTCGAATGACCTCGTGTGACAACCGAATAGTCAGTCAGCCGGATTAGATACCCTAGTAGTC |
| (SEQ ID NO: 639) | CCTACGGGAGGCATCAGGCAGATCTCGCTTAGGCATGTGTAGGCTCGTGCTAGTCAGTCAGCCGGATTAGATACCCTAGTAGTC |
| (SEQ ID NO: 640) | CCTACGGGAGGCATCAGGCAGATCTCGCCAGATATAGCACTCCTTAAGGCGAGTCAGTCAGCCGGATTAGATACCCTAGTAGTC |
| (SEQ ID NO: 641) | CCTACGGGAGGCATCAGGCAGATCTCGGAGAGTCCACTTTTGCCTGGGTCAAGTCAGTCAGCCGGATTAGATACCCTAGTAGTC |
| (SEQ ID NO: 642) | CCTACGGGAGGCATCAGGCAGATCTCGGAACGGGACGTACAATTCTGCTTCAGTCAGTCAGCCGGATTAGATACCCTAGTAGTC |
| (SEQ ID NO: 643) | CCTACGGGAGGCATCAGGCAGATCTCGACGTGTAGGCTTACTGGCAAACCTAGTCAGTCAGCCGGATTAGATACCCTAGTAGTC |
| (SEQ ID NO: 644) | CCTACGGGAGGCATCAGGCAGATCTCGGGTCTCCTACAGAATCAGAGCTTGAGTCAGTCAGCCGGATTAGATACCCTAGTAGTC |
| (SEQ ID NO: 645) | CCTACGGGAGGCATCAGGCAGATCTCGACTGACTTAAGGCAATGTAGACACAGTCAGTCAGCCGGATTAGATACCCTAGTAGTC |
| (SEQ ID NO: 646) | CCTACGGGAGGCATCAGGCAGATCTCGGATGCTGCCGTTTGGCGATACGTTAGTCAGTCAGCCGGATTAGATACCCTAGTAGTC |
| (SEQ ID NO: 647) | CCTACGGGAGGCATCAGGCAGATCTCGTTCCTAGGCCAGGCCTTACGATAGAGTCAGTCAGCCGGATTAGATACCCTAGTAGTC |
| (SEQ ID NO: 648) | CCTACGGGAGGCATCAGGCAGATCTCGATTAAGCCTGGATACCTGTGTCTTAGTCAGTCAGCCGGATTAGATACCCTAGTAGTC |
| (SEQ ID NO: 649) | CCTACGGGAGGCATCAGGCAGATCTCGTGGCTTTCTATCAACGAGGCAACGAGTCAGTCAGCCGGATTAGATACCCTAGTAGTC |
| (SEQ ID NO: 650) | CCTACGGGAGGCATCAGGCAGATCTCGACAGCTCAAACAGAAGACAGCGACAGTCAGTCAGCCGGATTAGATACCCTAGTAGTC |
| (SEQ ID NO: 651) | CCTACGGGAGGCATCAGGCAGATCTCGGAGCGTATCCATACACCTGCGATCAGTCAGTCAGCCGGATTAGATACCCTAGTAGTC |
| (SEQ ID NO: 652) | CCTACGGGAGGCATCAGGCAGATCTCGATGGGCGAATGGGCGTTGCATTCAGTCAGTCAGCCGGATTAGATACCCTAGTAGTC |
| (SEQ ID NO: 653) | CCTACGGGAGGCATCAGGCAGATCTCGGATCTCTGGGTAACTAGCGTTCAGAGTCAGTCAGCCGGATTAGATACCCTAGTAGTC |
| (SEQ ID NO: 654) | CCTACGGGAGGCATCAGGCAGATCTCGCATCATACGGGTTTGCGACAAAGTAGTCAGTCAGCCGGATTAGATACCCTAGTAGTC |
| (SEQ ID NO: 655) | CCTACGGGAGGCATCAGGCAGATCTCGTACGGATTATGGTGCGAGTATATGAGTCAGTCAGCCGGATTAGATACCCTAGTAGTC |
| (SEQ ID NO: 656) | CCTACGGGAGGCATCAGGCAGATCTCGATAGCGAACTCATACCACAACGAAAGTCAGTCAGCCGGATTAGATACCCTAGTAGTC |
| (SEQ ID NO: 657) | CCTACGGGAGGCATCAGGCAGATCTCGTAACGCTGTGTGTCTGGAACGGTTAGTCAGTCAGCCGGATTAGATACCCTAGTAGTC |

TABLE 3-continued

|  | full sequence |
| --- | --- |
| (SEQ ID NO: 658) | CCTACGGGAGGCATCAGGCAGATCTCGAACCAAACTCGAGTACTACCTCGGAGTCAGTCAGCCGGATTAGATACCCTAGTAGTC |
| (SEQ ID NO: 659) | CCTACGGGAGGCATCAGGCAGATCTCGGCCGTCTCGTAATTCCTGTTAACCAGTCAGTCAGCCGGATTAGATACCCTAGTAGTC |
| (SEQ ID NO: 660) | CCTACGGGAGGCATCAGGCAGATCTCGCTGGGTATCTCGCTATCCAAGTGGAGTCAGTCAGCCGGATTAGATACCCTAGTAGTC |
| (SEQ ID NO: 661) | CCTACGGGAGGCATCAGGCAGATCTCGGACTACCCGTTGCAGTCTAGTACGAGTCAGTCAGCCGGATTAGATACCCTAGTAGTC |
| (SEQ ID NO: 662) | CCTACGGGAGGCATCAGGCAGATCTCGGCGTTGCAAACTGTGTCCGGATTCAGTCAGTCAGCCGGATTAGATACCCTAGTAGTC |
| (SEQ ID NO: 663) | CCTACGGGAGGCATCAGGCAGATCTCGAACCGCATAAGTTGTGGTGATGTAAGTCAGTCAGCCGGATTAGATACCCTAGTAGTC |
| (SEQ ID NO: 664) | CCTACGGGAGGCATCAGGCAGATCTCGACCTTACACCTTCTTTCGTTCAACAGTCAGTCAGCCGGATTAGATACCCTAGTAGTC |
| (SEQ ID NO: 665) | CCTACGGGAGGCATCAGGCAGATCTCGGTAGGTGCTTACCCGAAGATTCTGAGTCAGTCAGCCGGATTAGATACCCTAGTAGTC |
| (SEQ ID NO: 666) | CCTACGGGAGGCATCAGGCAGATCTCGCGCATTTGGATGGTTGGCGTTACAAGTCAGTCAGCCGGATTAGATACCCTAGTAGTC |
| (SEQ ID NO: 667) | CCTACGGGAGGCATCAGGCAGATCTCGATAACATGTGCGGAAGTAGCGAGCAGTCAGTCAGCCGGATTAGATACCCTAGTAGTC |
| (SEQ ID NO: 668) | CCTACGGGAGGCATCAGGCAGATCTCGCTTGAGAAATCGTTGCGGACCCTAAGTCAGTCAGCCGGATTAGATACCCTAGTAGTC |
| (SEQ ID NO: 669) | CCTACGGGAGGCATCAGGCAGATCTCGCTACACAGCACAGCGGAAACATGGAGTCAGTCAGCCGGATTAGATACCCTAGTAGTC |
| (SEQ ID NO: 670) | CCTACGGGAGGCATCAGGCAGATCTCGGAAATGCTACGTAACGTTAGTGTGAGTCAGTCAGCCGGATTAGATACCCTAGTAGTC |
| (SEQ ID NO: 671) | CCTACGGGAGGCATCAGGCAGATCTCGTCTGAGGTTGCCTGCATGACAGTCAGTCAGCCGGATTAGATACCCTAGTAGTC |
| (SEQ ID NO: 672) | CCTACGGGAGGCATCAGGCAGATCTCGGATCATTCTCTCTCAATCGCTTTCAGTCAGTCAGCCGGATTAGATACCCTAGTAGTC |
| (SEQ ID NO: 673) | CCTACGGGAGGCATCAGGCAGATCTCGAGACATACCGTACTACCGATTGCGAGTCAGTCAGCCGGATTAGATACCCTAGTAGTC |
| (SEQ ID NO: 674) | CCTACGGGAGGCATCAGGCAGATCTCGGATCCTCATGCGTCACCCAAGGTAAGTCAGTCAGCCGGATTAGATACCCTAGTAGTC |
| (SEQ ID NO: 675) | CCTACGGGAGGCATCAGGCAGATCTCGATTATCGTCCCTAGCCAGTCATACAGTCAGTCAGCCGGATTAGATACCCTAGTAGTC |
| (SEQ ID NO: 676) | CCTACGGGAGGCATCAGGCAGATCTCGCCAGACCGCTATTAACGGCGCTCTAGTCAGTCAGCCGGATTAGATACCCTAGTAGTC |
| (SEQ ID NO: 677) | CCTACGGGAGGCATCAGGCAGATCTCGAGCTCTAGAAACGTTTGCTCGAGAAGTCAGTCAGCCGGATTAGATACCCTAGTAGTC |
| (SEQ ID NO: 678) | CCTACGGGAGGCATCAGGCAGATCTCGTCCATCGACGTGCAAACGCACTAAAGTCAGTCAGCCGGATTAGATACCCTAGTAGTC |
| (SEQ ID NO: 679) | CCTACGGGAGGCATCAGGCAGATCTCGCGATGTGTGGTTGAACAAAGAGCGAGTCAGTCAGCCGGATTAGATACCCTAGTAGTC |
| (SEQ ID NO: 680) | CCTACGGGAGGCATCAGGCAGATCTCGGCGAAGTTGGGAGCTAAGTGATGTAGTCAGTCAGCCGGATTAGATACCCTAGTAGTC |
| (SEQ ID NO: 681) | CCTACGGGAGGCATCAGGCAGATCTCGGCATTCGGCGTTAAGGGACAAGTGAGTCAGTCAGCCGGATTAGATACCCTAGTAGTC |
| (SEQ ID NO: 682) | CCTACGGGAGGCATCAGGCAGATCTCGCGCCATTGTGCAAGTGTCGATTCGAGTCAGTCAGCCGGATTAGATACCCTAGTAGTC |
| (SEQ ID NO: 683) | CCTACGGGAGGCATCAGGCAGATCTCGTCCAACTGCAGACTATTAAGCGGCAGTCAGTCAGCCGGATTAGATACCCTAGTAGTC |
| (SEQ ID NO: 684) | CCTACGGGAGGCATCAGGCAGATCTCGTAAAGACCCGTACCTACCATTGTTAGTCAGTCAGCCGGATTAGATACCCTAGTAGTC |
| (SEQ ID NO: 685) | CCTACGGGAGGCATCAGGCAGATCTCGTGTATCTTCACCGAGTCCGTTGCTAGTCAGTCAGCCGGATTAGATACCCTAGTAGTC |
| (SEQ ID NO: 686) | CCTACGGGAGGCATCAGGCAGATCTCGGACTGACTCGTCGATAACTGTACGAGTCAGTCAGCCGGATTAGATACCCTAGTAGTC |
| (SEQ ID NO: 687) | CCTACGGGAGGCATCAGGCAGATCTCGTCGTGGATAGCTTAAACCTGGACAAGTCAGTCAGCCGGATTAGATACCCTAGTAGTC |
| (SEQ ID NO: 688) | CCTACGGGAGGCATCAGGCAGATCTCGGACGCACTAACTCCGAATTGACAAAGTCAGTCAGCCGGATTAGATACCCTAGTAGTC |
| (SEQ ID NO: 689) | CCTACGGGAGGCATCAGGCAGATCTCGGGCGATTACGTCTGGCATCTAGCAGTCAGTCAGCCGGATTAGATACCCTAGTAGTC |
| (SEQ ID NO: 690) | CCTACGGGAGGCATCAGGCAGATCTCGTAAGGCATCGCTGGTGGTCGTTCTAGTCAGTCAGCCGGATTAGATACCCTAGTAGTC |
| (SEQ ID NO: 691) | CCTACGGGAGGCATCAGGCAGATCTCGACCCATACAGCCACTATGGGCTAAAGTCAGTCAGCCGGATTAGATACCCTAGTAGTC |
| (SEQ ID NO: 692) | CCTACGGGAGGCATCAGGCAGATCTCGCGCACTACGCATGCATTGAGTTCGAGTCAGTCAGCCGGATTAGATACCCTAGTAGTC |
| (SEQ ID NO: 693) | CCTACGGGAGGCATCAGGCAGATCTCGCAGTCGTTAAGAGTTGCTGAGTCCAGTCAGTCAGCCGGATTAGATACCCTAGTAGTC |
| (SEQ ID NO: 694) | CCTACGGGAGGCATCAGGCAGATCTCGCTACGAAAGCCTCTATGGTGAACCAGTCAGTCAGCCGGATTAGATACCCTAGTAGTC |
| (SEQ ID NO: 695) | CCTACGGGAGGCATCAGGCAGATCTCGATAATTGCCGAGGGACCAAGGGATAGTCAGTCAGCCGGATTAGATACCCTAGTAGTC |
| (SEQ ID NO: 696) | CCTACGGGAGGCATCAGGCAGATCTCGGGCATGTTATCGGTATTGGTCAGAAGTCAGTCAGCCGGATTAGATACCCTAGTAGTC |

TABLE 3-continued

| | full sequence |
|---|---|
| (SEQ ID NO: 697) | CCTACGGGAGGCATCAGGCAGATCTCGAGGCACAGTAGGAGAACCGTCATAAGTCAGTCAGCCGGATTAGATACCCTAGTAGTC |
| (SEQ ID NO: 698) | CCTACGGGAGGCATCAGGCAGATCTCGCTACTTACATCCAACTGGAACCCTAGTCAGTCAGCCGGATTAGATACCCTAGTAGTC |
| (SEQ ID NO: 699) | CCTACGGGAGGCATCAGGCAGATCTCGCTCTTCTGATCAATACTCGGCTGCAGTCAGTCAGCCGGATTAGATACCCTAGTAGTC |
| (SEQ ID NO: 700) | CCTACGGGAGGCATCAGGCAGATCTCGATGCTAACCACGACGCTTAACGACAGTCAGTCAGCCGGATTAGATACCCTAGTAGTC |
| (SEQ ID NO: 701) | CCTACGGGAGGCATCAGGCAGATCTCGACCAATCTCGGCAGCTTACCGACCAGTCAGTCAGCCGGATTAGATACCCTAGTAGTC |
| (SEQ ID NO: 702) | CCTACGGGAGGCATCAGGCAGATCTCGTATCCAAGCGCAAGGGCTATAGTTAGTCAGTCAGCCGGATTAGATACCCTAGTAGTC |
| (SEQ ID NO: 703) | CCTACGGGAGGCATCAGGCAGATCTCGGTACTGAAGATCTGTCTCGCAAGCAGTCAGTCAGCCGGATTAGATACCCTAGTAGTC |
| (SEQ ID NO: 704) | CCTACGGGAGGCATCAGGCAGATCTCGTCGCCGTGTACACAGCCGCATATCAGTCAGTCAGCCGGATTAGATACCCTAGTAGTC |
| (SEQ ID NO: 705) | CCTACGGGAGGCATCAGGCAGATCTCGAACTGCGATATGGATACGTTCGCAAGTCAGTCAGCCGGATTAGATACCCTAGTAGTC |
| (SEQ ID NO: 706) | CCTACGGGAGGCATCAGGCAGATCTCGCTTCCAACTCATCCAAGATTCGCCAGTCAGTCAGCCGGATTAGATACCCTAGTAGTC |
| (SEQ ID NO: 707) | CCTACGGGAGGCATCAGGCAGATCTCGGAGATCGCCTATGAGGCTGATTTAAGTCAGTCAGCCGGATTAGATACCCTAGTAGTC |
| (SEQ ID NO: 708) | CCTACGGGAGGCATCAGGCAGATCTCGTGTACATCGCCGGAGTTAGCATCAAGTCAGTCAGCCGGATTAGATACCCTAGTAGTC |
| (SEQ ID NO: 709) | CCTACGGGAGGCATCAGGCAGATCTCGTGTTAAGCAGCATGTAGTATAGGCAGTCAGTCAGCCGGATTAGATACCCTAGTAGTC |
| (SEQ ID NO: 710) | CCTACGGGAGGCATCAGGCAGATCTCGACGGCGTTATGTCTCACGCAATGCAGTCAGTCAGCCGGATTAGATACCCTAGTAGTC |
| (SEQ ID NO: 711) | CCTACGGGAGGCATCAGGCAGATCTCGACTTTGCTTTGCGTCCCGTGAAATAGTCAGTCAGCCGGATTAGATACCCTAGTAGTC |
| (SEQ ID NO: 712) | CCTACGGGAGGCATCAGGCAGATCTCGCAAAGCGGTATTGGACAGTGTATTAGTCAGTCAGCCGGATTAGATACCCTAGTAGTC |
| (SEQ ID NO: 713) | CCTACGGGAGGCATCAGGCAGATCTCGCGAAACTACGTAACACGACTATAGAGTCAGTCAGCCGGATTAGATACCCTAGTAGTC |
| (SEQ ID NO: 714) | CCTACGGGAGGCATCAGGCAGATCTCGGAGGACCAGCAAGTGTAGGTGCTTAGTCAGTCAGCCGGATTAGATACCCTAGTAGTC |
| (SEQ ID NO: 715) | CCTACGGGAGGCATCAGGCAGATCTCGAATAGCATGTCGTGAACTAGCGTCAGTCAGCCGGATTAGATACCCTAGTAGTC |
| (SEQ ID NO: 716) | CCTACGGGAGGCATCAGGCAGATCTCGCGGAGTAATCCTTCCGAGTCACCAAGTCAGTCAGCCGGATTAGATACCCTAGTAGTC |
| (SEQ ID NO: 717) | CCTACGGGAGGCATCAGGCAGATCTCGCTGTGTCCATGGTCCTCTTTGGTCAGTCAGTCAGCCGGATTAGATACCCTAGTAGTC |
| (SEQ ID NO: 718) | CCTACGGGAGGCATCAGGCAGATCTCGCTTCGCGGATGTTCCACCCTCTATAGTCAGTCAGCCGGATTAGATACCCTAGTAGTC |
| (SEQ ID NO: 719) | CCTACGGGAGGCATCAGGCAGATCTCGATAGGCTGTAGTTCGTGACGCTAAAGTCAGTCAGCCGGATTAGATACCCTAGTAGTC |
| (SEQ ID NO: 720) | CCTACGGGAGGCATCAGGCAGATCTCGTGTGTAGCCATGACGGCTAGTTCCAGTCAGTCAGCCGGATTAGATACCCTAGTAGTC |
| (SEQ ID NO: 721) | CCTACGGGAGGCATCAGGCAGATCTCGAAGGGCGCTGAAGCACTGGCATATAGTCAGTCAGCCGGATTAGATACCCTAGTAGTC |
| (SEQ ID NO: 722) | CCTACGGGAGGCATCAGGCAGATCTCGGTTTCCGTGGTGGGCATTAGTTGAAGTCAGTCAGCCGGATTAGATACCCTAGTAGTC |
| (SEQ ID NO: 723) | CCTACGGGAGGCATCAGGCAGATCTCGAGGAACCAGACGCGGTAGTTGATCAGTCAGTCAGCCGGATTAGATACCCTAGTAGTC |
| (SEQ ID NO: 724) | CCTACGGGAGGCATCAGGCAGATCTCGTAATGCCCAGGTTGAAAGCGGCGAAGTCAGTCAGCCGGATTAGATACCCTAGTAGTC |
| (SEQ ID NO: 725) | CCTACGGGAGGCATCAGGCAGATCTCGTATGAACGTCCGGGTTACGGTTACAGTCAGTCAGCCGGATTAGATACCCTAGTAGTC |
| (SEQ ID NO: 726) | CCTACGGGAGGCATCAGGCAGATCTCGCCACATTGGGTCACATCAGGTCACAGTCAGTCAGCCGGATTAGATACCCTAGTAGTC |
| (SEQ ID NO: 727) | CCTACGGGAGGCATCAGGCAGATCTCGTCAGTCAGATGAGTTGATACGATGAGTCAGTCAGCCGGATTAGATACCCTAGTAGTC |
| (SEQ ID NO: 728) | CCTACGGGAGGCATCAGGCAGATCTCGAAGTCACACACAGACACTTCCGAGTCAGTCAGCCGGATTAGATACCCTAGTAGTC |
| (SEQ ID NO: 729) | CCTACGGGAGGCATCAGGCAGATCTCGGCTGTGATTCGATCACCATCCGAGAGTCAGTCAGCCGGATTAGATACCCTAGTAGTC |
| (SEQ ID NO: 730) | CCTACGGGAGGCATCAGGCAGATCTCGCTAGCTATGGACACCCACCACTAGAGTCAGTCAGCCGGATTAGATACCCTAGTAGTC |
| (SEQ ID NO: 731) | CCTACGGGAGGCATCAGGCAGATCTCGCTTGACGAGGTTCAGAAGGTGTGGAGTCAGTCAGCCGGATTAGATACCCTAGTAGTC |
| (SEQ ID NO: 732) | CCTACGGGAGGCATCAGGCAGATCTCGACCTGGGAATATGAAGCTTGAATCAGTCAGTCAGCCGGATTAGATACCCTAGTAGTC |
| (SEQ ID NO: 733) | CCTACGGGAGGCATCAGGCAGATCTCGCTCTGCCTAATTACTAGGATCAGTAGTCAGTCAGCCGGATTAGATACCCTAGTAGTC |
| (SEQ ID NO: 734) | CCTACGGGAGGCATCAGGCAGATCTCGATATGACCCAGCGCTCCTTAGAAGAGTCAGTCAGCCGGATTAGATACCCTAGTAGTC |
| (SEQ ID NO: 735) | CCTACGGGAGGCATCAGGCAGATCTCGCTCTATTCCACCTCCCATTCCCATAGTCAGTCAGCCGGATTAGATACCCTAGTAGTC |

TABLE 3-continued

| | full sequence |
|---|---|
| (SEQ ID NO: 736) | CCTACGGGAGGCATCAGGCAGATCTCGATTGAGTGAGTCTGGCGTCATTCGAGTCAGTCAGCCGGATTAGATACCCTAGTAGTC |
| (SEQ ID NO: 737) | CCTACGGGAGGCATCAGGCAGATCTCGTTATGGTACGGAAATCCTCGGAGTAGTCAGTCAGCCGGATTAGATACCCTAGTAGTC |
| (SEQ ID NO: 738) | CCTACGGGAGGCATCAGGCAGATCTCGGCTAGTTATGGACTGGACGCATTAAGTCAGTCAGCCGGATTAGATACCCTAGTAGTC |
| (SEQ ID NO: 739) | CCTACGGGAGGCATCAGGCAGATCTCGCAGATTAACCAGACCGATTAGGTAAGTCAGTCAGCCGGATTAGATACCCTAGTAGTC |
| (SEQ ID NO: 740) | CCTACGGGAGGCATCAGGCAGATCTCGGGCTGCATACTCATGTGCTGCTCGAGTCAGTCAGCCGGATTAGATACCCTAGTAGTC |
| (SEQ ID NO: 741) | CCTACGGGAGGCATCAGGCAGATCTCGTTGGTAAAGTGCTACGTACGAAACAGTCAGTCAGCCGGATTAGATACCCTAGTAGTC |
| (SEQ ID NO: 742) | CCTACGGGAGGCATCAGGCAGATCTCGAAGTGGCTATCCATCACATTCTCCAGTCAGTCAGCCGGATTAGATACCCTAGTAGTC |
| (SEQ ID NO: 743) | CCTACGGGAGGCATCAGGCAGATCTCGAACCGATGTACCAGCCTGGTACCTAGTCAGTCAGCCGGATTAGATACCCTAGTAGTC |
| (SEQ ID NO: 744) | CCTACGGGAGGCATCAGGCAGATCTCGTCGATTGGCCGTGCTAAAGTCGTAAGTCAGTCAGCCGGATTAGATACCCTAGTAGTC |
| (SEQ ID NO: 745) | CCTACGGGAGGCATCAGGCAGATCTCGGCATTACTGGACTCTCAGCGCGTAAGTCAGTCAGCCGGATTAGATACCCTAGTAGTC |
| (SEQ ID NO: 746) | CCTACGGGAGGCATCAGGCAGATCTCGTTGGGCCACATAGACCCTAGACCTAGTCAGTCAGCCGGATTAGATACCCTAGTAGTC |
| (SEQ ID NO: 747) | CCTACGGGAGGCATCAGGCAGATCTCGCACACAAAGTCATATTCAGCGGACAGTCAGTCAGCCGGATTAGATACCCTAGTAGTC |
| (SEQ ID NO: 748) | CCTACGGGAGGCATCAGGCAGATCTCGGCCAAGGATAGGGTTCCGGATTAGAGTCAGTCAGCCGGATTAGATACCCTAGTAGTC |
| (SEQ ID NO: 749) | CCTACGGGAGGCATCAGGCAGATCTCGCGCCACGTGTATGCGTGTAATTAGAGTCAGTCAGCCGGATTAGATACCCTAGTAGTC |
| (SEQ ID NO: 750) | CCTACGGGAGGCATCAGGCAGATCTCGGCAACCGATTGTCTGTAGCTTGGCAGTCAGTCAGCCGGATTAGATACCCTAGTAGTC |
| (SEQ ID NO: 751) | CCTACGGGAGGCATCAGGCAGATCTCGCATGTGCTTAGGATGCCTCGTAAGAGTCAGTCAGCCGGATTAGATACCCTAGTAGTC |
| (SEQ ID NO: 752) | CCTACGGGAGGCATCAGGCAGATCTCGGTTCCTCCATTAACCTATGGTGAAAGTCAGTCAGCCGGATTAGATACCCTAGTAGTC |
| (SEQ ID NO: 753) | CCTACGGGAGGCATCAGGCAGATCTCGACCTGTCCTTTCCTGTTACAGCGAAGTCAGTCAGCCGGATTAGATACCCTAGTAGTC |
| (SEQ ID NO: 754) | CCTACGGGAGGCATCAGGCAGATCTCGGTTCACGCCCAACAGTCAGGCCTTAGTCAGTCAGCCGGATTAGATACCCTAGTAGTC |
| (SEQ ID NO: 755) | CCTACGGGAGGCATCAGGCAGATCTCGCGATCGAACACTACTGAGCTGCATAGTCAGTCAGCCGGATTAGATACCCTAGTAGTC |
| (SEQ ID NO: 756) | CCTACGGGAGGCATCAGGCAGATCTCGCATGCCAACATGACGAAGTCTACCAGTCAGTCAGCCGGATTAGATACCCTAGTAGTC |
| (SEQ ID NO: 757) | CCTACGGGAGGCATCAGGCAGATCTCGGAGTACAGTCTAACCGTCTTTCTCAGTCAGTCAGCCGGATTAGATACCCTAGTAGTC |
| (SEQ ID NO: 758) | CCTACGGGAGGCATCAGGCAGATCTCGCCTACATGAGACAGTCTGTCTGCGAGTCAGTCAGCCGGATTAGATACCCTAGTAGTC |
| (SEQ ID NO: 759) | CCTACGGGAGGCATCAGGCAGATCTCGTCCGTGGTATAGCCGCACTCAAGTAGTCAGTCAGCCGGATTAGATACCCTAGTAGTC |
| (SEQ ID NO: 760) | CCTACGGGAGGCATCAGGCAGATCTCGTCTACGGCACGTTGTGGAAACTCCAGTCAGTCAGCCGGATTAGATACCCTAGTAGTC |
| (SEQ ID NO: 761) | CCTACGGGAGGCATCAGGCAGATCTCGATGCTGCAACACTTAGGCAGGTTCAGTCAGTCAGCCGGATTAGATACCCTAGTAGTC |
| (SEQ ID NO: 762) | CCTACGGGAGGCATCAGGCAGATCTCGTTCTCATGGAGGTAAGACTACTGGAGTCAGTCAGCCGGATTAGATACCCTAGTAGTC |
| (SEQ ID NO: 763) | CCTACGGGAGGCATCAGGCAGATCTCGCATAGTGATTGGCGCGAAGTTTCAAGTCAGTCAGCCGGATTAGATACCCTAGTAGTC |
| (SEQ ID NO: 764) | CCTACGGGAGGCATCAGGCAGATCTCGGCTATCAAGACACGATACACTGCCAGTCAGTCAGCCGGATTAGATACCCTAGTAGTC |
| (SEQ ID NO: 765) | CCTACGGGAGGCATCAGGCAGATCTCGCCGTGACAACTCTTGAAATCCCGGAGTCAGTCAGCCGGATTAGATACCCTAGTAGTC |
| (SEQ ID NO: 766) | CCTACGGGAGGCATCAGGCAGATCTCGCGTTCCTTGTTAGTTAGGGAGCGAAGTCAGTCAGCCGGATTAGATACCCTAGTAGTC |
| (SEQ ID NO: 767) | CCTACGGGAGGCATCAGGCAGATCTCGGGAATTATCGGTTTACTGTGGCCGAGTCAGTCAGCCGGATTAGATACCCTAGTAGTC |
| (SEQ ID NO: 768) | CCTACGGGAGGCATCAGGCAGATCTCGCATCAAGCATAGATATAAGGCCCAAGTCAGTCAGCCGGATTAGATACCCTAGTAGTC |

In another embodiment, spike-in control compositions are provided for use in a method that simultaneously 1) controls for cross-contamination and/or sample swapping and 2) control for different GC content samples (e.g., low, balanced, and high GC content). In this embodiment, nucleic acid constructs are used with barcode sequence fragments and primer binding site fragments, and with GC content fragments where the barcode sequence fragments and the GC content fragments are optionally positioned between universal sequence fragments (see FIG. 4). In one embodiment, the barcode sequence fragment is linked at its 3' end to the 5' end of the GC content fragment, and the barcode sequence fragment is linked at its 5' end to a universal sequence fragment while the GC content fragment is linked at its 3' end to a universal sequence fragment. Further in this embodiment, primer binding site fragments flank the universal sequence fragments. In this embodiment, the GC content fragment can be used to control for polymerase GC content bias.

Figure 4:
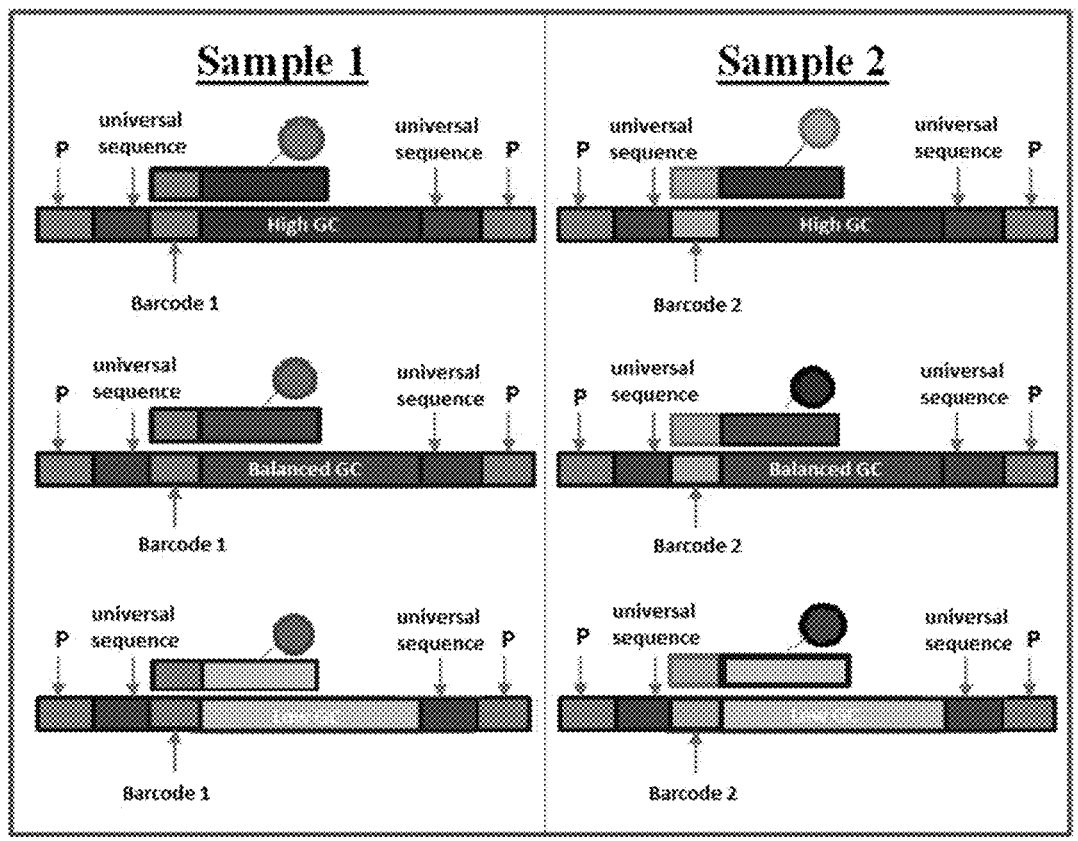
FIG. 4 shows a schematic of exemplary spike-in control nucleic acid constructs where the nucleic acid constructs include universal sequence fragments, and where exemplary sample 1 nucleic acid constructs include a barcode sequence fragment (barcode 1), and exemplary sample 2 nucleic acid constructs include a barcode sequence fragment (barcode 2) that is different than the barcode sequence fragment in the sample 1 nucleic acid constructs. The schematic also exemplifies nucleic acid constructs with a low GC content fragment, a balanced GC content fragment, and a high GC content fragment. A forward primer binding site fragment is included in the nucleic acid construct at the 5' end of the 5' universal sequence fragment and a reverse primer binding site fragment is included at the 3'end of the 3' universal sequence fragment. Both primer binding site fragments are labeled "P". In this example, each of the probes for each of the six nucleic acid constructs shown diagrammatically is unique and each probe is directed to the barcode sequence fragment in combination with GC content fragment sequence. The fluorophores for each of the probes are also different so that the different GC content fragments and the different barcode sequence fragments can be distinguished.
Figure 4:
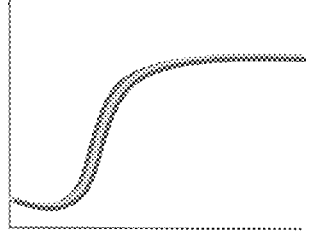
Figure 4:
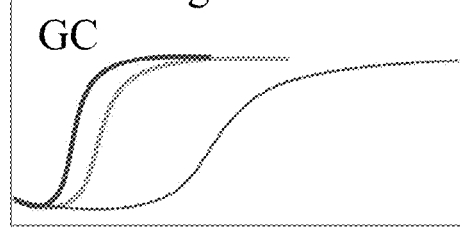

In this embodiment, the different GC content fragments (e.g., low, balanced, and high GC content) have the same barcode sequence fragments at each GC percentage (e.g., low, balanced, and high GC content), but for each separate sample the barcode sequence fragments are different (see FIG. 4).

In this embodiment, the GC content fragment can be from about 100 base pairs in length to about 270 base pairs in length, from about 100 base pairs in length to about 260 base pairs in length, from about 100 base pairs in length to about 250 base pairs in length, from about 100 base pairs in length to about 240 base pairs in length, from about 100 base pairs in length to about 230 base pairs in length, from about 100 base pairs in length to about 220 base pairs in length, from about 100 base pairs in length to about 210 base pairs in length, from about 100 base pairs in length to about 200 base pairs in length, from about 100 base pairs in length to about 190 base pairs in length, from about 100 base pairs in length to about 180 base pairs in length, from about 100 base pairs in length to about 170 base pairs in length, from about 100 base pairs in length to about 160 base pairs in length, from about 100 base pairs in length to about 150 base pairs in length, from about 100 base pairs in length to about 140 base pairs in length, from about 100 base pairs in length to about 130 base pairs in length, from about 100 base pairs in length to about 120 base pairs in length, from about 50 base pairs in length to about 270 base pairs in length, from about 50 base pairs in length to about 260 base pairs in length, from about 50 base pairs in length to about 250 base pairs in length, from about 50 base pairs in length to about 240 base pairs in length, from about 50 base pairs in length to about 230 base pairs in length, from about 50 base pairs in length to about 220 base pairs in length, from about 50 base pairs in length to about 210 base pairs in length, from about 50 base pairs in length to about 200 base pairs in length, from about 50 base pairs in length to about 190 base pairs in length, from about 50 base pairs in length to about 180 base pairs in length, from about 50 base pairs in length to about 170 base pairs in length, from about 50 base pairs in length to about 160 base pairs in length, from about 50 base pairs in length to about 150 base pairs in length, from about 50 base pairs in length to about 140 base pairs in length, from about 50 base pairs in length to about 130 base pairs in length, from about 50 base pairs in length to about 120 base pairs in length, from about 60 base pairs in length to about 120 base pairs in length, from about 70 base pairs in length to about 120 base pairs in length, from about 80 base pairs in length to about 120 base pairs in length, from about 90 base pairs in length to about 120 base pairs in length, or from about 100 base pairs in length to about 120 base pairs in length.

In embodiments where GC content fragments are present, the GC content of the GC content fragments can vary. As exemplary embodiments, the GC content fragments can have GC contents of about 1 to about 40 percent, about 1 to about 35 percent, about 1 to about 30 percent, about 1 to about 25 percent, about 1 to about 20 percent, about 35 to about 65 percent, about 40 to about 65 percent, about 40 to about 60 percent, about 40 to about 55 percent, about 40 to about 50 percent, about 45 to about 65 percent, about 45 to about 60 percent, about 45 to about 55 percent, about 45 to about 50 percent, about 65 to about 100 percent, about 65 to about 95 percent, about 65 to about 90 percent, about 65 to about 85 percent, about 65 to about 80 percent, about 65 to about 75 percent, about 65 to about 70 percent, about 60 to about 100 percent, about 60 to about 95 percent, about 60 to about 90 percent, about 60 to about 85 percent, about 60 to about 80 percent, about 60 to about 75 percent, or about 60 to about 70 percent. In one aspect, the GC content fragments can have low (e.g., about 1 to about 40 percent), balanced (e.g., about 40 to about 60 percent or about 45 to about 60 percent), or high GC content (e.g., about 60 to about 100 percent or about 65 to about 100 percent). In this embodiment, the GC content fragments in different nucleic acid constructs can have, for example, at least one, two, three, or four different GC content percentages in the different nucleic acid constructs (see FIG. 4).

The nucleic acid construct further comprises at least a first and a second primer binding site fragment. In this aspect, the primers can be any primers of interest. In this embodiment, the first primer binding site fragment can be linked at its 3'end to the 5' end of the first universal sequence fragment and the second primer binding site fragment can be linked at its 5' end to the 3' end of the second universal sequence fragment. In another embodiment, the universal sequence fragments are lacking and the primer binding site fragments are linked to the 5' and 3' ends of the barcode sequence fragment. In various embodiments, the primer binding site fragments can range in length from about 15 base pairs to about 28 base pairs, from about 15 base pairs to about 26 base pairs, from about 15 base pairs to about 24 base pairs, from about 15 base pairs to about 22 base pairs, from about 15 base pairs to about 20 base pairs, from about 16 base pairs to about 22 base pairs, from about 16 base pairs to about 20 base pairs, from about 17 base pairs to about 20 base pairs, or can be about 18 base pairs.

In an illustrative embodiment, the nucleic acid construct is a deoxyribonucleic acid construct. In another aspect, the nucleic acid construct is a ribonucleic acid. In another embodiment, the nucleic acid construct is incorporated into a plasmid. In yet another embodiment, the nucleic acid construct is incorporated into the genome of an organism.

In all of the various embodiments described above, the entire nucleic acid construct, not including plasmid sequence if a plasmid is present, can range in length from about 80 base pairs to about 300 base pairs, from about 80 base pairs to about 290 base pairs, from about 80 base pairs to about 280 base pairs, from about 80 base pairs to about 270 base pairs, from about 80 base pairs to about 260 base pairs, from about 80 base pairs to about 250 base pairs, from about 80 base pairs to about 240 base pairs, from about 80 base pairs to about 230 base pairs, from about 80 base pairs to about 220 base pairs, from about 80 base pairs to about 210 base pairs, from about 80 base pairs to about 200 base pairs, from about 80 base pairs to about 190 base pairs, from about 80 base pairs to about 180 base pairs, from about 80 base pairs to about 170 base pairs, or from about 80 base pairs to about 160 base pairs.

In another embodiment, any of the nucleic acids constructs, incorporated into a plasmid or not incorporated or encapsulated or not encapsulated, can be in the form of a kit for qPCR. In this illustrative aspect, the kit can further comprise a reagent for nucleic acid extraction, a reagent for nucleic acid purification, a reagent for amplification (for example a polymerase), a probe (e.g., a TaqMan probe), and/or instructions for use of the kit. In this illustrative embodiment, the kit can comprise more than one of the qPCR control compositions wherein each control composition comprises a different nucleic acid construct wherein the different nucleic acid constructs comprise different barcode sequence fragments (e.g., see the barcode sequence fragments contained in SEQ ID NOS:1 to 384 or SEQ ID NOS:384 to 768).

Figure 5:
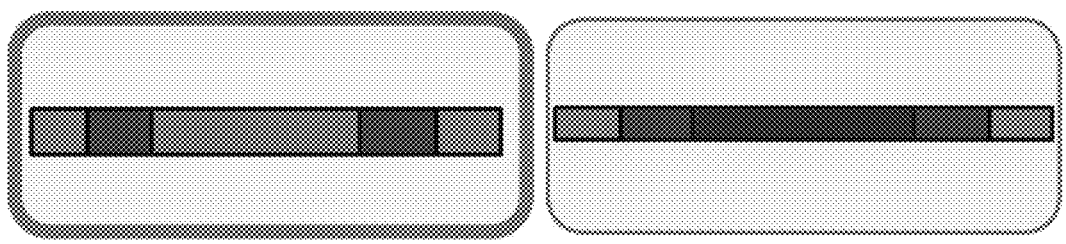
FIG. 5 shows schematically the direct encapsulation of an exemplary nucleic acid construct of FIG. 1 as described herein. The nucleic acid construct comprises primer binding site fragments. Probes with attached fluorophores for qPCR are also shown. The probes are for hybridization to the barcode sequence fragment and are not encapsulated. Unique probes with different fluorophores are shown with one probe being directed to the barcode sequence fragment in the first liposome composition shown, and the other probe being directed to the barcode sequence fragment in the second liposome composition shown, resulting in the ability to distinguish the nucleic acid constructs in the two types of liposomes.
Figure 5:
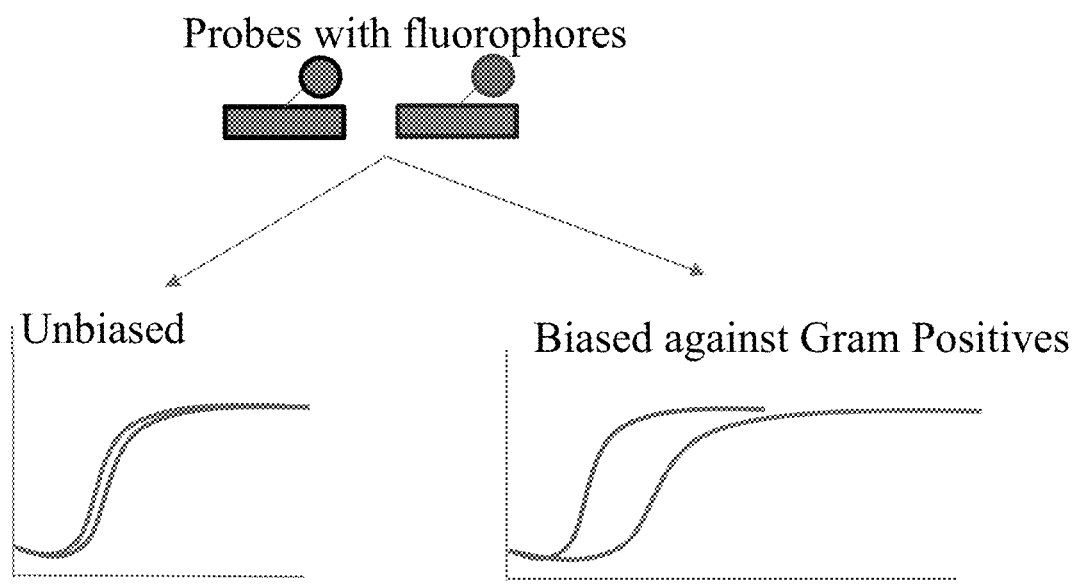
Figure 6:
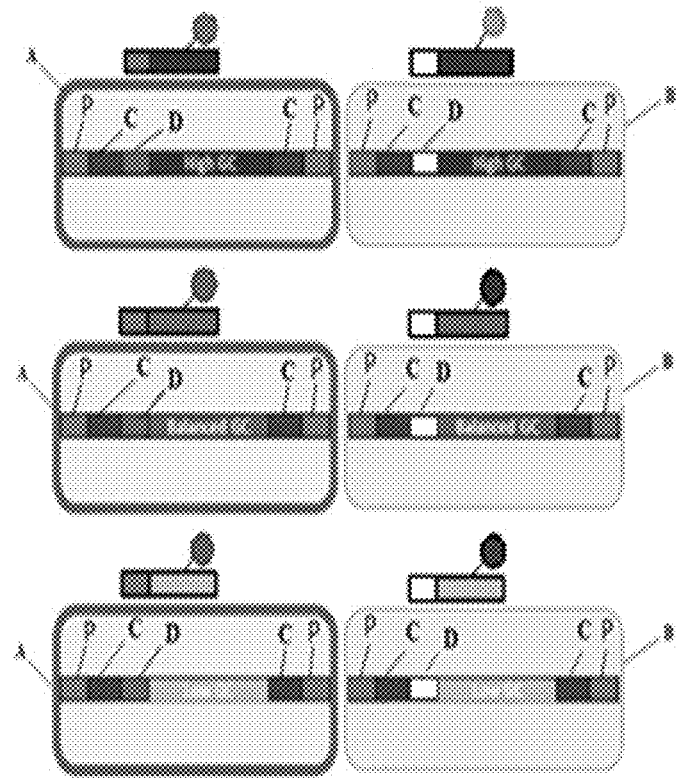
FIG. 6 shows a schematic of exemplary spike-in control nucleic acid constructs encapsulated within simulated cell membranes highly resistant to lysis (A) and within non-resistant (easy to lyse) simulated cell membranes (B). The highly resistant cell membranes (e.g., liposomes) include, for example, lipid formulations with higher crystal transition temperatures, and higher amounts of LPS, PG, teichoic acids, PEG, cholesterol, and/or cationic lipids to condense the nucleic acid constructs. The non-resistant simulated cell membranes may, for example, omit the preceding ingredients or include them to a lesser degree. The barcode sequence fragment (D) is different in cell membranes highly resistant to lysis (A) versus non-resistant (easy to lyse) simulated cell membranes (B). The schematic also exemplifies nucleic acid constructs with a low GC content fragment, a balanced GC content fragment, and a high GC content fragment. A forward primer binding site fragment is included in the nucleic acid construct at the 5' end of the 5' universal sequence fragment and a reverse primer binding site fragment is included at the 3'end of the 3' universal sequence fragment. Both primer binding site fragments are labeled "P". The probes are shown and are analogous to those shown in FIG. 4 and are not encapsulated.

In yet another illustrative aspect, the kits described herein can comprise more than one of any of the control compositions described herein wherein the nucleic acid construct in each control composition is encapsulated in a different type of liposome. In this embodiment, each control composition wherein the nucleic acid construct is encapsulated in a different type of liposome may have a different barcode sequence fragment to differentiate the various types of liposomes (see FIGS. 5 and 6).

In one aspect, quantitative PCR (qPCR) is performed on a target nucleic acid in a sample to quantify the target nucleic acid, and the control compositions described herein are used to control for cross-contamination, sample swapping, and/or for GC content bias in the qPCR assay. Methods and devices for performing qPCR are well-known in the art. To distinguish between the target nucleic acid and the nucleic acid constructs, described herein for use as control compositions, unique probes can be used that are complementary to and that hybridize to either the target nucleic acid or the nucleic acid constructs described herein and which are linked to different fluorophores. In one embodiment, the probe can hybridize to the barcode sequence fragment portion of the nucleic acid construct described herein. In another embodiment, where different GC content fragments with different percent GC content are used, the probe can hybridize to the barcode sequence fragment in combination with sequences of the specific GC content fragment being detected (see FIG. 4). In this embodiment, probes specific to a particular GC content fragment can be labeled with different fluorophores so that the different GC content fragments can be distinguished during qPCR (see FIG. 4). Similarly, in encapsulation embodiments where nucleic acid constructs in different types of liposomes, for example, are being distinguished, probes directed to the unique barcode sequence fragment in each encapsulated nucleic acid construct, and with different fluorophores attached to the probe can be used to distinguish nucleic acid constructs within liposomes of different compositions (see FIG. 5).

The probes can be any type of probe suitable for use in a qPCR assay and suitable for distinguishing between the various nucleic acid constructs, encapsulated or not encapsulated, described herein, and for allowing for quantitation of the target nucleic acid. An exemplary probe for use in the methods and compositions described herein is a hydrolysis probe (e.g. a TacMan probe). In exemplary embodiments, the probes can be labeled with fluorescent compounds, or other labeling agents known to those of skill in the art, that allow for detection and/or quantification of amplified DNA, such as by qPCR. In illustrative embodiments, the labels on the probes can be selected from 6-carboxyfluorescein (FAM™), TET™ (tetrachloro-6-carboxyfluorescein), JOE™ (2,7, -dimethoxy-4,5-dichloro-6-carboxyfluorescein), VIC™, HEX (hexachloro-6-carboxyfluorescein), TAMRA™ (6-carboxy-N,N,N',N'-tetramethylrhodamine), BHQ™, SYBR® Green, Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein, Oregon Green 488, Oregon Green 500, Oregon Green 514, Pacific Blue, REG, Rhodamine Green, Rhodamine Red, ROX, and/or Texas Red.

In one embodiment, the probes, primers for use in qPCR, and the nucleic acid constructs, including nucleic acid constructs incorporated into a plasmid, described herein can be made by methods well-known in the art, including chemical syntheses and recombinant methods. Such techniques are described in Sambrook et al., "Molecular Cloning: A Laboratory Manual", 3rd Edition, Cold Spring Harbor Laboratory Press, (2001), incorporated herein by reference. Plasmids, primers, probes, and the nucleic acid constructs described herein can also be made commercially (e.g., Blue Heron, Bothell, Wash. 98021). Techniques for purifying or isolating the probes, primers, or nucleic acid constructs, including nucleic acid constructs incorporated into a plasmid, described herein are well-known in the art. Such techniques are described in Sambrook et al., "Molecular Cloning: A Laboratory Manual", 3rd Edition, Cold Spring Harbor Laboratory Press, (2001), incorporated herein by reference. The nucleic acid constructs, including nucleic acid constructs incorporated into a plasmid, described herein can be analyzed by techniques known in the art, such as sequencing, to determine if the sequence is correct.

In one illustrative aspect, the nucleic acid construct, incorporated into a plasmid or not incorporated into a plasmid, can be encapsulated. In one exemplary embodiment, the nucleic acid construct, incorporated into a plasmid or not incorporated into a plasmid, can be encapsulated in a liposome, and the liposome can comprise a lipid selected from the group consisting of cholesterol, a cholesterol ester salt, a lipopolysaccharide, a sphingolipid, a peptidoglycan, a phospholipid, any other suitable lipid, and combinations thereof.

In this embodiment, liposomes can be closed, spherical vesicles comprising amphiphilic lipids in proportions such that they arrange themselves into multiple concentric bilayers when hydrated in aqueous solutions. In another aspect, the liposomes can be converted into single bilayer liposomes which are useful carriers of both hydrophilic molecules, which can reside entrapped in the aqueous interior of the liposome, and of hydrophobic molecules, which can reside entrapped in the lipid bilayer. An exemplary hydrophilic chain constituent is polyethylene glycol.

In various embodiments, the lipids can include those having two hydrocarbon chains, typically acyl chains, and a polar head group, such as phospholipids and glycolipids. In this aspect, phospholipids may include any one type of phospholipid or a combination of phospholipids capable of forming liposomes, including, but not limited to, phosphatidylcholines, phosphatidylethanolamine, phosphatidic acid, phosphatidylinositol, and sphingomyelin, where the two hydrocarbon chains are typically between about 14 to 22 carbons in length, and have varying degrees of unsaturation. The glycolipids include, but are not limited to, cerebrosides and gangliosides. Exemplary phosphatidylcholines, include those obtained from natural sources or those that are partially or wholly synthetic, or are of variable chain length and unsaturation.

In various embodiments, the nucleic acid construct can be encapsulated, incorporated into a plasmid or not incorporated into a plasmid, into a simulated cell membrane that mimics the cell membrane of the microorganism or a eukaryotic cell, or another cell of interest. In one illustrative embodiment, lipids with varying crystal transition temperatures, including cholesterol and lipopolysaccharide, can be incorporated during encapsulation to better mimic the mechanical and material characteristics of a microorganism cell wall (e.g., a bacterial cell wall). In this embodiment, variation in liposome production parameters such as the lipid:DNA ratio, the solvent:non-solvent ratio, and the lipid charge can be used to better tune the liposome composition and size to mimic the cell membrane of the microorganism or a eukaryotic cell, or another cell of interest.

For example, membrane rigidity may be increased with increasing amounts of cholesterol. In one embodiment, this allows the production of a range of liposomes that include easy to lyse (i.e., non-resistant liposomes) through difficult to lyse liposomes (i.e., resistant liposomes). In another embodiment, LPS may be used to mimic Gram-negative bacterial membranes. The hydrated saccharide chains can act as a barrier to hydrophobic species while the phospholipid layer can act as a barrier to hydrophilic species. A periplasm layer of water and peptidoglycan (PG) separates the LPS outer membrane from an inner membrane composed of a more conventional phospholipid lipid bilayer. Polyethylene Glycol (PEG) is a hydrophilic, biologically inert, synthetic material that may confer similar membrane robustness. The PEG can assemble into a brush-like layer on the outer membrane of the liposomes, and act as a hydrated barrier while also increasing the apparent size. Although PEG has been extensively used in liposomes for drug delivery, it may not have been demonstrated as an LPS mimic in an artificial cell. PG, teichoic acids, or similar materials can be added to mimic a Gram-positive cell wall, as the thick PG layers increase lysis resistance. In one aspect, after synthesis, liposome size can be adjusted by extruding the liposomes through a filter membrane with well-defined pore sizes. In this embodiment, the final liposome will comprise small, unilamellar vesicles with a size that is determined by the pore size in the membrane used for extrusion. With no extrusion step, the liposomes may be larger, multi-lamellar liposomes. In one illustrative aspect, direct encapsulation of the nucleic acid construct without a plasmid or genome backbone is used (shown schematically in FIGS. 5 and 6).

In all of the encapsulation embodiments described above, encapsulation of the control composition for qPCR, including the nucleic acid construct, or by incorporation into the genome of a cell (e.g., a bacterial or eukaryotic cell) allows for the control composition for qPCR to be used in every step of qPCR for an unknown test sample: from nucleic acid extraction to nucleic acid purification to qPCR because degradation of the control sample can be avoided so that sample cross-contamination and sample swapping can be effectively monitored throughout the protocol. In another aspect, the nucleic acid constructs can be encapsulated in a simulated cell membrane to control for differential lysis during sample preparation of different samples. In another illustrative aspect, encapsulation of the nucleic acid constructs described herein can enable control for extraction efficiency, cross contamination, and extraction quality.

Figure 2A:
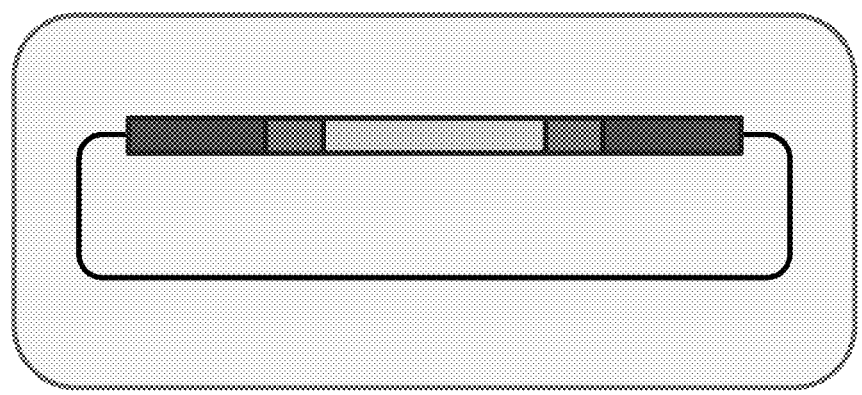
FIG. 2A shows schematically the exemplary nucleic acid construct of FIG. 1 as described herein cloned into a plasmid.
Figure 2B:
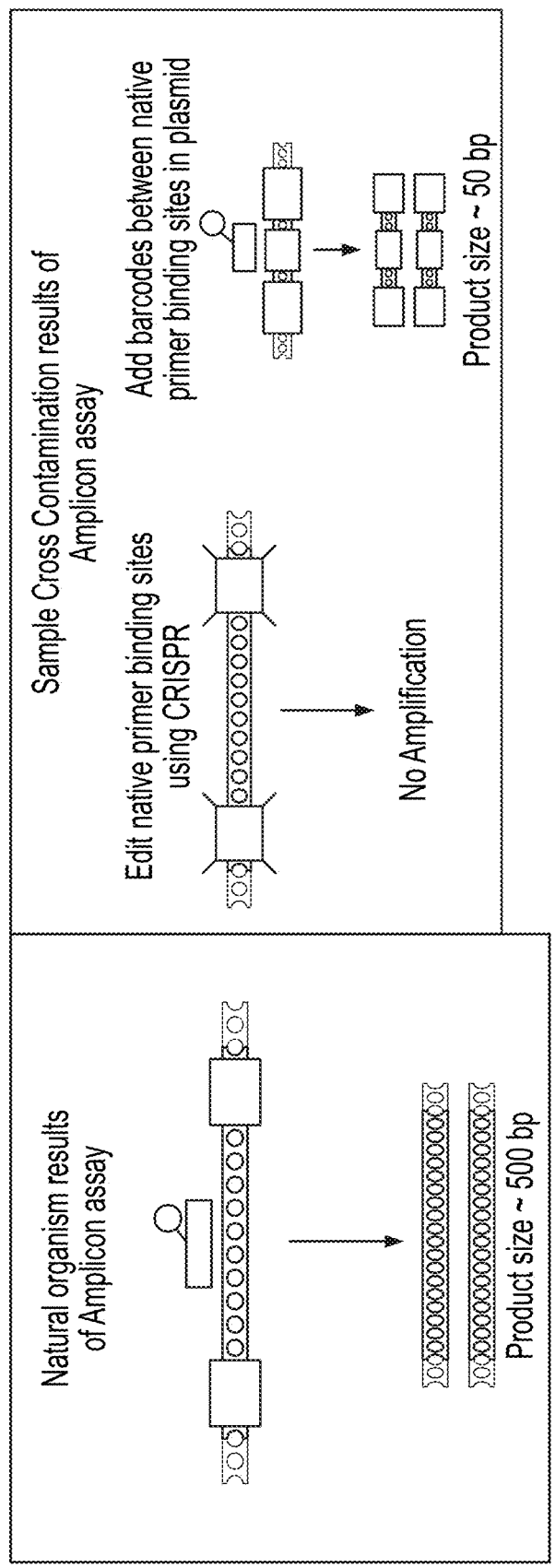
FIG. 2B shows schematically the exemplary nucleic acid construct of FIG. 1 as described herein inserted into the genome of a microorganism. In one aspect, the microorganism could be modified utilizing gene editing (e.g., CRISPR) so that the natural primer binding sites are removed before inserting the nucleic acid construct described herein into the genome of the microorganism. Unique probes with different fluorophores are also shown with one probe being directed to the native sequence between the natural primer binding sites and one probe being directed to the barcode sequence fragment resulting in quantification of the barcode and the native sequence.
Figure 2C:
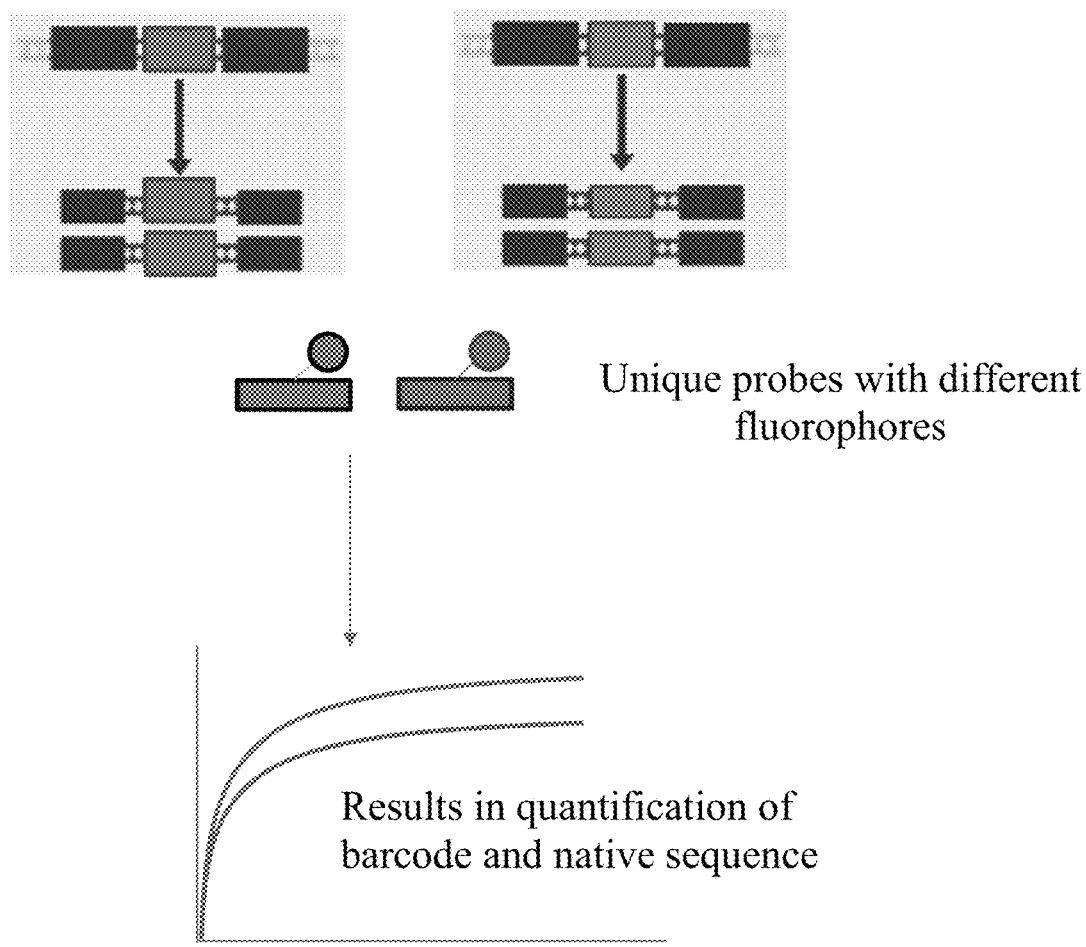
FIG. 2C shows schematically the exemplary nucleic acid construct of FIG. 1 as described herein where the barcode sequence fragment is inserted into the genome of a microorganism between natural primer binding sites. In one aspect, the microorganism could be modified utilizing gene editing (e.g., CRISPR) so that the sequence between the natural primer binding sites is replaced with the barcode. Unique probes with different fluorophores are also shown with one probe being directed to the native sequence between the natural primer binding sites and one probe being directed to the barcode sequence fragment resulting in quantification of the barcode and the native sequence.
Figure 3A:
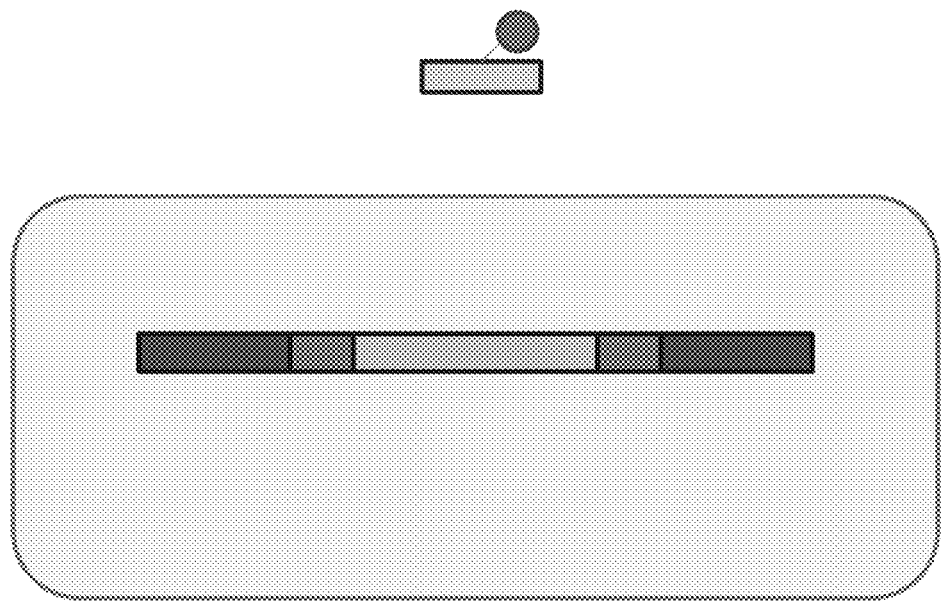
FIG. 3A shows schematically the direct encapsulation of the exemplary nucleic acid construct of FIG. 1 as described herein without a plasmid or genome backbone. The nucleic acid construct comprises primer binding site fragments. A probe with an attached fluorophore for qPCR is also shown. The probe is for hybridization to the barcode sequence fragment and is not encapsulated.
Figure 3B:
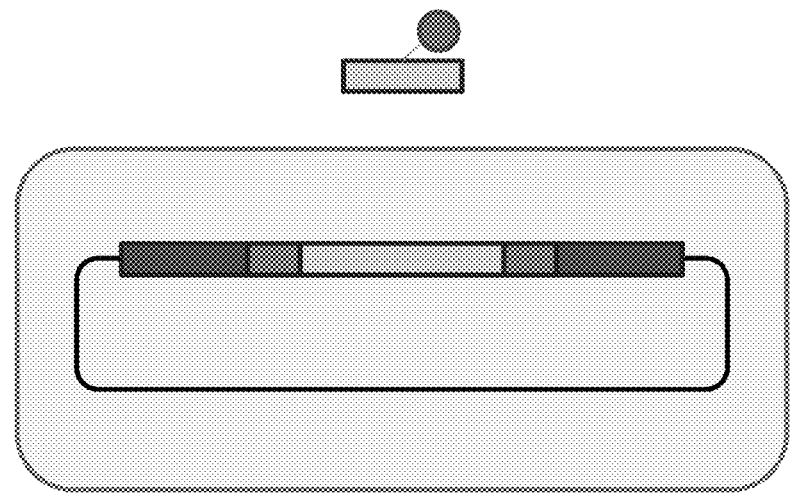
FIG. 3B shows schematically the direct encapsulation of the exemplary nucleic acid construct of FIG. 1 as described herein within a plasmid. The nucleic acid construct comprises primer binding site fragments. A probe with an attached fluorophore for qPCR is also shown. The probe is for hybridization to the barcode sequence fragment and is not encapsulated.

In embodiments where the nucleic acid construct is not artificially encapsulated in, for example, a liposome, the nucleic acid construct, or a barcode sequence fragment, can be incorporated into the genome of a microorganism for use as a control composition for qPCR. These embodiments are shown schematically in FIGS. 2A, 2B, and 2C. If the primer binding sites are present in the microorganism to be utilized, the microorganism could be modified utilizing gene editing, for example, so that the natural primer binding sites are removed (see FIG. 2B). In another embodiment, the natural sequence between natural primer binding sites in the microorganism could be replaced with a barcode sequence (see FIG. 2C). In one aspect, the CRISPR/Cas9 system for genome editing could be used as well as other genome editing systems, such as ZFNs, custom designed homing endonucleases, and TALENS systems.

The CRISPR/Cas9 system for genome editing has benefits over other genome editing systems. In this embodiment, the Cas9 endonuclease is capable of introducing a double strand break into a DNA target sequence (e.g., the natural primer binding sites described above). In this aspect, the Cas9 endonuclease is guided by the guide polynucleotide (e.g., guide RNA) to recognize and optionally introduce a double strand break at a specific target site into the genome of a cell, such as a microorganism, a eukaryotic cell, or another cell of interest for use in the methods described herein. The Cas9 endonuclease can unwind the DNA duplex in close proximity to the genomic target site and cleaves both DNA strands upon recognition of a target sequence by a guide polynucleotide (e.g., guide RNA), but only if the correct protospacer-adjacent motif (PAM) is approximately oriented at the 3' end of the target. In this embodiment, the donor polynucleotide construct (e.g., the nucleic acid construct described herein) can then be incorporated into the genomic target site. Methods for using the CRISPR/Cas9 system for genome editing are well-known in the art.

In one illustrative aspect, for qPCR, the nucleic acids in the sample (e.g., microorganisms such as bacteria or viruses) and the nucleic acids in the control composition for qPCR (e.g., the nucleic acid construct incorporated or not incorporated into a plasmid or into the genome of a microorganism), are extracted and purified for analysis. In various embodiments, the preparation of the nucleic acids (e.g., DNA or RNA) can involve rupturing the cells that contain the nucleic acids (e.g., cells of a microorganism or the nucleic acid construct in a simulated cell membrane) and isolating and purifying the nucleic acids (e.g., DNA or RNA) from the lysate. Techniques for rupturing cells and for isolation and purification of nucleic acids (e.g., DNA or RNA) are well-known in the art. In one embodiment, for example, nucleic acids may be isolated and purified by rupturing cells using a detergent or a solvent, such as phenol-chloroform. In another aspect, nucleic acids (e.g., DNA or RNA) may be separated from the lysate by physical methods including, but not limited to, centrifugation, pressure techniques, or by using a substance with an affinity for nucleic acids (e.g., DNA or RNA), such as, for example, beads that bind nucleic acids. In one embodiment, after sufficient washing, the isolated, purified nucleic acids may be suspended in either water or a buffer. In another aspect, the nucleic acids (e.g., DNA or RNA) are "isolated" or "purified" before qPCR. In one embodiment, "isolated" means that the nucleic acids used in qPCR are removed from their normal environment (e.g., a nucleic acid is removed from the genome of an organism). In another aspect, "purified" means in the context of the nucleic acids that are used in qPCR that the nucleic acids are substantially free of other cellular material, or culture medium, or other chemicals used in the extraction process. In other embodiments, commercial kits are available, such as Qiagen™ (e.g., Qiagen DNeasy PowerSoil Kit™), Nuclisensm™, and Wizard™ (Promega), and Promegam™ for extraction and purification of nucleic acids. Methods for preparing nucleic acids for qPCR are also described in Green and Sambrook, "Molecular Cloning: A Laboratory Manual", 4th Edition, Cold Spring Harbor Laboratory Press, (2012), incorporated herein by reference.

In various illustrative embodiments, using the control compositions for qPCR described herein, patient samples or environmental samples (e.g., containing animal, plant, bacteria, viruses, fungi, or archaea) can be analyzed by qPCR. In accordance with the invention, the term "patient" means a human or an animal, such as a domestic animal (e.g., a dog or a cat). Accordingly, the methods and control compositions for qPCR described herein can be used, for example, for human clinical medicine (e.g., infectious disease diagnosis, cancer diagnosis, infectious disease biosurveillance), veterinary applications, forensics, environmental or ecological use.

In various aspects, the patient can be a human, or in the case of veterinary applications, can be a laboratory, agricultural, domestic or wild animal. In one embodiment, the patient can include, but is not limited to, a human, a laboratory animal such as a rodent (e.g., mice, rats, hamsters, etc.), a rabbit, a monkey, a chimpanzee, a domestic animal such as a dog, a cat, and a rabbit, and an agricultural animal such as a cow, a horse, a pig, a sheep, a goat, a chicken, and a wild animal in captivity such as a bear, a panda, a lion, a tiger, a leopard, an elephant, a zebra, a giraffe, a gorilla, a dolphin, and a whale.

In various illustrative embodiments, the samples that can be tested using the control compositions for qPCR and the methods described herein comprise patient body fluids including, but not limited to, urine, nasal secretions, nasal washes, inner ear fluids, bronchial lavages, bronchial washes, alveolar lavages, spinal fluid, bone marrow aspirates, sputum, pleural fluids, synovial fluids, pericardial fluids, peritoneal fluids, saliva, tears, gastric secretions, a stool sample, reproductive tract secretions, such as seminal fluid, lymph fluid, and whole blood, serum, or plasma, or any other suitable patient sample. In another embodiment, nucleic acids extracted from microorganisms (e.g., bacteria or viruses) isolated or purified from patient samples or environmental samples can be tested using the control compositions for qPCR and methods described herein. In various embodiments, patient tissue samples that can be tested by using the control compositions for qPCR and the methods described herein can include tissue biopsies of hospital patients or out-patients and autopsy specimens. As used herein, the term "tissue" includes, but is not limited to, biopsies (including tumor biopsies), autopsy specimens, cell extracts, hair, tissue sections, aspirates, tissue swabs, and fine needle aspirates.

In various illustrative embodiments, environmental samples that can be tested by using the control compositions for qPCR and the methods described herein can be selected from the group consisting of a soil sample, a water sample, a food sample, an air sample, a plant sample, an industrial waste sample, an agricultural sample, a surface wipe sample, a dust sample, a hair sample, and an animal sample, or any other suitable environmental sample. In various illustrative embodiments, the microorganisms present in the patient sample or the environmental sample to be tested can be bacteria or viruses. In this aspect, the bacteria can be selected from Gram-negative and Gram-positive cocci and bacilli, acid-fast bacteria, and can comprise antibiotic-resistant bacteria, or any other known bacteria having a nucleic acid sequence to target. In another illustrative aspect, the bacteria can be selected from the group consisting of *Pseudomonas* species, *Staphylococcus* species, *Streptococcus* species, *Escherichia* species, Haemophillus species, *Neisseria* species, *Chlamydia* species, *Helicobacter* species, *Campylobacter* species, *Salmonella* species, *Shigella* species, *Clostridium* species, *Treponema* species, *Ureaplasma* species, *Listeria* species, *Legionella* species, *Mycoplasma* species, and *Mycobacterium* species, or the group consisting of *S. aureus, P. aeruginosa*, and *E. coli*. In another aspect, the viruses can be selected from DNA and RNA viruses, or can be selected from the group consisting of papilloma viruses, parvoviruses, adenoviruses, herpesviruses, vaccinia viruses, arenaviruses, coronaviruses, rhinoviruses, respiratory syncytial viruses, influenza viruses, picornaviruses, paramyxoviruses, reoviruses, retroviruses, and rhabdoviruses. In another illustrative embodiment, mixtures of any of these microorganisms can be present in the patient sample or the environmental sample. In yet another embodiment, the sample to be tested comprises eukaryotic cells.

In one illustrative aspect, a method is provided. The method is for monitoring cross-contamination or sample swapping over all steps of qPCR including collection of a sample comprising DNA, DNA extraction from the sample, purification of the extracted DNA, and qPCR. The method comprises a) spiking the sample with a control composition comprising a nucleic acid construct wherein the nucleic acid construct comprises at least one barcode sequence fragment linked to primer binding site fragments and wherein the nucleic acid construct is a deoxyribonucleic acid construct, b) extracting total DNA wherein total DNA comprises the DNA from the sample and DNA from the nucleic acid construct, c) purifying total DNA, d) performing qPCR on the extracted, purified total DNA, and e) detecting the nucleic acid construct in total DNA using a probe.

In another illustrative aspect, a method is provided. The method is for monitoring cross-contamination or sample swapping during qPCR. The method comprises a) spiking the sample, after DNA extraction and purification and before qPCR, with a control composition comprising a nucleic acid construct wherein the nucleic acid construct comprises at least one barcode sequence fragment, and 5' and 3' primer binding site fragments, wherein the nucleic acid construct is a deoxyribonucleic acid construct, wherein total DNA is obtained after spiking the sample, and wherein total DNA comprises the DNA from the sample and the DNA from the nucleic acid construct, b) extracting total DNA wherein total DNA comprises the DNA from the sample and DNA from the nucleic acid construct, c) purifying total DNA, d) performing qPCR on the extracted, purified total DNA, and e) detecting the nucleic acid construct in total DNA using a probe.

In another embodiment, a method is provided for qPCR using any of the control compositions described herein that contain GC content fragments, where the method is for monitoring sample cross-contamination and/or sample swapping and for controlling GC content bias. The method comprises a) extracting DNA from a sample, b) purifying the DNA, c) spiking the sample, after DNA extraction and purification and before qPCR, with a control composition comprising a nucleic acid construct wherein the nucleic acid construct comprises at least one barcode sequence fragment, at least one GC content fragment, and 5' and 3' primer binding site fragments, wherein the nucleic acid construct is a deoxyribonucleic acid construct, wherein total DNA is obtained after spiking the sample, and wherein total DNA comprises the DNA from the sample and the DNA from the nucleic acid construct, d) performing qPCR on the extracted, purified total DNA, and e) detecting the nucleic acid construct in total DNA using a probe.

In another embodiment, a method is provided for qPCR using any of the control compositions described herein that contain GC content fragments. The qPCR method is for monitoring sample cross-contamination and/or sample swapping and for controlling GC content bias in samples. The method comprises a) spiking a sample with a qPCR control composition comprising a nucleic acid construct wherein the nucleic acid construct comprises at least one barcode sequence fragment, at least one GC content fragment, and 5' and 3' primer binding site fragments, and wherein the nucleic acid construct is a deoxyribonucleic acid construct, b) extracting total DNA from the sample wherein total DNA comprises the DNA from the sample and the DNA from the nucleic acid construct, c) purifying total DNA, d) performing qPCR on the extracted, purified total DNA, and e) detecting and the nucleic acid construct in total DNA using a probe.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11441176B2). An electronic copy of the "Sequence Listing" will also be available from the USPTO upon request and payment of the fee set forth in 37 CFR 1.19(b)(3).

What is claimed is:

1. A qPCR control composition, said control composition comprising i) a first nucleic acid construct comprising at least one barcode sequence fragment and at least one GC content fragment, wherein the first nucleic acid construct further comprises at least a first and a second primer binding site fragment, and ii) a second nucleic acid construct comprising the same barcode sequence fragment as in the first nucleic acid construct and at least one GC content fragment with a different percent GC content than the GC content fragment in the first nucleic acid construct, wherein the second nucleic acid construct further comprises at least a first and a second primer binding site fragment.

2. The control composition of claim 1 wherein the control composition is used to determine if cross-contamination between samples for qPCR has occurred or if sample swapping has occurred for qPCR samples.

3. The control composition of claim 1 wherein the first and the second nucleic acid constructs further comprise at least a first and a second universal sequence fragment and wherein the first universal sequence fragment is linked to the 5' end of the barcode sequence fragment, the barcode sequence fragment is between the first universal sequence fragment and the GC content fragment, and the second universal sequence fragment is linked to the 3' end of the GC content fragment.

4. The control composition of claim 3 wherein the first primer binding site fragment is linked at its 3'end to the 5' end of the first universal sequence fragment and the second primer binding site fragment is linked at its 5' end to the 3' end of the second universal sequence fragment.

5. The control composition of claim 1 wherein the barcode sequence fragments comprise a unique sequence not present in any known genome.

6. The control composition of claim 2 wherein sample cross-contamination and/or sample swapping can be monitored over all steps of a qPCR protocol including collection of the sample, extraction of total DNA, purification of the extracted total DNA, and qPCR.

7. The control composition of claim 1 wherein one or more of the GC content fragments has a GC content of about 1 to about 40 percent.

8. The control composition of claim 1 wherein one or more of the GC content fragments has a GC content of about 40 to about 60 percent.

9. The control composition of claim 1 wherein one or more of the GC content fragments has a GC content of about 60 to about 100 percent.

10. The control composition of claim 1 further comprising a third nucleic acid construct with a GC content fragment with a different percent GC content than the GC content fragments in the first and the second nucleic acid constructs.

11. The control composition of claim 10 further comprising a fourth nucleic acid construct with a GC content fragment with a different percent GC content than the GC content fragments in the first, the second, and the third nucleic acid constructs.

12. The control composition of claim 10 wherein the percent GC contents are about 1 to about 40 percent, about 40 percent to about 60 percent, and about 60 percent to about 100 percent.

13. The control composition of claim 1 wherein the control composition is used to determine if cross-contamination between samples for qPCR has occurred.

14. The control composition of claim 1 wherein the control composition is used to determine if sample swapping has occurred for qPCR samples.

15. The control composition of claim 1 wherein the GC content fragments are used to control for polymerase GC content bias.

16. The control composition of claim 1 in combination with a probe.

17. The control composition of claim 1 wherein the first and second nucleic acid constructs are deoxyribonucleic acid constructs.

18. The control composition of claim 1 wherein the first and second nucleic acid constructs further comprise at least a first and a second universal sequence fragment.

19. The control composition of claim 16 wherein the probe is a TaqMan probe.

* * * * *